US012799470B2

(12) United States Patent
Liu et al.

(10) Patent No.: US 12,799,470 B2
(45) Date of Patent: Nov. 17, 2026

(54) EVOLUTION OF BOTULINUM NEUROTOXIN PROTEASES

(71) Applicants: The Broad Institute, Inc., Cambridge, MA (US); President and Fellows of Harvard College, Cambridge, MA (US); Children's Medical Center Corporation, Boston, MA (US)

(72) Inventors: David R. Liu, Cambridge, MA (US); Travis R. Blum, Cambridge, MA (US); Min Dong, Boston, MA (US); Hao Liu, Boston, MA (US)

(73) Assignees: The Broad Institute, Inc., Cambridge, MA (US); President and Fellows of Harvard College, Cambridge, MA (US); Children's Medical Center Corporation, Boston, MA (US)

( * ) Notice: Subject to any disclaimer, the term of this patent is extended or adjusted under 35 U.S.C. 154(b) by 550 days.

(21) Appl. No.: 18/268,178

(22) PCT Filed: Dec. 17, 2021

(86) PCT No.: PCT/US2021/064125
§ 371 (c)(1),
(2) Date: Jun. 16, 2023

(87) PCT Pub. No.: WO2022/133266
PCT Pub. Date: Jun. 23, 2022

(65) Prior Publication Data

US 2024/0052331 A1 Feb. 15, 2024

Related U.S. Application Data

(60) Provisional application No. 63/127,340, filed on Dec. 18, 2020.

(51) Int. Cl.

| | |
|---|---|
| ***C12N 9/52*** | (2006.01) |
| ***C07K 14/47*** | (2006.01) |
| ***C12N 9/16*** | (2006.01) |
| ***C12N 15/86*** | (2006.01) |

(52) U.S. Cl.
CPC ............ *C12N 9/52* (2013.01); *C07K 14/4703* (2013.01); *C12N 9/16* (2013.01); *C12N 15/86* (2013.01); *C07K 2319/00* (2013.01); *C12N 2740/15043* (2013.01); *C12Y 301/04011* (2013.01); *C12Y 304/24069* (2013.01)

(58) Field of Classification Search
CPC . C12N 9/52; C12N 9/16; C12N 15/86; C12N 2740/15043; C07K 14/4703; C07K 2319/00; C07K 14/33; C12Y 301/04011; C12Y 304/24069
See application file for complete search history.

(56) References Cited

U.S. PATENT DOCUMENTS

| | | | |
|---|---|---|---|
| 5,057,432 A | 10/1991 | Wangersky et al. | |
| 5,223,409 A | 6/1993 | Ladner et al. | |
| 5,658,727 A | 8/1997 | Barbas et al. | |
| 5,712,089 A | 1/1998 | Borrebaeck et al. | |
| 5,821,047 A | 10/1998 | Garrard et al. | |
| 5,880,275 A | 3/1999 | Fischhoff et al. | |
| 5,965,124 A | 10/1999 | Feinberg et al. | |
| 6,033,874 A | 3/2000 | Baum et al. | |
| 6,156,509 A | 12/2000 | Schellenberger | |
| 6,262,242 B1 | 7/2001 | Steck et al. | |
| 6,429,298 B1 | 8/2002 | Ellington et al. | |
| 6,713,063 B1 | 3/2004 | Malvar et al. | |
| 6,815,194 B2 | 11/2004 | Honjo et al. | |
| 6,884,870 B2 | 4/2005 | Bruce et al. | |
| 6,962,705 B2 | 11/2005 | Malvar et al. | |
| 6,969,731 B1 | 11/2005 | Tang et al. | |
| 7,049,089 B2 * | 5/2006 | Xiao | C12Y 301/04003 435/193 |
| 7,064,249 B2 | 6/2006 | Corbin et al. | |
| 7,070,982 B2 | 7/2006 | Malvar et al. | |
| 9,023,594 B2 | 5/2015 | Liu et al. | |
| 9,228,207 B2 | 1/2016 | Liu et al. | |
| 9,267,127 B2 | 2/2016 | Liu et al. | |

(Continued)

FOREIGN PATENT DOCUMENTS

| | | | |
|---|---|---|---|
| EP | 0289479 A2 | 11/1988 | |
| EP | 3115457 A1 | 1/2017 | |

(Continued)

OTHER PUBLICATIONS

Lemmon, M., Pleckstrin homology (PH) domains and phosphoinositides. Biochem Soc Symp. 2007;(74):81-93 (Year: 2007).*

(Continued)

*Primary Examiner* — Robert B Mondesi
*Assistant Examiner* — Naghmeh Nina Moazzami
(74) *Attorney, Agent, or Firm* — Wolf, Greenfield & Sacks, P.C.

(57) ABSTRACT

The disclosure provides fusion proteins comprising a pleckstrin homology (PH) domain and a variant of Botulinum neurotoxin E (BoNT E) protease that cleaves certain non-canonical protein targets (e.g., PTEN). Fusion proteins described in the disclosure are useful for cleaving target proteins found in a cell, that is, in an intracellular environment. Aspects of the disclosure provide methods for inhibiting PTEN amount, activity, or function in a cell or subject, the methods comprising administering to a call or subject a fusion protein described herein.

16 Claims, 3 Drawing Sheets

Specification includes a Sequence Listing.

(56) References Cited

U.S. PATENT DOCUMENTS

| | | | |
|---|---|---|---|
| 9,340,799 | B2 | 5/2016 | Liu et al. |
| 9,340,800 | B2 | 5/2016 | Liu et al. |
| 9,359,599 | B2 | 6/2016 | Liu et al. |
| 9,394,537 | B2 | 7/2016 | Liu et al. |
| 9,526,784 | B2 | 12/2016 | Liu et al. |
| 9,567,589 | B2 | 2/2017 | Jin et al. |
| 9,737,604 | B2 | 8/2017 | Jin et al. |
| 9,766,216 | B2 | 9/2017 | Wada et al. |
| 9,771,574 | B2 | 9/2017 | Liu et al. |
| 9,849,163 | B2 * | 12/2017 | Chaddock ............... A61P 25/18 |
| 10,179,911 | B2 | 1/2019 | Liu et al. |
| 10,227,581 | B2 | 3/2019 | Liu et al. |
| 10,336,997 | B2 | 7/2019 | Liu et al. |
| 10,392,674 | B2 | 8/2019 | Liu et al. |
| 10,597,679 | B2 | 3/2020 | Liu et al. |
| 10,612,011 | B2 | 4/2020 | Liu et al. |
| 10,682,410 | B2 | 6/2020 | Liu et al. |
| 10,920,208 | B2 | 2/2021 | Liu et al. |
| 11,046,948 | B2 | 6/2021 | Liu et al. |
| 11,078,469 | B2 | 8/2021 | Liu et al. |
| 11,104,967 | B2 | 8/2021 | Liu et al. |
| 11,214,792 | B2 | 1/2022 | Liu et al. |
| 11,299,729 | B2 | 4/2022 | Badran et al. |
| 11,447,809 | B2 | 9/2022 | Bryson, Jr. et al. |
| 11,524,983 | B2 | 12/2022 | Badran et al. |
| 11,624,130 | B2 | 4/2023 | Liu et al. |
| 11,760,986 | B2 | 9/2023 | Liu et al. |
| 11,905,623 | B2 | 2/2024 | Liu et al. |
| 11,913,040 | B2 | 2/2024 | Liu et al. |
| 11,913,044 | B2 | 2/2024 | Liu et al. |
| 12,060,553 | B2 | 8/2024 | Packer et al. |
| 12,366,009 | B2 | 7/2025 | Liu et al. |
| 12,398,390 | B2 | 8/2025 | Liu et al. |
| 2002/0132327 | A1 | 9/2002 | Hay et al. |
| 2003/0119764 | A1 | 6/2003 | Loeb et al. |
| 2003/0167533 | A1 | 9/2003 | Yadav et al. |
| 2003/0186292 | A1 | 10/2003 | MacNeil et al. |
| 2003/0203480 | A1 | 10/2003 | Kovesdi et al. |
| 2005/0019753 | A1 | 1/2005 | Kukolj et al. |
| 2005/0100973 | A1 | 5/2005 | Steward et al. |
| 2006/0112447 | A1 | 5/2006 | Bogdanova et al. |
| 2006/0160222 | A1 | 7/2006 | Rozwadowski et al. |
| 2006/0166319 | A1 | 7/2006 | Chan et al. |
| 2008/0220502 | A1 | 9/2008 | Schellenberger et al. |
| 2009/0215110 | A1 | 8/2009 | Gibson et al. |
| 2009/0227463 | A1 | 9/2009 | Reif et al. |
| 2009/0300777 | A1 | 12/2009 | Nakayama |
| 2010/0297180 | A1 | 11/2010 | Shone |
| 2011/0177495 | A1 | 7/2011 | Liu et al. |
| 2011/0318385 | A1 | 12/2011 | Jackson et al. |
| 2012/0128649 | A1 | 5/2012 | Chaddock et al. |
| 2012/0190825 | A1 | 7/2012 | Neumann et al. |
| 2012/0196322 | A1 | 8/2012 | Siurkus et al. |
| 2013/0059931 | A1 | 3/2013 | Petersen-Mahrt et al. |
| 2013/0117869 | A1 | 5/2013 | Duchateau et al. |
| 2013/0345064 | A1 | 12/2013 | Liu et al. |
| 2013/0345065 | A1 | 12/2013 | Liu et al. |
| 2014/0201858 | A1 | 7/2014 | Ostertag et al. |
| 2015/0056177 | A1 | 2/2015 | Liu et al. |
| 2015/0259721 | A1 | 9/2015 | Brunt et al. |
| 2015/0275202 | A1 | 10/2015 | Liu et al. |
| 2016/0002301 | A1 | 1/2016 | Je et al. |
| 2016/0201040 | A1 | 7/2016 | Liu et al. |
| 2016/0348096 | A1 | 12/2016 | Liu et al. |
| 2017/0009224 | A1 | 1/2017 | Liu et al. |
| 2017/0029844 | A1 | 2/2017 | Ball et al. |
| 2017/0044520 | A1 | 2/2017 | Liu et al. |
| 2017/0233708 | A1 | 8/2017 | Liu et al. |
| 2018/0057545 | A9 | 3/2018 | Liu et al. |
| 2018/0087046 | A1 | 3/2018 | Liu et al. |
| 2018/0237758 | A1 | 8/2018 | Liu et al. |
| 2019/0219575 | A1 | 7/2019 | Gray et al. |
| 2019/0256842 | A1 | 8/2019 | Liu et al. |
| 2019/0276816 | A1 | 9/2019 | Liu et al. |
| 2019/0276873 | A1 | 9/2019 | Dong et al. |
| 2020/0071722 | A1 | 3/2020 | Liu et al. |
| 2020/0216833 | A1 | 7/2020 | Liu et al. |
| 2020/0255868 | A1 | 8/2020 | Liu et al. |
| 2020/0277587 | A1 | 9/2020 | Liu et al. |
| 2020/0323984 | A1 | 10/2020 | Liu et al. |
| 2021/0163924 | A1 | 6/2021 | Packer et al. |
| 2021/0238569 | A1 | 8/2021 | Liu et al. |
| 2021/0261938 | A1 | 8/2021 | Liu et al. |
| 2021/0403887 | A1 | 12/2021 | Liu et al. |
| 2022/0073887 | A1 | 3/2022 | Liu et al. |
| 2022/0154237 | A1 | 5/2022 | Liu et al. |
| 2022/0195418 | A1 | 6/2022 | Liu et al. |
| 2022/0259269 | A1 | 8/2022 | Liu et al. |
| 2022/0267754 | A1 | 8/2022 | Liu et al. |
| 2023/0220016 | A1 | 7/2023 | Liu et al. |
| 2024/0124863 | A1 | 4/2024 | Liu et al. |
| 2024/0200044 | A1 | 6/2024 | Liu et al. |
| 2024/0209338 | A1 | 6/2024 | Liu et al. |
| 2024/0271119 | A1 | 8/2024 | Liu et al. |
| 2024/0287491 | A1 | 8/2024 | Liu et al. |
| 2025/0195627 | A1 | 6/2025 | Liu et al. |

FOREIGN PATENT DOCUMENTS

| | | | |
|---|---|---|---|
| JP | H0937764 | A | 2/1997 |
| JP | 2011-081011 | A | 4/2011 |
| WO | WO 90/02809 | A1 | 3/1990 |
| WO | WO 91/17271 | A1 | 11/1991 |
| WO | WO 92/01047 | A1 | 1/1992 |
| WO | WO 92/09690 | A2 | 6/1992 |
| WO | WO 92/15679 | A1 | 9/1992 |
| WO | WO 92/18619 | A1 | 10/1992 |
| WO | WO 92/20791 | A1 | 11/1992 |
| WO | WO 93/01288 | A1 | 1/1993 |
| WO | WO 94/18316 | A2 | 8/1994 |
| WO | WO 96/04403 | A1 | 2/1996 |
| WO | WO 98/32845 | A1 | 7/1998 |
| WO | WO 99/23116 | A1 | 5/1999 |
| WO | WO 00/71694 | A1 | 11/2000 |
| WO | WO 01/05950 | A2 | 1/2001 |
| WO | WO 2001/038547 | A2 | 5/2001 |
| WO | WO 01/61049 | A1 | 8/2001 |
| WO | WO 2005/081632 | A2 | 9/2005 |
| WO | WO 2007/066923 | A1 | 6/2007 |
| WO | WO 2008/005529 | A2 | 1/2008 |
| WO | WO 2009/066964 | A1 | 5/2009 |
| WO | WO 2009/082488 | A2 | 7/2009 |
| WO | WO 2009/108180 | A2 | 9/2009 |
| WO | WO 2010/028347 | A2 | 3/2010 |
| WO | WO 2011/039518 | A2 | 4/2011 |
| WO | WO 2011/066747 | A1 | 6/2011 |
| WO | WO 2011/125015 | A2 | 10/2011 |
| WO | WO 2011/147590 | A2 | 12/2011 |
| WO | WO 2012/088381 | A2 | 6/2012 |
| WO | WO 2012/123370 | A1 | 9/2012 |
| WO | WO 2012/138927 | A2 | 10/2012 |
| WO | WO 2013/047844 | A1 | 4/2013 |
| WO | WO 2014/039585 | A2 | 3/2014 |
| WO | WO 2014/086494 | A1 | 6/2014 |
| WO | WO 2014/157820 | A1 | 10/2014 |
| WO | WO 2014/158593 | A1 | 10/2014 |
| WO | WO 2015/134121 | A2 | 9/2015 |
| WO | WO 2015/193897 | A1 | 12/2015 |
| WO | WO 2016/077052 | A2 | 5/2016 |
| WO | WO 2016/168631 | A1 | 10/2016 |
| WO | WO 2017/015559 | A2 | 1/2017 |
| WO | WO 2017/070632 | A2 | 4/2017 |
| WO | WO 2017/136792 | A2 | 8/2017 |
| WO | WO 2018/009903 | A2 | 1/2018 |
| WO | WO 2018/027078 | A1 | 2/2018 |
| WO | WO 2018/039438 | A1 | 3/2018 |
| WO | WO 2018/056002 | A1 | 3/2018 |
| WO | WO 2018/109447 | A1 | 6/2018 |
| WO | WO 2018/119042 | A1 | 6/2018 |
| WO | WO 2018/136939 | A1 | 7/2018 |
| WO | WO 2019/040935 | A1 | 2/2019 |
| WO | WO 2019/067815 | A2 | 4/2019 |
| WO | WO 2019/118362 | A1 | 6/2019 |
| WO | WO 2020/204836 | A1 | 10/2020 |

(56) References Cited

FOREIGN PATENT DOCUMENTS

| | | | |
|---|---|---|---|
| WO | WO 2020/252455 | A1 | 12/2020 |
| WO | WO 2021/011579 | A1 | 1/2021 |
| WO | Wo 2023/081805 | A1 | 5/2023 |
| WO | 2024/050007 | A1 | 3/2024 |

OTHER PUBLICATIONS

International Search Report and Written Opinion for Application No. PCT/US2021/064125, mailed Apr. 7, 2022.
International Preliminary Report on Patentability mailed Jun. 29, 2023, in connection with Application No. PCT/US2021/064125.
International Search Report and Written Opinion for Application No. PCT/US2022/074208, mailed Feb. 15, 2023.
International Search Report and Written Opinion for Application No. PCT/US2022/079281, mailed Feb. 23, 2023.
[No Author Listed] Genbank Submission. NCBI; Accession No. WP_010869888, version WP_010869888.1. tyrosine-tRNA ligase [Methanocaldococcus jannaschii]. Jun. 1, 2019.
[No Author Listed] NCBI Accession No. XP_015843220.1. C->U editing enzyme APOBEC-1 [Peromyscus maniculatus bairdii], XP002793540. Mar. 21, 2016.
[No Author Listed] NCBI Accession No. XP_021505673.1. C ->U editing enzyme APOBEC-1 [Meriones unguiculatus], XP002793541. Jun. 27, 2017.
Agarwal et al., Mode of VAMP substrate recognition and inhibition of Clostridium botulinum neurotoxin F. Nat Struct Mol Biol. Jul. 2009;16(7):789-94. doi: 10.1038/nsmb.1626. Epub Jun. 21, 2009.
Ahluwalia et al., Hypermutability and error catastrophe due to defects in ribonucleotide reductase. Proc Natl Acad Sci U S A. Nov. 12, 2013;110(46):18596-601. doi: 10.1073/pnas.1310849110. Epub Oct. 28, 2013.
Akopian et al., Chimeric recombinases with designed DNA sequence recognition. Proc Natl Acad Sci U S A. Jul. 2, 20032;100(15):8688-91. Epub Jul. 1, 2003.
Amiram et al., Evolution of translation machinery in recoded bacteria enables multi-site incorporation of nonstandard amino acids. Nat Biotechnol. Dec. 2015;33(12):1272-1279. doi: 10.1038/nbt.3372. Epub Nov. 16, 2015.
Armstrong et al., Chapter 3. Vectors for Phage Display. In: Phage Display of Peptides and Proteins. Kay et al., eds. Academic Press. San Diego, CA. 1996:35-53.
Bade et al., Botulinum neurotoxin type D enables cytosolic delivery of enzymatically active cargo proteins to neurones via unfolded translocation intermediates. J Neurochem. Dec. 2004;91(6):1461-72.
Badran et al., Continuous evolution of Bacillus thuringiensis toxins overcomes insect resistance. Nature. May 5, 2016;533(7601):58-63. doi: 10.1038/nature17938. Epub Apr. 27, 2016.
Badran et al., Development of potent in vivo mutagenesis plasmids with broad mutational spectra. Nat Commun. Oct. 7, 2015;6:8425. doi: 10.1038/ncomms9425.
Badran et al., In vivo continuous directed evolution. Curr Opin Chem Biol. Feb. 2015;24:1-10. doi: 10.1016/j.cbpa.2014.09.040. Epub Nov. 7, 2014.
Baker et al., Chemical complementation: a reaction-independent genetic assay for enzyme catalysis. Proc Natl Acad Sci U S A. Dec. 24, 2002;99(26):16537-42. Epub Dec. 13, 2002.
Barbas et al., Assembly of combinatorial antibody libraries on phage surfaces: the gene III site. Proc Natl Acad Sci U S A. Sep. 15, 1991;88(18):7978-82.
Bennet et al., Unlocking of the filamentous bacteriophage virion during infection is mediated by the C domain of pIII. J Mol Biol. Feb. 17, 2006;356(2):266-73. Epub Dec. 9, 2005.
Binz et al., Clostridial neurotoxins: mechanism of SNARE cleavage and outlook on potential substrate specificity reengineering. Toxins. Apr. 2010;2(4):665-82. Epub Apr. 13, 2010.
Birling et al., Site-specific recombinases for manipulation of the mouse genome. Methods Mol Biol. 2009;561:245-63. doi: 10.1007/978-1-60327-019-9_16.
Bloom et al., Evolving strategies for enzyme engineering. Curr Opin Struct Biol. Aug. 2005;15(4):447-52.
Blum et al., Phage-assisted evolution of botulinum neurotoxin proteases with reprogrammed specificity. Science. Feb. 19, 2021;371(6531):803-810. doi: 10.1126/science.abf5972.
Blum, Continuous evolution of bacterial neurotoxins for intracellular protease therapy. 2019. Poster. 1 page.
Blum, Generation of selective botulinum neurotoxin proteases with reprogrammed substrate specificity through phage-assisted directed evolution. Apr. 7, 2020. Powerpoint. 36 pages.
Blum, Generation of selective botulinum neurotoxin proteases with reprogrammed substrate specificity through phage-assisted directed evolution. Jun. 4, 2019. Powerpoint. 24 pages.
Boch et al., Breaking the code of DNA binding specificity of TAL-type III effectors. Science. Dec. 11, 2009;326(5959):1509-12. doi: 10.1126/science.1178811.
Boeke et al., Effects of bacteriophage f1 gene III protein on the host cell membrane. Mol Gen Genet. 1982;186(2):185-92.
Boersma et al., Selection strategies for improved biocatalysts. FEBS J. May 2007;274(9):2181-95.
Bolusani et al., Evolution of variants of yeast site-specific recombinase Flp that utilize native genomic sequences as recombination target sites. Nucleic Acids Res. 2006;34(18):5259-69. Epub Sep. 26, 2006.
Box et al., A multi-domain protein system based on the HC fragment of tetanus toxin for targeting DNA to neuronal cells. J Drug Target. Jul. 2003;11(6):333-43. doi: 10.1080/1061186310001634667.
Braun et al., Immunogenic duplex nucleic acids are nuclease resistant. J Immunol. Sep. 15, 1988;141(6):2084-9.
Breaker et al., Emergence of a replicating species from an in vitro RNA evolution reaction. Proc Natl Acad Sci U S A. Jun. 21, 1994;91(13):6093-7.
Brieba et al., Role of T7 RNA polymerase His784 in start site selection and initial transcription. Biochemistry. Apr. 23, 2002;41(16):5144-9.
Buchholz et al., Alteration of Cre recombinase site specificity by substrate-linked protein evolution. Nat Biotechnol. Nov. 2001;19(11):1047-52.
Burland et al., Analysis of the *Escherichia coli* genome VI: DNA sequence of the region from 92.8 through 100 minutes. Nucleic Acids Res. Jun. 25, 1995;23(12):2105-19. doi: 10.1093/nar/23.12.2105.
Cadwell et al., Randomization of Genes by PCR Mutagenesis. PCR Methods Applic. 1992;2:28-33.
Camps et al., Targeted gene evolution in *Escherichia coli* using a highly error-prone DNA polymerase I. Proc Natl Acad Sci U S A. Aug. 19, 2003;100(17):9727-32. Epub Aug. 8, 2003.
Canitrot et al., Overexpression of DNA polymerase beta in cell results in a mutator phenotype and a decreased sensitivity to anticancer drugs. Proc Natl Acad Sci U S A. Oct. 13, 1998;95(21):12586-90. doi: 10.1073/pnas.95.21.12586.
Cao et al., Characterization of the transgenic rice event TT51-1 and construction of a reference plasmid. J Agric Food Chem. Aug. 24, 2011;59(16):8550-9. doi: 10.1021/jf201699s. Epub Jul. 21, 2011.
Carlson et al., Negative selection and stringency modulation in phage-assisted continuous evolution. Nat Chem Biol. Mar. 2014;10(3):216-22. doi: 10.1038/nchembio.1453. Epub Feb. 2, 2014. With Supplementary Results.
Cattaneo et al., SELIL affects human pancreatic cancer cell cycle and invasiveness through modulation of PTEN and genes related to cell-matrix interactions. Neoplasia. 2005;7(11):1030-1038.
Chaddock et al., Inhibition of vesicular secretion in both neuronal and nonneuronal cells by a retargeted endopeptidase derivative of Clostridium botulinum neurotoxin type A. Infect. Immun. May 2000;68(5):2587-93.
Chaineau et al., Multiple roles of the vesicular-SNARE TI-VAMP in post-Golgi and endosomal trafficking. FEBS Letters. Oct. 2009;583:3817-26.
Chasteen et al., Eliminating helper phage from phage display. Nucleic Acids Res. 2006;34(21):e145. Epub Nov. 6, 2006.

(56) References Cited

OTHER PUBLICATIONS

Chaturvedi et al., Stabilization of triple-stranded oligonucleotide complexes: use of probes containing alternating phosphodiester and stereo-uniform cationic phosphoramidate linkages. Nucleic Acids Res. Jun. 15, 1996;24(12):2318-23.
Cheetham et al., Structural basis for initiation of transcription from an RNA polymerase-promoter complex. Nature. May 6, 1999;399(6731):80-3.
Chen et al., Engineering botulinum neurotoxin to extend therapeutic intervention. PNAS. Jun. 2009;106(23):9180-4.
Chen et al., Information theory based T7-like promoter models: classification of bacteriophages and differential evolution of promoters and their polymerases. Nucleic Acids Res. Oct. 31, 2005;33(19):6172-87. Print 2005.
Chen et al., Mechanism of substrate recognition by botulinum neurotoxin serotype A. J Biol Chem. Mar. 30, 2007;282(13):9621-9627. doi: 10.1074/jbc.M611211200. Epub Jan. 23, 2007.
Chen et al., Multiple pocket recognition of SNAP25 by botulinum neurotoxin serotype E. J Biol Chem. Aug. 31, 2007;282(35):25540-7. doi: 10.1074/jbc.M701922200. Epub Jul. 3, 2007.
Chen et al., SNARE-mediated membrane fusion. Nat Rev Mol Cell Biol. Feb. 2001;2(2):98-106.
Chen et al., VAMP8 facilitates cellular proliferation and temozolomide resistance in human glioma cells. Neuro-Oncology. 2015; 17(3):407-18. Epub Sep. 10, 2014.
Chen, Clinical uses of botulinum neurotoxins: current indications, limitations and future developments. Toxins (Basel). 2012;4(10):913-939.
Chin, Expanding and reprogramming the genetic code of cells and animals. Annu Rev Biochem. 2014;83:379-408. doi: 10.1146/annurev-biochem-060713-035737. Epub Feb. 10, 2014.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Clackson et al., Making antibody fragments using phage display libraries. Nature. Aug. 15, 1991;352(6336):624-8.
Click et al., Filamentous phage infection: required interactions with the TolA protein. J Bacteriol. Oct. 1997;179(20):6464-71.
Cobb et al., Directed evolution: an evolving and enabling synthetic biology tool. Curr Opin Chem Biol. Aug. 2012;16(3-4):285-91. doi: 10.1016/j.cbpa.2012.05.186. Epub Jun. 4, 2012.
Cong et al., Multiplex genome engineering using CRISPR/Cas systems. Science. 2013; 339:819-23.
Corey et al., Trypsin display on the surface of bacteriophage. Gene. Jun. 15, 1993;128(1):129-34.
Craik et al., Proteases as therapeutics. Biochem J. Apr. 2011;435(1):16 pages.
Crameri et al., Display of biologically active proteins on the surface of filamentous phages: a cDNA cloning system for selection of functional gene products linked to the genetic information responsible for their production. Gene. Dec. 27, 1993;137(1):69-75.
Cwirla et al., Peptides on phage: a vast library of peptides for identifying ligands. Proc Natl Acad Sci U S A. Aug. 1990;87(16):6378-82.
Das et al., Viral evolution as a tool to improve the tetracycline-regulated gene expression system. J Biol Chem. Apr. 30, 2004;279(18):18776-82. Epub Feb. 2, 2004.
Datsenko et al., One-step inactivation of chromosomal genes in *Escherichia coli* K-12 using PCR products. Proc Natl Acad Sci U S A. Jun. 6, 2000;97(12):6640-5.
Davis et al., Viral mutagenesis as a means for generating novel proteins. J Virol. Feb. 2010;84(3):1625-30. Epub Nov. 11, 2009.
De Haard et al., A large non-immunized human Fab fragment phage library that permits rapid isolation and kinetic analysis of high affinity antibodies. J Biol Chem. Jun. 25, 1999;274(26):18218-30.
Deltcheva et al., CRISPR RNA maturation by trans-encoded small RNA and host factor RNase III. Nature. Mar. 31, 2011;471(7340):602-7. doi: 10.1038/nature09886.
Deribe, Mechanistic insights into the role of truncating PREX2 mutations in melanoma. Mol Cell Oncol. 2016;3(3):e1160174.
Deussing, Targeted mutagenesis tools for modelling psychiatric disorders. Cell Tissue Res. Oct. 2013;354(1):9-25. doi: 10.1007/s00441-013-1708-5. Epub Sep. 10, 2013.
DiCarlo et al., Genome engineering in Saccharomyces cerevisiae using CRISPR-Cas systems. Nucleic Acids Res. Apr. 2013;41(7):4336-43. doi: 10.1093/nar/gkt135. Epub Mar. 4, 2013.
Dickinson et al., A system for the continuous directed evolution of proteases rapidly reveals drug-resistance mutations. Nat Commun. Oct. 30, 2014;5:5352. doi: 10.1038/ncomms6352.
Dickinson et al., Experimental interrogation of the path dependence and stochasticity of protein evolution using phage-assisted continuous evolution. Proc Natl Acad Sci USA. May 2013;110(22):9007-12.
Dong et al., Using fluorescent sensors to detect botulinum neurotoxin activity in vitro and in living cells. Proc Natl Acad Sci U S A. Oct. 12, 2004;101(41):14701-6. doi: 10.1073/pnas.0404107101. Epub Oct. 1, 2004.
Dove et al., Conversion of the omega subunit of *Escherichia coli* RNA polymerase into a transcriptional activator or an activation target. Genes Dev. Mar. 1, 1998;12(5):745-54.
Doyon et al., Directed evolution and substrate specificity profile of homing endonuclease I-SceI. J Am Chem Soc. Feb. 22, 2006;128(7):2477-84.
Drake, A constant rate of spontaneous mutation in DNA-based microbes. Proc Natl Acad Sci USA. Aug. 15, 1991;88(16):7160-4.
Duggan et al., Inhibition of Release of Neurotransmitters from Rat Dorsal Root Ganglia by a Novel Conjugate of a Clostridium botulinum Toxin A Endopeptidase Fragment and Erythrina cristagalli Lectin. The Journal of Biological Chemistry. Sep. 2002;277(38):34846-52.
Durai et al., A bacterial one-hybrid selection system for interrogating zinc finger-DNA interactions. Comb Chem High Throughput Screen. May 2006;9(4):301-11.
Durniak et al., The structure of a transcribing T7 RNA polymerase in transition from initiation to elongation. Science. Oct. 24, 2008;322(5901):553-7.
Esvelt et al., A system for the continuous directed evolution of biomolecules. Nature. Apr. 28, 2011;472(7344):499-503. doi: 10.1038/nature09929. Epub Apr. 10, 2011.
Esvelt et al., A system for the continuous directed evolution of biomolecules. Nature. Apr. 28, 2011;472(7344):499-503. Epub Apr. 10, 2011.
Fan et al., Rationally evolving tRNAPyl for efficient incorporation of noncanonical amino acids. Nucleic Acids Res. Dec. 15, 2015;43(22):e156. doi: 10.1093/nar/gkv800. Epub Aug. 6, 2015.
Feng et al., Exo1: A new chemical inhibitor of the exocytic pathway. PNAS. May 2003;100(11):6469-74.
Ferretti et al., Complete genome sequence of an M1 strain of *Streptococcus pyogenes*. Proc Natl Acad Sci U S A. Apr. 10, 2001;98(8):4658-63. doi: 10.1073/pnas.071559398.
Fijalkowska et al., Mutants in the Exo I motif of *Escherichia coli* dnaQ: defective proofreading and inviability due to error catastrophe. Proc Natl Acad Sci U S A. Apr. 2, 1996;93(7):2856-61.
Foster et al., Re-engineering the target specificity of Clostridial neurotoxins—A route to novel therapeutics. Neurotoxicity Research. May 2006;9(2,3):101-7.
Foster et al., Targeted Secretion Inhibitors—Innovative Protein Therapeutics. Toxins. Dec. 2010;2:2795-815.
Fowlkes et al., Multipurpose vectors for peptide expression on the M13 viral surface. Biotechniques. Sep. 1992;13(3):422-8.
Friedberg et al., Error-prone DNA polymerases: novel structures and the benefits of infidelity. Cell. Oct. 5, 2001;107(1):9-12.
Fu et al., Promises and Pitfalls of Intracellular Delivery of Proteins. Bioconjugate Chemistry. Aug. 2014;25:1602-8.
Fuchs et al., Targeting Recombinant Antibodies to the Surface of *Escherichia coli*: Fusion to a Peptidoglycan Associated Lipoprotein. Bio/Technology. 1991;9:1370-72.
Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.
Garrard et al., Fab assembly and enrichment in a monovalent phage display system. Biotechnology (N Y). Dec. 1991;9(12):1373-7.

(56) References Cited

OTHER PUBLICATIONS

Genbank Submission. NCBI; Accession No. WP_011033391, version WP_011033391.1. pyrrolysine-tRNA(Pyl) ligase [Methanosarcina mazei]. Polycarpo et al.; Nov. 29, 2019.
Genbank Submission. NCBI; Accession No. WP_011305865, version WP_011305865.1. pyrrolysine-tRNA(Pyl) ligase [Methanosarcina barkeri].Polycarpo et al.; Nov. 29, 2019.
Gibson et al., Enzymatic assembly of DNA molecules up to several hundred kilobases. Nat Methods. May 2009;6(5):343-5. Epub Apr. 12, 2009.
Gill, Bacterial Toxins: a Table of Letal Amounts. Microbiological Reviews. Mar. 1982;46(1):86-94.
Goodnough et al., Development of a delivery vehicle for intracellular transport of botulinum neurotoxin antagonists. FEBS Lett. Feb. 27, 2002;513(2-3):163-8.
Gordley et al., Evolution of programmable zinc finger-recombinases with activity in human cells. J Mol Biol. Mar. 30, 2007;367(3):802-13. Epub Jan. 12, 2007.
Gram et al., In vitro selection and affinity maturation of antibodies from a naive combinatorial immunoglobulin library. Proc Natl Acad Sci U S A. Apr. 15, 1992;89(8):3576-80.
Griffiths et al., Human anti-self antibodies with high specificity from phage display libraries. EMBO J. Feb. 1993; 12(2):725-34.
Guilinger et al., Broad specificity profiling of TALENs results in engineered nucleases with improved DNA-cleavage specificity. Nat Methods. Apr. 2014;11(4):429-35. doi: 10.1038/nmeth.2845. Epub Feb. 16, 2014.
Guilinger et al., Fusion of catalytically inactive Cas9 to FokI nuclease improves the specificity of genome modification. Nat. Biotechnol. 2014; 32(6): 577-82. doi: 10.1038/nbt.2909. Epub Apr. 25, 2014.
Guo et al., Evolution of amber suppressor tRNAs for efficient bacterial production of proteins containing nonnatural amino acids. Angew Chem Int Ed Engl. 2009;48(48):9148-51. doi: 10.1002/anie.200904035.
Guo et al., Polyspecific pyrrolysyl-tRNA synthetases from directed evolution. Proc Natl Acad Sci U S A. Nov. 25, 2014;111(47):16724-9. doi: 10.1073/pnas.1419737111. Epub Nov. 10, 2014.
Guzman et al., Tight regulation, modulation, and high-level expression by vectors containing the arabinose PBAD promoter. J Bacteriol. 1995;177(14):4121-4130.
Harris et al., Measurement of enzyme activity. Methods Enzymol. 2009;463:57-71.
Hart et al., Directed Evolution to Investigate Steric Control of Enzymatic Oxidosqualene Cyclization. An Isoleucine-to-Valine Mutation in Cycloartenol Synthase Allows Lanosterol and Parkeol Biosynthesis. J Am Chem Soc. 1999;121:9887-88.
Hawkins et al., Selection of phage antibodies by binding affinity. Mimicking affinity maturation. J Mol Biol. Aug. 5, 1992;226(3):889-96.
Hay et al., Bacteriophage cloning and *Escherichia coli* expression of a human IgM Fab. Hum Antibodies Hybridomas. Apr. 1992;3(2):81-5.
Hedstrom et al., Converting trypsin to chymotrypsin: the role of surface loops. Science. Mar. 1992;255(5049):1249-53.
Hendricks et al., The S. cerevisiae Mag1 3-methyladenine DNA glycosylase modulates susceptibility to homologous recombination. DNA Repair (Amst). 2002;1(8):645-659.
Herring et al., The amino-terminal domain of pyrrolysyl-tRNA synthetase is dispensable in vitro but required for in vivo activity. FEBS Lett. Jul. 10, 2007;581(17):3197-203. doi: 10.1016/j.febslet.2007.06.004. Epub Jun. 12, 2007.
Ho et al., Recombinant botulinum neurotoxin A heavy chainbased delivery vehicles for neuronal cell targeting. Protein Engineering, Design & Selection. 2011;24(3):247-53. Epub Nov. 4, 2010.
Hoogenboom et al., Antibody phage display technology and its applications. Immunotechnology. Jun. 1998;4(1):1-20.
Hoogenboom et al., Multi-subunit proteins on the surface of filamentous phage: methodologies for displaying antibody (Fab) heavy and light chains. Nucleic Acids Res. Aug. 11, 1991;19(15):4133-7.
Hoogenboom et al., Natural and designer binding sites made by phage display technology. Immunol Today. Aug. 2000;21(8):371-8.
Houshmand et al., Use of Bateriophage T7 Displayed Peptides for Determination of Monoclonal Anitbody Specificity and Biosensor Analysis of the Binding Reaction. Anal Biochem. 1999;268:363-70.
Hu et al., *Escherichia coli* one- and two-hybrid systems for the analysis and identification of protein-protein interactions. Methods. Jan. 2000;20(1):80-94.
Hubbard et al., Continuous directed evolution of DNA-binding proteins to improve TALEN specificity. Nat Methods. Oct. 2015;12(10):939-42. doi: 10.1038/nmeth.3515. Epub Aug. 10, 2015. With Supplementary Information.
Huse et al., Generation of a large combinatorial library of the immunoglobulin repertoire in phage lambda. Science. Dec. 8, 1989;246(4935):1275-81.
Husimi et al., Cellstat—a continuous culture system of a bacteriophage for the study of the mutation rate and the selection process of the DNA level. Rev Sci Instrum. Apr. 1982;53(4):517-22.
Husimi, Selection and evolution of bacteriophages in cellstat. Adv Biophys. 1989;25:1-43.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
Ichetovkin et al., Substrate recognition by the leucyl/phenylalanyl-tRNA-protein transferase. Conservation within the enzyme family and localization to the trypsin-resistant domain. J Biol Chem. Dec. 26, 1997;272(52):33009-14.
Ikeda et al., In vivo and in vitro activities of point mutants of the bacteriophage T7 RNA polymerase promoter. Biochemistry. Sep. 22, 1992;31(37):9073-80.
Ikeda et al., Selection and characterization of a mutant T7 RNA polymerase that recognizes an expanded range of T7 promoter-like sequences. Biochemistry. Sep. 7, 1993;32(35):9115-24.
Imburgio et al., Studies of promoter recognition and start site selection by T7 RNA polymerase using a comprehensive collection of promoter variants. Biochemistry. Aug. 29, 2000;39(34):10419-30.
Irion et al., Identification and targeting of the ROSA26 locus in human embryonic stem cells. Nat Biotechnol. Dec. 2007;25(12):1477-82. Epub Nov. 25, 2007.
Jankovic et al., Direct selection and phage display of a Gram-positive secretome. Genome Biology. Dec. 13, 2007; 8(266):1-15.
Jiang et al., PylSn and the homologous N-terminal domain of pyrrolysyl-tRNA synthetase bind the tRNA that is essential for the genetic encoding of pyrrolysine. J Biol Chem. Sep. 21, 2012;287(39):32738-46. doi: 10.1074/jbc.M112.396754. Epub Jul. 31, 2012.
Jiang et al., RNA guided editing of bacterial genomes using CRISPR-Cas systems. Nat Biotechnol. Mar. 2013;31(3):233-9. doi: 10.1038/nbt.2508. Epub Jan. 29, 2013.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Jinek et al., RNA-programmed genome editing in human cells. Elife. Jan. 29, 2013;2:e00471. doi: 10.7554/eLife.00471.
Johns et al., The promise and peril of continuous in vitro evolution. J Mol Evol. Aug. 2005;61(2):253-63. Epub Jun. 27, 2005.
Joho et al., Identification of a region of the bacteriophage T3 and T7 RNA polymerases that determines promoter specificity. J Mol Biol. Sep. 5, 1990;215(1):31-9.
Jones et al., Phage-Assisted Continuous Evolution and Selection of Enzymes for Chemical Synthesis. ACS Cent Sci. Sep. 22, 2021;7(9):1581-1590. doi: 10.1021/acscentsci.1c00811. Epub Sep. 13, 2021.
Joung et al., A bacterial two-hybrid selection system for studying protein-DNA and protein-protein interactions. Proc Natl Acad Sci U S A. Jun. 20, 2000;97(13):7382-7.
Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.

(56) References Cited

OTHER PUBLICATIONS

Kasai et al., Distinct initial SNARE configurations underlying the diversity of exocytosis. Physiol Rev. Oct. 2012;92(4):1915-64. doi: 10.1152/physrev.00007.2012.
Kavran et al., Structure of pyrrolysyl-tRNA synthetase, an archaeal enzyme for genetic code innovation. Proc Natl Acad Sci U S A. Jul. 3, 2007;104(27):11268-73. doi: 10.1073/pnas.0704769104. Epub Jun. 25, 2007.
Kawarasaki et al., Enhanced crossover SCRATCHY: construction and high-throughput screening of a combinatorial library containing multiple non-homologous crossovers. Nucleic Acids Res. Nov. 1, 2003;31(21):e126.
Khlebnikov et al., Modulation of gene expression from the arabinose-inducible araBAD promoter. J Ind Microbiol Biotechnol. Jul. 2002;29(1):34-7.
Kim et al., DJ-1, a novel regulator of the tumor suppressor PTEN. Cancer Cell. 2005;7(3):263-273.
Kim et al., Increasing the genome-targeting scope and precision of base editing with engineered Cas9-cytidine deaminase fusions. Nature Biotechnology; Feb. 13, 2007; 35(4): 371-376.
Klement et al., Discrimination between bacteriophage T3 and T7 promoters by the T3 and T7 RNA polymerases depends primarily upon a three base-pair region located 10 to 12 base-pairs upstream from the start site. J Mol Biol. Sep. 5, 1990;215(1):21-9.
Köhler, A yeast-based growth assay for the analysis of site-specific proteases. Nucleic Acids Res. 2003;31(4):e16. 5 pages.
Komor et al., Programmable editing of a target base in genomic DNA without double-stranded DNA cleavage. Nature. May 19, 2016;533(7603):420-4. doi: 10.1038/nature17946. Epub Apr. 20, 2016.
Kozak et al., Structural features in eukaryotic mRNAs that modulate the initiation of translation. J Biol Chem. Oct. 25, 1991;266(30):19867-70.
Kuzmine et al., Binding of the priming nucleotide in the initiation of transcription by T7 RNA polymerase. J Biol Chem. Jan. 31, 2003;278(5):2819-23. Epub Nov. 9, 2002.
Laskowska et al., IbpA and IbpB, the new heat-shock proteins, bind to endogenous *Escherichia coli* proteins aggregated intracellularly by heat shock. Biochimie. 1996;78(2):117-22.
Latimer et al., Specificity of monoclonal antibodies produced against phosphorothioate and ribo modified DNAs. Mol Immunol. Oct. 1995;32(14-15):1057-64.
Lebeda et al., The Zinc-Dependent Protease Activity of the Botulinum Neurotoxins. Toxins. May 2010;2:978-97.
Leconte et al., A population-based experimental model for protein evolution: effects of mutation rate and selection stringency on evolutionary outcomes. Biochemistry. Feb. 26, 2013; 52(8): 1490-1499.
Lee et al., Enhanced production of human full-length immunoglobulin G1 in the periplasm of *Escherichia coli*. Appl Microbiol Biotechnol. Feb. 2014;98(3):1237-46. doi: 10.1007/s00253-013-5390-z. Epub Nov. 26, 2013.
Lei et al., Efficient targeted gene disruption in Xenopus embryos using engineered transcription activator-like effector nucleases (TALENs). PNAS Oct. 23, 2012; 109(43):17484-17489; https://doi.org/10.1073/pnas.1215421109.
Lincoln et al., Self-sustained replication of an RNA enzyme. Science. Feb. 27, 2009;323(5918):1229-32. Epub Jan. 8, 2009.
Lindemann et al., Evolution of bacteriophage in continuous culture: a model system to test antiviral gene therapies for the emergence of phage escape mutants. J Virol. Jun. 2002;76(11):5784-92.
Liu et al., Adding new chemistries to the genetic code. Annu Rev Biochem. 2010;79:413-44. doi: 10.1146/annurev.biochem.052308.105824.
Liu et al., PTEN deletion enhances the regenerative ability of adult corticospinal neurons. Nat Neurosci. Sep. 2010;13(9):1075-81. doi: 10.1038/nn.2603. Epub Aug. 8, 2010.
Lu, The destructive effect of botulinum neurotoxins on the SNARE protein: SNAP-25 and synaptic membrane fusion. PeerJ. 2015;3:e1065. Published Jun. 30, 2015.
Lundquist et al., Site-directed mutagenesis and characterization of uracil-DNA glycosylase inhibitor protein. Role of specific carboxylic amino acids in complex formation with *Escherichia coli* uracil-DNA glycosylase. J Biol Chem. Aug. 22, 1997;272(34):21408-19. doi: 10.1074/jbc.272.34.21408.
Lutz et al., Creating multiple-crossover DNA libraries independent of sequence identity. Proc Natl Acad Sci U S A. Sep. 2, 20015;98(20):11248-53. Epub Sep. 18, 2001.
Maeder et al., Robust, synergistic regulation of human gene expression using TALE activators. Nat Methods. Mar. 2013;10(3):243-5. doi: 10.1038/nmeth.2366. Epub Feb. 10, 2013.
Makeyev et al., Evolutionary potential of an RNA virus. J Virol. Feb. 2004;78(4):2114-20.
Mali et al., RNA-guided human genome engineering via Cas9. Science. 2013; 339:823-26.
Malmborg et al., Selective phage infection mediated by epitope expression on F pilus. J Mol Biol. Oct. 31, 1997;273(3):544-51.
Manta et al., Disulfide Bond Formation in the Periplasm of *Escherichia coli*. EcoSal Plus. Feb. 2019;8(2). doi: 10.1128/ecosalplus.ESP-0012-2018.
Marcet-Palacios et al., Vesicle-associated membrane protein 7 (VAMP-7) is essential for target cell killing in a natural killer cell line. Biochem Biophys Res Commun. Feb. 15, 2008;366(3):617-23. doi: 10.1016/j.bbrc.2007.11.079. Epub Nov. 26, 2007.
Martin et al., Kinetic analysis of T7 RNA polymerase-promoter interactions with small synthetic promoters. Biochemistry. May 19, 1987;26(10):2690-6.
Masuyer et al., Engineered botulinum neurotoxins as new therapeutics. Annu Rev Pharmacol Toxicol. 2014;54:27-51.
McCafferty et al., Phage antibodies: filamentous phage displaying antibody variable domains. Nature. Dec. 6, 1990;348(6301):552-4.
McConnell et al., Constrained peptide libraries as a tool for finding mimotopes. Gene. Dec. 30, 1994;151(1-2):115-8.
McNaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.
Meng et al., Role of SNARE proteins in tumourigenesis and their potential as targets for novel anti-cancer therapeutics. Biochim Biophys Acta. Aug. 2015;1856(1):1-12. doi: 10.1016/j.bbcan.2015.04.002. Epub May 5, 2015.
Mihai et al., PTEN inhibition improves wound healing in lung epithelia through changes in cellular mechanics that enhance migration. Am J Physiol Lung Cell Mol Physiol. 2012;302(3):L287-L299.
Miller et al., A Tale nuclease architecture for efficient genome editing. Nat Biotechnol. Feb. 2011;29(2):143-8. doi:10.1038/nbt.1755. Epub Dec. 22, 2010.
Milligan et al., Oligoribonucleotide synthesis using T7 RNA polymerase and synthetic DNA templates. Nucleic Acids Res. Nov. 11, 1987;15(21):8783-98.
Mills et al., An extracellular Darwinian experiment with a self-duplicating nucleic acid molecule. Proc Natl Acad Sci U S A. Jul. 1967;58(1):217-24.
Morrison et al., Disulfide-compatible phage-assisted continuous evolution in the periplasmic space. Nat Commun. Oct. 13, 2021;12(1):5959. doi: 10.1038/s41467-021-26279-8.
Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.
Nelson et al., Filamentous phage DNA cloning vectors: a noninfective mutant with a nonpolar deletion in gene III. Virology. Jan. 30, 1981;108(2):338-50.
Nern et al., Multiple new site-specific recombinases for use in manipulating animal genomes. Proc Natl Acad Sci U S A. Aug. 23, 2011;108(34):14198-203. doi: 10.1073/pnas.1111704108. Epub Aug. 9, 2011.
Ngo et al., Computational Complexity, Protein Structure Prediction, and the Levinthal Paradox in the Protein Folding Problem and Tertiary Structure Prediction. Merz et al., Eds. 1994. pp. 433 and 492-495.
Nicholson-Fish et al., VAMP4 is an Essential Cargo Molecule for Activity-Dependent Bulk Endocytosis. Neuron. Dec. 2, 2015;88(5):973-984. doi: 10.1016/j.neuron.2015.10.043. Epub Nov. 19, 2015.

(56) References Cited

OTHER PUBLICATIONS

Nozawa et al., Pyrrolysyl-tRNA synthetase-tRNA(Pyl) structure reveals the molecular basis of orthogonality. Nature. Feb. 26, 2009;457(7233):1163-7. doi: 10.1038/nature07611. Epub Dec. 31, 2008.

O'Maille et al., Structure-based combinatorial protein engineering (Scope). J Mol Biol. Aug. 23, 2002;321(4):677-91.

O'Donoghue et al., Upgrading protein synthesis for synthetic biology. Nat Chem Biol. Oct. 2013;9(10):594-8. doi: 10.1038/nchembio.1339.

Oeemig et al., Solution structure of DnaE intein from Nostoc punctiforme: structural basis for the design of a new split intein suitable for site-specific chemical modification. FEBS Lett. May 6, 2009;583(9):1451-6.

Opperman et al., A model for a umuDC-dependent prokaryotic DNA damage checkpoint. Proc Natl Acad Sci U S A. Aug. 3, 1999;96(16):9218-23.

Ostendorf et al., Characterization of a dam mutant of Serratia marcescens and nucleotide sequence of the dam region. J Bacteriol. Jul. 1999; 181(13):3880-5.

Ostermeier et al., A combinatorial approach to hybrid enzymes independent of DNA homology. Nat Biotechnol. Dec. 1999;17(12):1205-9.

Peyrottes et al., Oligodeoxynucleoside phosphoramidates (P-NH2): synthesis and thermal stability of duplexes with DNA and RNA targets. Nucleic Acids Res. May 15, 1996;24(10):1841-8.

Pickett et al., Towards New Uses of Botulinum Toxin as a Novel Therapeutic Tool. Toxins. Jan. 2011;3:63-81.

Pogson et al., Engineering Next Generation Proteases. Curr Opin Biotechnol. Aug. 2009;20(4):390-7.

Popa et al., Phage-Assisted Continuous Evolution (PACE): A Guide Focused on Evolving Protein-DNA Interactions. ACS Omega. Oct. 16, 2020;5(42):26957-26966. doi: 10.1021/acsomega.0c03508. eCollection Oct. 27, 2020.

Pu et al., Evolution of a split RNA polymerase as a versatile biosensor platform. Nat Chem Biol. Apr. 2017;13(4):432-438. doi: 10.1038/nchembio.2299. Epub Feb. 13, 2017.

Putnam et al., Protein mimicry of DNA from crystal structures of the uracil-DNA glycosylase inhibitor protein and its complex with *Escherichia coli* uracil-DNA glycosylase. J Mol Biol. Mar. 26, 1999;287(2):331-46. doi: 10.1006/jmbi.1999.2605.

Radany et al., Increased spontaneous mutation frequency in human cells expressing the phage PBS2-encoded inhibitor of uracil-DNA glycosylase. Mutat Res. Sep. 15, 2000;461(1):41-58. doi: 10.1016/s0921-8777(00)00040-9.

Raingo et al., VAMP4 directs synaptic vesicles to a pool that selectively maintains asynchronous neurotransmission. Nat Neurosci. Mar. 11, 2012;15(5):738-45. doi: 10.1038/nn.3067.

Rakonjac et al., Filamentous phage are released from the bacterial membrane by a two-step mechanism involving a short C-terminal fragment of pIII. J Mol Biol. Jun. 25, 1999;289(5):1253-65.

Rakonjac et al., Filamentous phage infection-mediated gene expression: construction and propagation of the gIII deletion mutant helper phage R408d3. Gene. Oct. 1, 1997;198(1-2):99-103.

Rakonjac et al., Roles of pIII in filamentous phage assembly. J Mol Biol. Sep. 11, 1998;282(1):25-41.

Raskin et al., Substitution of a single bacteriophage T3 residue in bacteriophage T7 RNA polymerase at position 748 results in a switch in promoter specificity. J Mol Biol. Nov. 20, 1992;228(2):506-15.

Raskin et al., T7 RNA polymerase mutants with altered promoter specificities. Proc Natl Acad Sci U S A. Apr. 15, 1993;90(8):3147-51.

Rawlings et al., MEROPS: the database of proteolytic enzymes, their substrates and inhibitors. Nucleic Acids Res. Jan. 2014;42(Database issue):D503-9.

Rebar et al., Phage display methods for selecting zinc finger proteins with novel DNA-binding specificities. Methods Enzymol. 1996;267:129-49.

Reidhaar-Olson et al., Random mutagenesis of protein sequences using oligonucleotide cassettes. Methods Enzymol. 1991;208:564-86.

Reuven et al., Lesion bypass by the *Escherichia coli* DNA polymerase V requires assembly of a RecA nucleoprotein filament. J Biol Chem. Feb. 23, 2001;276(8):5511-7. Epub Nov. 17, 2000.

Riechmann et al., The C-terminal domain of TolA is the coreceptor for filamentous phage infection of *E. coli*. Cell. Jul. 25, 1997;90(2):351-60.

Ringquist et al., Translation initiation in *Escherichia coli*: sequences within the ribosome-binding site. Mol Microbiol. May 1992;6(9):1219-29.

Rosenberg et al., T7 Select® Phage Display System: A Powerful new protein display system based on bacteriophage T7. Innovations. 1996;6:1-6.

Rossetto et al., Botulinum neurotoxins: genetic, structural and mechanistic insights. Nat Rev Microbiol. Aug. 2014;12(8):535-49. doi: 10.1038/nrmicro3295. Epub Jun. 30, 2014.

Ruiz-Martinez et al., YKT6 expression, exosome release, and survival in non-small cell lung cancer. Oncotarget. Aug. 9, 2016;7(32):51515-51524. doi: 10.18632/oncotarget.9862.

Santini et al., Efficient display of an HCV cDNA expression library as C-terminal fusion to the capsid protein D of bacteriophage lambda. J Mol Biol. Sep. 11, 1998;282(1):125-35.

Santoro et al., Directed evolution of the site specificity of Cre recombinase. Proc Natl Acad Sci U S A. Apr. 2, 2002;99(7):4185-90. Epub Mar. 19, 2002.

Schultz et al., Oligo-2'-fluoro-2'-deoxynucleotide N3'-->P5' phosphoramidates: synthesis and properties. Nucleic Acids Res. Aug. 1, 1996;24(15):2966-73.

Scott et al., Searching for peptide ligands with an epitope library. Science. Jul. 27, 1990;249(4967):386-90.

Sices et al., A genetic screen for the isolation and characterization of site-specific proteases. Proc Natl Acad Sci U S A. Mar. 17, 1998;95(6):2828-33.

Sices et al., Rapid genetic selection of inhibitor-resistant protease mutants: clinically relevant and novel mutants of the HIV protease. AIDS Res Hum Retroviruses. Sep. 1, 2001;17(13):1249-55.

Sieber et al., Libraries of hybrid proteins from distantly related sequences. Nat Biotechnol. May 2001;19(5):456-60.

Sikorra et al., Identification and Characterization of Botulinum Neurotoxin A Substrate Binding Pockets and Their Re-Engineering for Human SNAP-23. J Mol Biol. Jan. 29, 2016;428(2 Pt A):372-384. doi: 10.1016/j.jmb.2015.10.024. Epub Oct. 30, 2015.

Sikorra et al., Identification of the amino acid residues rendering TI-VAMP insensitive toward botulinum neurotoxin B. J Mol Biol. Mar. 24, 2006;357(2):574-82. doi: 10.1016/j.jmb.2005.12.075. Epub Jan. 18, 2006.

Sikorra et al., Substrate Recognition Mechanism of VAMP/Synaptobrevin-cleaving Clostridial Neurotoxins. Journal of Biological Chemistry. 2008;283:21145-52. Epub May 29, 2008.

Silva et al., Selective disruption of the DNA polymerase III α-β complex by the umuD gene products. Nucleic Acids Res. Jul. 2012;40(12):5511-22. doi: 10.1093/nar/gks229. Epub Mar. 9, 2012.

Smith, Filamentous fusion phage: novel expression vectors that display cloned antigens on the virion surface. Science. Jun. 14, 1985;228(4705):1315-7.

Somm et al., A botulinum toxin-drived targeted secretion inihibitor downregulates the GH/IGF1 axis. The Journal of Clinical Investigation. Sep. 2012;122(9):3295-306.

Steffen et al., MT1-MMP-Dependent Invasion is Regulated by TI-VAMP/VAMP7. Current Biology. Jun. 2008;18:926-31.

Stemmer, Rapid evolution of a protein in vitro by DNA shuffling. Nature. Aug. 4, 1994;370(6488):389-91.

Sutter et al., Non-replicating vaccinia vector efficiently expresses bacteriophage T7 RNA polymerase. FEBS Lett. Aug. 28, 1995;371(1):9-12.

Torres et al., Non-integrative lentivirus drives high-frequency cre-mediated cassette exchange in human cells. PLOS One. 2011;6(5):e19794. doi: 10.1371/journal.pone.0019794. Epub May 23, 2011.

(56) References Cited

OTHER PUBLICATIONS

Tracewell et al., Directed enzyme evolution: climbing fitness peaks one amino acid at a time. Curr Opin Chem Biol. Feb. 2009;13(1):3-9. doi: 10.1016/j.cbpa.2009.01.017. Epub Feb. 25, 2009.

Tsai et al., Targeting botulinum neurotoxin persistence by the ubiquitin-proteasome system. PNAS. Sep. 2010;107(38):16554-9.

Tsuji et al., Random multi-recombinant PCR for the construction of combinatorial protein libraries. Nucleic Acids Res. Oct. 15, 2001;29(20):E97.

Turner et al., Structural plasticity of an aminoacyl-tRNA synthetase active site. Proc Natl Acad Sci U S A. Apr. 25, 2006;103(17):6483-8. doi: 10.1073/pnas.0601756103. Epub Apr. 17, 2006.

Tzagoloff et al., The Initial Steps In Infection With Coliphage M13. Virology. Nov. 1964;24:372-80.

Umehara et al., N-acetyl lysyl-tRNA synthetases evolved by a CcdB-based selection possess N-acetyl lysine specificity in vitro and in vivo. FEBS Lett. Mar. 23, 2012;586(6):729-33. doi: 10.1016/j.febslet.2012.01.029. Epub Jan. 28, 2012.

Varadarajan et al., Engineering of protease variants exhibiting high catalytic activity and exquisite substrate selectivity. PNAS. May 2005;102(19):6855-60.

Varadarajan et al., Highly active and selective endopeptidases with programmed substrate specificities. Nat Chem Biol. May 2008;4(5):290-4.

Vidal et al., Yeast forward and reverse 'n'-hybrid systems. Nucleic Acids Res. Feb. 15, 1999;27(4):919-29.

Vidal-Aroca et al., One-step high-throughput assay for quantitative detection of beta-galactosidase activity in intact gram-negative bacteria, yeast, and mammalian cells. Biotechniques. Apr. 2006;40(4):433-4, 436, 438 passim.

Vincenzeti et al., Functional properties of subunit interactions in human cytidine deaminase. Protein Engi. Dec. 2003;16(12):1055-61. doi: 10.1093/protein/gzg117.

Vincenzeti et al., Possible role of two phenylalanine residues in the active site of human cytidine deaminase. Protein Eng. Nov. 2000;13(11):791-9. doi: 10.1093/protein/13.11.791.

Voigt et al., Rational evolutionary design: the theory of in vitro protein evolution. Adv Protein Chem. 2000;55:79-160.

Voytek et al., Emergence of a fast-reacting ribozyme that is capable of undergoing continuous evolution. Proc Natl Acad Sci U S A. Sep. 25, 2007;104(39):15288-93. Epub Sep. 18, 2007.

Wang et al., Continuous directed evolutions of proteins with improved soluble expression. Nature Chemical Biology. Nat Publishing Group. Aug. 20, 2018; 14(10):972-980.

Wang et al., Evolution of new nonantibody proteins via iterative somatic hypermutation. Proc Natl Acad Sci U S A. Nov. 30, 2004;101(48):16745-9. Epub Nov. 19, 2004.

Wang et al., Programming cells by multiplex genome engineering and accelerated evolution. Nature. Aug. 13, 2009;460(7257):894-8. Epub Jul. 26, 2009.

Wang et al., Syntaxin Requirement for Ca2+-Triggered Exocytosis in Neurons and Endocrine Cells Demonstrated with an Engineered Neurotoxin. Boiochemistry. Apr. 2011;50(14):2711-3.

Webb et al., Production of catalytically inactive BoNT/A1 holoprotein and comparison with BoNT/A1 subunit vaccines against toxin subtypes A1, A2, and A3. Vaccine. 2009;27(33):4490-4497.

Wharton et al., A new-specificity mutant of 434 repressor that defines an amino acid-base pair contact. Nature. Apr. 30-May 6, 1987;326(6116):888-91.

Wharton et al., Changing the binding specificity of a repressor by redesigning an alpha-helix. Nature. Aug. 15-21, 1985;316(6029):601-5.

Williams et al., SNAP23, Syntaxin4, and vesicle-associated membrane protein 7 (VAMP7) mediate trafficking of membrane type 1-matrix metalloproteinase (MT1-MMP) during invadopodium formation and tumor cell invasion. MBoC. Jul. 2014;25:2061-70.

Wright et al., Continuous in vitro evolution of catalytic function. Science. Apr. 25, 1997;276(5312):614-7.

Yamamoto et al., Virological and immunological bases for HIV-1 vaccine design. Uirusu 2007;57(2):133-139. https://doi.org/10.2222/jsv.57.133.

Yanagisawa et al., Crystallographic studies on multiple conformational states of active-site loops in pyrrolysyl-tRNA synthetase. J Mol Biol. May 2, 2008;378(3):634-52. doi: 10.1016/j.jmb.2008.02.045. Epub Feb. 29, 2008.

Yanagisawa et al., Multistep engineering of pyrrolysyl-tRNA synthetase to genetically encode N(epsilon)-(o-azidobenzyloxycarbonyl) lysine for site-specific protein modification. Chem Biol. Nov. 24, 2008;15(11):1187-97. doi: 10.1016/j.chembiol.2008.10.004.

Yeh et al., Retargeted Clostridial neurotoxins as Novel Agents for Treating Chronic Diseases. Biochemistry. Nov. 2011;50:10419-21.

Yi et al., Engineering of TEV protease variants by yeast ER sequestration screening (YESS) of combinatorial libraries. PNAS. Apr. 2013;110(18):7229-34.

Yuan et al., Laboratory-directed protein evolution. Microbiol Mol Biol Rev. Sep. 2005;69(3):373-92.

Zhang et al., Identification and characterization of a novel botulinum neurotoxin. Nat Commun. Aug. 3, 2017;8:14130. doi: 10.1038/ncomms14130.

Zhou et al., Optimization of the Tet-On system for regulated gene expression through viral evolution. Gene Ther. Oct. 2006;13(19):1382-90. Epub May 25, 2006.

Ziemann et al., Gene name errors are widespread in the scientific literature. Genome Biol. Aug. 23, 2016;17(1):177. doi: 10.1186/s13059-016-1044-7.

International Preliminary Report on Patentability for Application No. PCT/US2022/074208, mailed Feb. 8, 2024.

International Preliminary Report on Patentability for Application No. PCT/US2022/079281, mailed May 16, 2024 (B1195.70143WO00).

International Preliminary Report on Patentability for Application No. PCT/US2023/031703, mailed Mar. 13, 2025.

Invitation to Pay Additional Fees for Application No. PCT/US2025/028625, mailed Sep. 24, 2025.

[No Author Listed] Genbank Submission. NCBI; Accession No. AEA29692, version AEA29692.1. cadherin [Trichoplusia ni]. Oct. 18, 2011.

[No Author Listed] Genbank Submission. NCBI; Accession No. AY730621, version AY730621.1. Bacillus thuringiensis plasmid Cry1Ac (cry1Ac) gene, complete cds. Jul. 26, 2016.

[No Author Listed] Genbank Submission. NCBI; Accession No. X18714, version X18714.1. C.botulinum bont/f gene. Apr. 18, 2005. 3 pages. Accessed at: https://www.ncbi.nlm.nih.gov/nuccore/x81714 [last accesed: Jan. 23, 2025].

Adang et al., Characterized full-length and truncated plasmid clones of the crystal protein of *Bacillus thuringiensis* subsp. *kurstaki* HD-73 and their toxicity to Manduca sexta. Gene. 1985;36(3):289-300. doi: 10.1016/0378-1119(85)90184-2.

Agarwal et al., Structural analysis of botulinum neurotoxin serotype F light chain: implications on substrate binding and inhibitor design. Biochemistry. Sep. 6, 2005;44(35):11758-65. doi: 10.1021/bi0510072.

Chappell et al., Generation and characterization of proteolytically active and highly stable truncated and full-length recombinant West Nile virus NS3. Protein Expr Purif. May 2007;53(1):87-96. doi: 10.1016/j.pep.2006.10.022. Epub Nov. 7, 2006.

Chibani-Chennoufi et al., Phage-host interaction: an ecological perspective. J Bacterial. Jun. 2004;186(12):3677-86. doi: 10.1128/JB.186.12.3677-3686.2004.

Hendel et al., Directed evolution in mammalian cells. Nat Methods. Apr. 2021;18(4):346-357. doi: 10.1038/s41592-021-01090-x. Epub Apr. 7, 2021.

Jeruzalmi et al., Structure of T7 RNA polymerase complexed to the transcriptional inhibitor T7 lysozyme. EMBO J. Jul. 15, 1998;17(14):4101-13. doi: 10.1093/emboj/17.14.4101.

Jurat-Fuentesa et al., Specificity determinants for Cry insecticidal proteins: Insights from their mode of action. J Invertebr Pathol. Jan. 2017:142:5-10. doi: 10.1016/j.jip.2016.07.018. Epub Jul. 29, 2016.

Lucena et al., Molecular approaches to improve the insecticidal activity of Bacillus thuringiensis Cry toxins. Toxins (Basel). Aug. 13, 2014;6(8):2393-423. doi: 10.3390/toxins6082393.

(56) References Cited

OTHER PUBLICATIONS

Mayrhofer et al., Mutation-oriented profiling of autoinhibitory kinase conformations predicts RAF inhibitor efficacies. Proc Natl Acad Sci USA. Dec. 8, 2020;117(49):31105-31113. doi: 10.1073/pnas.2012150117. Epub Nov. 23, 2020.
McCreary et al., Reprogramming protease specificity using phage-assisted evolution. Poster. Harvard University. CCB Department G1 Poster Session. Presented Aug. 25, 2022.
McCreary, Evolution of a procaspase-1 cleaving protease. Presentation. 2021. 10 pages.
Meyer et al., Molecular evolution picks up the PACE. Nat Biotechnol. Jun. 7, 2011;29(6):502-3. doi: 10.1038/nbt.1884.
Morrison et al., Chapter 4: Future directions and potential applications of this work. Thesis for Harvard University. 2021. 29 pages.
Morrison et al., Disulfide-compatible phage-assisted continuous evolution in the periplasmic space. Author Manuscript with Supplementary information. Broad Institute of Harvard and MIT and Harvard University. 2022. 75 pages.
Nakahira et al., Theophylline-dependent riboswitch as a novel genetic tool for strict regulation of protein expression in Cyanobacterium Synechococcus elongatus PCC 7942. Plant Cell Physiol. Oct. 2013;54(10):1724-35. doi: 10.1093/pcp/pct115. Epub Aug. 21, 2013.
Packer et al., Phage-assisted continuous evolution of proteases with altered substrate specificity. Nat Commun. Oct. 16, 2017;8(1):956. doi: 10.1038/s41467-017-01055-9.
Pardo-Lopez et al., Strategies to improve the insecticidal activity of Cry toxins from Bacillus thuringiensis. Peptides. Author manuscript; available in PMC: Mar. 1, 2010. Published in final edited form as: Peptides. Aug. 19, 2008;30(3):589-595. doi: 10.1016/j.peptides.2008.07.027.
Pigott et al., Role of receptors in Bacillus thuringiensis crystal toxin activity. Microbial Mol Biol Rev. Jun. 2007;71(2):255-81. doi: 10.1128/MMBR.00034-06.
Polyak et al., Overview: Gene Structure. Holland-Frei Cancer Medicine. 6th edition. 2003. Accessed at: www.ncbi.nlm.nih.gov/books/NBK12983.
Romanini et al., A Heritable Recombination system for synthetic Darwinian evolution in yeast. ACS Synth Biol. Dec. 21, 2012;1(12):602-9. doi: 10.1021/sb3000904.
Vande Walle et al., Snapshot of a Deadly Embrace: The Caspase-1-GSDMD Interface. Immunity. Jul. 14, 2020;53(1):6-8. doi: 10.1016/j.immuni.2020.06.019.
PCT/US2023/031703, Nov. 24, 2023, International Search Report and Written Opinion.
International Search Report and Written Opinion for Application No. PCT/US2023/031703, mailed Nov. 24, 2023.
Latremoliere et al., Reduction of Neuropathic and Inflammatory Pain through Inhibition of the Tetrahydrobiopterin Pathway. Neuron. Jun. 17, 2015;86(6):1393-406. doi: 10.1016/j.neuron.2015.05.033.
International Search Report and Written Opinion for Application No. PCT/US2025/028625, mailed Nov. 14, 2025.
Vande Walle et al., Drugging the NLRP3 inflammasome: from signalling mechanisms to therapeutic targets. Nat Rev Drug Discov. Jan. 2024;23(1):43-66. doi: 10.1038/s41573-023-00822-2. Epub Nov. 29, 2023.

* cited by examiner

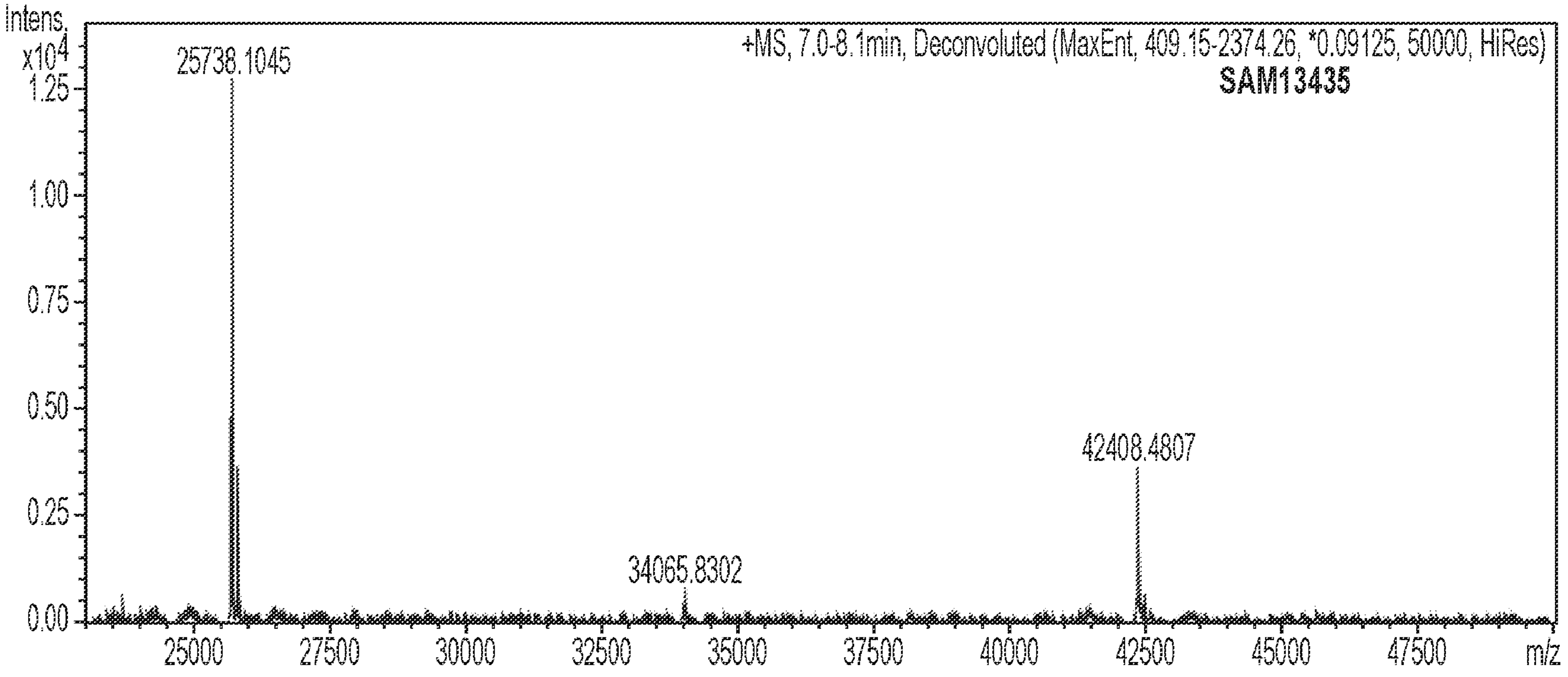

MKIEEGKLVIWINGDKGYNGLAEVGKKFEKDTGIKVTVEHPDKLEEKFPQVAATGDGPDIIFWAHDRFGGY
AQSGLLAEITPDKAFQDKLYPFTWDAVRYNGKLIAYPIAVEALSLIYNKDLLPNPPKTWEEIPALDKELKAKG
KSALMFNLQEPYFTWPLIAADGGYAFKYENGKYDIKDVGVDNAGAKAGLTFLVDLIKNKHMNADTDYSIAE
AAFNKGETAMTINGPWAWSNIDTSKVNYGVTVLPTFKGQPSKPFVGVLSAGINAASPNKELAKEFLENYL
LTDEGLEAVNKDKPLGAVALKSYEEELAKDPRIAATMENAQKGEIMPNIPQMSAFWYAVRTAVINAASGRQ
TVDEALKDAQTNSSSGGSGGSENGSLCDQEIDS SEQ ID NO: 27

Expected (m/z): 42408.90
Found (m/z): 42408.48

ICSIERADNGGSGGSPPYTITYFPVRGRCEAMRMLLADQDQSWKEEVVTMETWPPLKPSCLFRQLPKFQ
DGDLTLYQSNAILRHLGRSFGLYGKDQKEAALVDMVNDGVEDLRCKYATLIYTNYEAGKEKYVKELPEHL
KPFETLLSQNQGGQAFVVGSQISFADYNLLDLLRIHQVLNPSCLDAFPLLSAYVARLSARPKIKAFLASPEH
VNRPINGNGKQHHHHHH SEQ ID NO: 28

Expected (m/z): 25738.34
Found (m/z): 25738.10

FIG. 3

EVOLUTION OF BOTULINUM NEUROTOXIN PROTEASES

CROSS REFERENCE TO-RELATED APPLICATIONS

This application is a national stage filing under 35 U.S.C. § 371 of International PCT Application PCT/US2021/064125, filed Dec. 17, 2021, which claims priority under 35 U.S.C. § 119(e) to U.S. Provisional Application, U.S. Ser. No. 63/127,340, filed on Dec. 18, 2020, each of which is incorporated herein by reference.

FEDERALLY SPONSORED RESEARCH

This invention was made with government support under EB027793, EB022376, GM118062, GM122261, NS080833, and NS106159 awarded by the National Institutes of Health. The government has certain rights in the invention.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Jun. 14, 2023, is named B119570116US01-SEQ-CBD and is 106,537 bytes in size.

BACKGROUND

Over the last few decades, the medical community has witnessed a remarkable shift in the composition of pharmaceutical therapies from traditional small molecules to biomacromolecules (e.g., enzymes, compositions of multiple proteins, peptides, amino acids, polymers, nucleic acids). The growing number of macromolecular therapeutics is a result of their potential for highly specific interactions in biological systems and has been facilitated by improvements in molecular biology and biomolecule engineering. Despite their tremendous success, macromolecular therapies have been limited almost exclusively to extracellular targets due to the significant challenge of their controllable delivery into the cytoplasm. While a number of notable advances have been made in the area of macromolecular delivery, this important problem remains a major barrier to the development and use of macromolecular therapeutics that address intracellular targets. As an alternative, several natural protein systems are capable of cytoplasmic self-delivery. However, the ability to reengineer these systems to imbue them with the necessary binding or catalytic activities and specificities for therapeutic effect is largely underexplored and underdeveloped.

SUMMARY

The disclosure relates to fusion proteins comprising certain subcellular localization peptides (e.g., pleckstrin homology (PH) domains, etc.) connected to novel Botulinum neurotoxin (BoNT) protease variants. In some embodiments, the BoNT protease variants have been evolved using Phage-Assisted Continuous Evolution (PACE), for example, as described in U.S. Pat. No. 9,023,594, issued May 5, 2015; U.S. Pat. No. 9,771,574, issued Sep. 26, 2017; U.S. patent application Ser. No. 15/713,403, filed Sep. 22, 2017 (now abandoned); International PCT Application PCT/US2009/056194, filed Sep. 8, 2009, published as WO 2010/028347 on Mar. 11, 2010; U.S. Provisional Patent Application Ser. No. 61/426,139, filed Dec. 22, 2010; U.S. Pat. No. 9,394,537, issued Jul. 19, 2016; U.S. Pat. No. 10,336,997, issued Jul. 2, 2019; U.S. patent application Ser. No. 16/410,767, filed May 13, 2019; International PCT Application PCT/US2011/066747, filed Dec. 22, 2011, published as WO 2012/088381 on Jun. 28, 2012; U.S. Provisional Patent Application Ser. No. 61/929,378 filed Jan. 20, 2014; U.S. Pat. No. 10,179,911, issued Jan. 15, 2019; U.S. patent application Ser. No. 16/238,386, filed Jan. 2, 2019; International PCT Application PCT/US2015/012022, filed Jan. 20, 2015; U.S. Provisional Patent Application Ser. No. 62/158,982, filed May 8, 2015; U.S. Provisional Patent Application Ser. No. 62/187,669, filed Jul. 1, 2015; U.S. Provisional Patent Application Ser. No. 62/067,194, filed Oct. 22, 2014; U.S. Pat. No. 10,920,208, issued Feb. 16, 2021; International PCT Application PCT/US2018/048134, filed Aug. 27, 2018; U.S. Pat. No. 9,267,127, issued Feb. 23, 2016; International PCT Application PCT Application, PCT/US2015/057012, filed Oct. 22, 2015, published as WO 2016/077052; International PCT Application PCT/US2016/027795, filed Apr. 15, 2016, published as WO 2016/168631; International PCT Application, PCT/US2009/056194, filed Sep. 8, 2009, published as WO 2010/028347 on Mar. 11, 2010; International PCT Application, PCT/US2011/066747, filed Dec. 22, 2011, published as WO 2012/088381 on Jun. 28, 2012; U.S. Provisional Patent Application Ser. No. 62/067,194, filed Oct. 22, 2014, U.S. Pat. No. 9,023,594, issued May 5, 2015, and International PCT Application, PCT/US2018/051557, published as WO 2018/056002 on Mar. 21, 2019, the entire contents of each of which are incorporated herein by reference. As described herein, fusion proteins comprising a PH domain and a BoNT protease light chain variant are attractive candidates for cytosolic delivery of the BoNT protease variant because it has been surprisingly discovered that addition of a PH domain allows the BoNTs to efficiently cleave intracellular targets (e.g., intracellular targets of cells having an intact cell membrane). In some embodiments, the PH domain of the fusion protein directs the BoNT protease to a particular subcellular location (e.g., the plasma membrane) of a cell in order to increase contact of the protease with its target substrate (e.g., a Phosphatase and tensin homolog (PTEN) protein). In some embodiments, the disclosure relates to fusion proteins comprising a PH domain and an evolved BoNT/E protease variant that cleaves a desired substrate (e.g., a disease-associated intracellular protein, such as PTEN protein) are described herein.

Accordingly, in some aspects, the disclosure provides a fusion protein comprising a pleckstrin homology (PH) domain (e.g., SEQ ID NO.: 2, 18, 19, 20, or 21); and a BoNT/E protease light chain having at least 80% (e.g., at least 80%, 85%, 90%, 95%, 99%, etc.) sequence identity to SEQ ID NO.: 1.

In some embodiments, the PH domain is a human PH domain. In some embodiments, a PH domain comprises a human phospholipase C delta 1 (PLCδ1) PH domain. In some embodiments, a PH domain has an amino acid sequence that is at least 80% (e.g., at least 80%, 85%, 90%, 95%, 99%, etc.) identical to the sequence set forth in SEQ ID NO.: 2.

In some embodiments, a BoNT/E protease light chain comprises an amino acid substitution in at least one of the following positions relative to SEQ ID NO. 1: C26, Q27, E28, I35, G49, H56, H56, S99, G101, N118, D156, E159, N161, S162, S163, S166, L167, M172, I203, I232, T242, R244, N248, I262, I263, A313, I316, G353, Q354, Y355, Y357, K359, N365, S367, N390, G403, or L404.

In some embodiments, a BoNT/E protease light chain comprises at least one of the following amino acid substitutions relative to SEQ ID NO.: 1: C26Y, Q27H, E28K, I35V, G49S, H56L, H56Y, S99A, S99T, G101S, N118D, D156N, E159L, N161Y, S162Q, S163R, S166R, M172K, I203V, I232T, T242A, R244V, N248K, I262T, I263V, A313V, I316T, G353E, Q354R, Q354W, Y355P, Y355H, Y357F, K359R, N365S, S367F, N390D, G403E, or L404* (e.g., "L404Stop").

In some embodiments, a BoNT/E protease comprises the following amino acid substitutions relative to SEQ ID NO.: 1: C26Y, Q27H, S99A, G101S, N118D, D156N, E159L, N161Y, S162Q, S163R, L167A, M172K, I232T, N248K, Q354R, Y355P, and Y357F.

In some embodiments, a fusion protein has at least 80% sequence identity (e.g., at least 80%, at least 85%, at least 90%, at least 95%, at least 96%, at least 97%, at least 98%, at least 99%, at least 99.5%, at least 99.9%, or more) to SEQ ID NO.: 5 or 6.

In some embodiments, a fusion protein comprises or consists of the amino acid sequence set forth in SEQ ID NO.: 5 or 6.

In some embodiments, a PH domain is positioned N-terminal relative to the BoNT/E protease light chain. In some embodiments, a PH domain and a BoNT/E protease light chain are directly connected.

In some embodiments, the fusion protein further comprises a linker, for example, a linker connecting the PH domain to the BoNT/E protease light chain. In some embodiments, the linker comprises a peptide linker. In some embodiments, the peptide linker comprises a glycine-rich linker, a proline-rich linker, glycine/serine-rich linker, or alanine/glutamic acid-rich linker.

In some embodiments, a BoNT/E protease light chain is catalytically active. In some embodiments, a BoNT/E protease light chain is capable of cleaving a non-canonical BoNT/E substrate. In some embodiments, a non-canonical BoNT/E substrate is a Phosphatase and tensin homolog (PTEN) protein (e.g., a protein having an amino acid sequence that is at least 70% identical to the amino acid sequence set forth in SEQ ID NO.: 12 or 13).

In some embodiments, a BoNT/E protease light chain does not cleave a SNAP protein. In some embodiments, a BoNT/E protease light chain does not cleave SNAP25 (e.g., a protein having an amino acid sequence that is at least 70%, 80%, 85%, 90%, 95%, or 99% identical to the amino acid sequence set forth in SEQ ID NO.: 16 or 17).

In some aspects, the disclosure provides an isolated nucleic acid encoding a fusion protein as described herein. In some embodiments, the isolated nucleic acid has at least 60%, 70%, 80%, 90%, 95%, or 99% or more identity to the nucleic acid sequence set forth in SEQ ID NO.: 10 or 11. In some embodiments, an isolated nucleic acid comprises or consists of the nucleic acid sequence set forth in SEQ ID NO.: 10 or 11, which are encoded by SEQ ID NO.: 5 and 6, respectively. In some embodiments, the nucleic acid sequence encoding a fusion protein is codon-optimized. In some embodiments, the nucleic acid sequence is codon-optimized for expression in mammalian (e.g., human) cells.

In some aspects, the disclosure provides a vector comprising an isolated nucleic acid as described herein, for example, an isolated nucleic acid encoding a fusion protein comprising a PH domain and a BoNT/E protease light chain. In some embodiments, a vector is a plasmid or a viral vector. In some embodiments, a viral vector is a lentiviral vector.

In some aspects, the disclosure provides a host cell comprising a fusion protein, isolated nucleic, or vector as described herein. In some embodiments, the cell is a mammalian cell. In some embodiments, the mammalian cell is a human cell. In some embodiments, the cell is in a subject.

In some aspects, the disclosure provides a method of cleaving an intracellular protein, the method comprising delivering to a cell a fusion protein, isolated nucleic acid, or vector as described herein, whereby the fusion protein contacts and cleaves the intracellular protein in the cell. In some embodiments, the intracellular protein is a PTEN protein. In some embodiments, the cell is a mammalian cell. In some embodiments, the cell comprises an intact cell membrane (e.g., the cell has not been permeabilized, the cell is alive, etc.). In some embodiments, the intracellular protein is cleaved in a plasma membrane of a cell.

In some aspects, the disclosure provides a use of a fusion protein, isolated nucleic acid, or vector as described herein in reducing PTEN activity or the amount of functional PTEN in a cell or subject. In some embodiments, the cell is a mammalian cell. In some embodiments, the mammalian cell is a human cell. In some embodiments, the cell is intact. In some embodiments, the cell is in a subject. In some embodiments, the subject is a human. In some embodiments, the cell or subject is characterized as having PTEN activity or expression that is higher than a normal healthy cell or subject

BRIEF DESCRIPTION OF DRAWINGS

FIG. 1A shows evaluation of PTEN cleavage by evolved HA-tagged E(4130)A2 protease after transient co-transfection of plasmids encoding protease and FLAG-tagged PTEN. PH-E(4130)A2 contains an N-terminal pleckstrin homology domain fused to E(4130)A2. The Western blot was visualized using anti-FLAG primary antibodies. Numbers indicate the ratio of BoNT/LC plasmid:PTEN substrate plasmid. FIG. 1B shows a schematic indicating E(4130)A2 amino acid mutations relative to wild-type BoNT/E light chain protease.

FIG. 3 shows identification of the cleavage site of PTEN by E(4130)A2. Assay was performed using 2 μM MBP-PTEN(N292-N311)-GST substrate, with 100 nM protease, then analyzed by LCMS for average intact mass. PTEN (N292-N311) is indicated in red.

DEFINITIONS

Figure 1A:
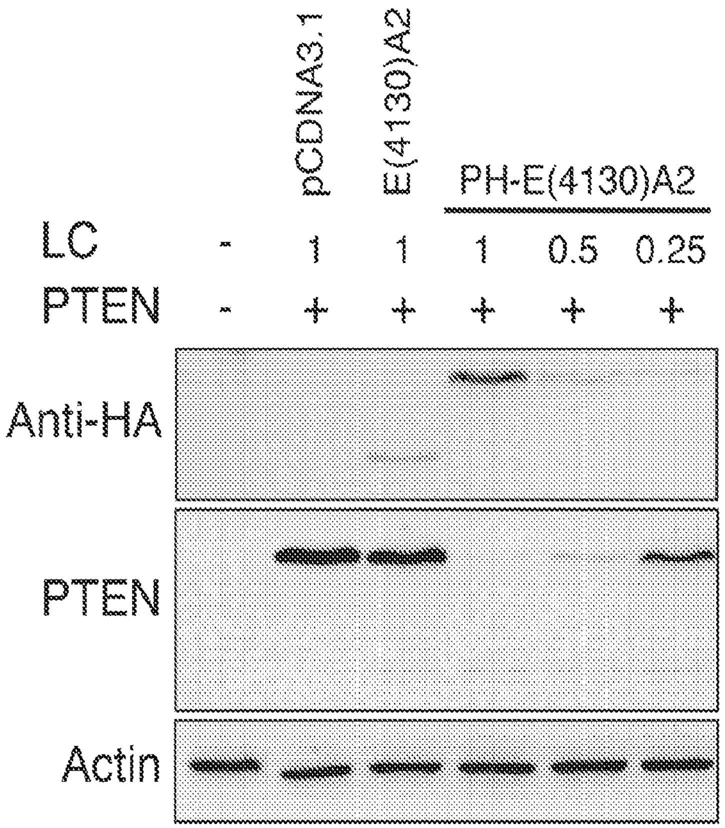
FIGS. 1A-1B show representative data for evaluation of evolved BoNT protease fusion proteins in mammalian cells.

The term "protein," as used herein, refers to a polymer of amino acid residues linked together by peptide bonds. The term, as used herein, refers to proteins, polypeptides, and peptides of any size, structure, or function. Typically, a protein will be at least three amino acids long but is generally longer than 50 amino acids in length. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in an inventive protein may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein may also be a single molecule or may be a multi-molecular complex. A protein may be just a fragment of a naturally occurring protein or peptide. A protein may be naturally occurring, recombinant, or synthetic, or any combination of these.

The term "peptide", as used herein, refers to a short, contiguous chain of amino acids linked to one another by peptide bonds. Generally, a peptide ranges from about 2 amino acids to about 50 amino acids in length (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids in length) but may be longer in the case of a polypeptide. In some embodiments, a peptide is a fragment or portion of a larger protein, for example comprising one or more domains of a larger protein. Peptides may be linear (e.g., branched, unbranched, etc.) or cyclic (e.g., form one or more closed rings). A "polypeptide", as used herein, refers to a longer (e.g., between about 50 and about 100), continuous, unbranched peptide chain.

The term "pleckstrin homology domain" or "PH domain," as used herein, refers to a polypeptide of roughly 100-120 amino acids in length that binds phosphatidylinositol lipids within biological membranes (e.g., phosphatidylinositol (3,4,5)-trisphosphate and phosphatidylinositol (4,5)-bisphosphate) and proteins, such as the βγ-subunits of heterotrimeric G proteins, and protein kinase C. Generally, PH domains function in recruiting and trafficking proteins to different cellular and intracellular membranes. PH domains are found in proteins across several organisms, for example, humans, yeast (e.g., *S. cerevisiae*) and nematodes (e.g., *C. elegans*). There are hundreds of proteins that contain PH domains in humans alone. Sequences of PH domains are known in the art, for example as described by European Molecular Biology Lab Protein Family (Pfam) database entry "PF00169" and InterPro database entry IPR001849.

The term "protease," as used herein, refers to an enzyme that catalyzes the hydrolysis of a peptide (amide) bond linking amino acid residues together within a protein. The term embraces both naturally occurring and engineered proteases. Many proteases are known in the art. Proteases can be classified by their catalytic residue, and protease classes include, without limitation, serine proteases (serine alcohol), threonine proteases (threonine secondary alcohol), cysteine proteases (cysteine thiol), aspartate proteases (aspartate carboxylic acid), glutamic acid proteases (glutamate carboxylic acid), and metalloproteases (metal ion, e.g., zinc). The structures in parentheses correlate to the respective catalytic moiety of the proteases of each class. Some proteases are highly promiscuous and cleave a wide range of protein substrates, e.g., trypsin or pepsin. Other proteases are highly specific and only cleave substrates with a specific sequence. In another example, Botulinum toxin proteases (BoNTs) generally cleave specific SNARE proteins. Proteases that cleave in a very specific manner typically bind to multiple amino acid residues of their substrate. Suitable proteases and protease cleavage sites, also sometimes referred to as "protease substrates," will be apparent to those of skill in the art and include, without limitation, proteases listed in the MEROPS database, accessible at merops.sanger.ac.uk and described in Rawlings et al., (2014) MEROPS: the database of proteolytic enzymes, their substrates and inhibitors. *Nucleic Acids Res* 42, D503-D509, the entire contents of each of which are incorporated herein by reference. The disclosure is not limited in this respect.

The term "Botulinum neurotoxin (BoNT) protease," as used herein, refers to a protease derived from, or having at least 70% sequence homology to (or at least 70% identity to) a Botulinum neurotoxin (BoNT), for example, a BoNT derived from a bacterium of the genus *Clostridium* (e.g., *C. botulinum*). Structurally, BoNT proteins comprise two conserved domains, a "heavy chain" (HC) and a "light chain" (LC). The LC comprises a zinc metalloprotease domain responsible for the catalytic activity of the protein. The HC typically comprises an HCC domain, which is responsible for binding to neuronal cells, and an HCN domain, which mediates translocation of the protein into a cell. Examples of BoNT HC domains are represented by the amino acid sequences set forth in SEQ ID NOs.: 14 and 15 below.

```
BoNT E HCC Domain
SSVLNMRYKNDKYVDTSGYDSNININGDVYKYPTNKNQFEIYNDKLSEV

NISQNDYIIYDNKYKNFSISFWVRIPNYDNKIVNVNNEYTIINCMRDNN

SGWKVSLNHNEIIWTLQDNAGINQKLAFNYGNANGISDYINKWIFVTIT

NDRLGDSKLYINGNLIDQKSILNLGNIHVSDNILFKIVNCSYTRYIGIR

YFNIFDKELDETEIQTLYSNEPNTNILKDFWGNYLLYDKEYYLLNVLKP

NNFIDRRKDSTLSINNIRSTILLANRLYSGIKVKIQRVNNSSTNDNLVR

KNDQVYINFVASKTHLFPLYADTATTNKEKTIKISSSGNRFNQVVVMNS

VGNNCTMNFKNNNGNNIGLLGFKADTVVASTWYYTHMRDHTNSNGCFWN

FISEEHGWQEK (BpNT E HC_C, Binding domain; SEQ ID

NO.: 15)

BoNT E HCN Domain
CKNIVSVKGIRKSICIEINNGELFFVASENSYNDDNINTPKEIDDTVTS

NNNYENDLDQVILNFNSESAPGLSDEKLNLTIQNDAYIPKYDSNGTSDI

EQHDVNELNVFFYLDAQKVPEGENNVNLTSSIDTALLEQPKIYTFFSSE

FINNVNKPVQAALFVSWIQQVLVDFTTEANQKSTVDKIADISIVVPYIG

LALNIGNEAQKGNFKDALELLGAGILLEFEPELLIPTILVFTIKSFLGS

SDNKNKVIKAINNALKERDEKWKEVYSFIVSNWMTKINTQFNKRKEQMY

QALQNQVNAIKTIIESKYNSYTLEEKNELTNKYDIKQIENELNQKVSIA

MNNIDRFLTESSISYLMKLINEVKINKLREYDENVKTYLLNYIIQHGSI

LGESQQELNSMVTDTLNNSIPFKLSSYTDDKILISYFNKFFKRIKS

(BoNT E HC_N, translocation domain; SEQ ID NO.: 14)
```

There are seven serotypes of BoNTs, denoted BoNT A-G. BoNT serotypes A, C, and E cleave synaptosome-associated protein (SNAP25). BoNT serotype C has also been observed to cleave syntaxin. BoNT serotypes B, D, F, and G cleave vesicle-associated membrane proteins (VAMPs). An example of a SNAP25 protein that is cleaved by wild-type BoNT proteases (e.g., BoNT E) is represented by the amino acid sequence set forth in SEQ ID NO.: 16 below. In some embodiments, a SNAP25 substrate that is cleaved by wild-type BoNT proteases comprises the following amino acid sequence RQIDRIMEKA (SEQ ID NO: 17).

SNAP25 Protein Sequence

```
                                           (SEQ ID NO.: 16)
MAEDADMRNELEEMQRRADQLADESLESTRRMLQLVEESKDAGIRTLVM

LDEQGEQLERIEEGMDQINKDMKEAEKNLTDLGKFCGLCVCPCNKLKSS

DAYKKAWGNNQDGVVASQPARVVDEREQMAISGGFIRRVTNDARENEMD

ENLEQVSGIIGNLRHMALDMGNEIDTQNRQIDRIMEKADSNKTRIDEAN

QRATKMLGSG
```

A wild-type BoNT protease refers to the amino acid sequence of a BoNT protease as it naturally occurs in a *Clostridium botulinum* genome. A non-limiting example of a wild-type BoNT/E protease light chain sequence is represented by the amino acid sequence set forth in SEQ ID NO.: 1.

The term "BoNT protease variant," as used herein, refers to a protein (e.g., a BoNT protease) having one or more amino acid variations introduced into the amino acid sequence, e.g., as a result of application of the PACE method or by genetic engineering (e.g., recombinant gene expression, gene synthesis, etc.), as compared to the amino acid sequence of a naturally-occurring or wild-type BoNT protein (e.g., SEQ ID NO.: 1). Amino acid sequence variations may include one or more mutated residues within the amino acid sequence of the protease, e.g., as a result of a change in the nucleotide sequence encoding the protease that results in a change in the codon at any particular position in the coding sequence, the deletion of one or more amino acids (e.g., a truncated protein), the insertion of one or more amino acids, or any combination of the foregoing. In certain embodiments, a BoNT protease variant cleaves a different target peptide (e.g., has broadened or different substrate specificity) relative to a wild-type BoNT protease. For example, in some embodiments, a BoNT/E protease variant cleaves a PTEN protein or peptide.

The term "continuous evolution," as used herein, refers to an evolution procedure, in which a population of nucleic acids is subjected to multiple rounds of (a) replication, (b) mutation (or modification of the primary sequence of nucleotides of the nucleic acids in the population), and (c) selection to produce a desired evolved product, for example, a novel nucleic acid encoding a novel protein with a desired activity, wherein the multiple rounds of replication, mutation, and selection can be performed without investigator interaction, and wherein the processes (a)-(c) can be carried out simultaneously. Typically, the evolution procedure is carried out in vitro, for example, using cells in culture as host cells. In general, a continuous evolution process provided herein relies on a system in which a gene of interest is provided in a nucleic acid vector that undergoes a life-cycle including replication in a host cell and transfer to another host cell, wherein a critical component of the life-cycle is deactivated and reactivation of the component is dependent upon a desired variation in an amino acid sequence of a protein encoded by the gene of interest, for example, a gene encoding s BoNT/E protease light chain.

The term "phage-assisted continuous evolution (PACE)," as used herein, refers to continuous evolution that employs phage as viral vectors. PACE methods are known in the art and are described, for example, in International PCT Application, PCT/US2009/056194, filed Sep. 8, 2009, published as WO 2010/028347 on Mar. 11, 2010; International PCT Application, PCT/US2011/066747, filed Dec. 22, 2011, published as WO 2012/088381 on Jun. 28, 2012; and U.S. Application, U.S. Ser. No. 13/922,812, filed Jun. 20, 2013, each of which is incorporated herein by reference.

The term "nucleic acid," as used herein, refers to a polymer of nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolo-pyrimidine, 3-methyl adenosine, 5-methylcytidine, C5-bromouridine, C5-fluorouridine, C5-iodouridine, C5-propynyl-uridine, C5-propynyl-cytidine, C5-methylcytidine, 7-deazaadenosine, 7-deazaguanosine, 8-oxoadenosine, 8-oxoguanosine, 0(6)-methylguanine, 4-acetylcytidine, 5-(carboxyhydroxymethyl)uridine, dihydrouridine, methylpseudouridine, 1-methyl adenosine, 1-methyl guanosine, N6-methyl adenosine, and 2-thiocytidine), chemically modified bases, biologically modified bases (e.g., methylated bases), intercalated bases, modified sugars (e.g., 2'-fluororibose, ribose, 2'-deoxyribose, 2'-O-methylcytidine, arabinose, and hexose), or modified phosphate groups (e.g., phosphorothioates and 5'-N-phosphoramidite linkages).

An "isolated nucleic acid" generally refers to refers to a nucleic acid that is: (i) amplified in vitro by, for example, polymerase chain reaction (PCR); (ii) recombinantly produced by molecular cloning; (iii) purified, as by restriction endonuclease cleavage and gel electrophoretic fractionation, or column chromatography; or (iv) synthesized by, for example, chemical synthesis. An isolated nucleic acid is one which is readily manipulatable by recombinant DNA techniques known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulatable by standard techniques known to those of ordinary skill in the art. As used herein with respect to proteins or peptides, the term "isolated" refers to a protein or peptide that has been isolated from its natural environment or artificially produced (e.g., by chemical synthesis, by recombinant DNA technology, etc.).

The term "vector," as used herein, refers to any genetic element, such as a plasmid, phage, transposon, cosmid, chromosome, artificial chromosome, virus, virion, etc., which is capable of replication when associated with the proper control elements, and which can transfer gene sequences between cells.

The term "viral vector," as used herein, refers to a nucleic acid (or isolated nucleic acid) comprising a viral genome that, when introduced into a suitable host cell, can be replicated and packaged into viral particles able to transfer the viral genome into another host cell. The term viral vector extends to vectors comprising truncated or partial viral genomes. For example, in some embodiments, a viral vector is provided that lacks a gene encoding a protein essential for the generation of infectious viral particles or for viral replication. In some embodiments, a viral vector is a lentiviral vector, adenoviral vector, or an adeno-associated virus vector.

The term "host cell," as used herein, refers to a cell that can host a viral vector useful for a continuous evolution process as provided herein. A cell can host a viral vector if it supports expression of genes of viral vector, replication of the viral genome, and/or the generation of viral particles. One criterion to determine whether a cell is a suitable host cell for a given viral vector is to determine whether the cell can support the viral life cycle of a wild-type viral genome that the viral vector is derived from. For example, if the viral vector is a modified M13 phage genome, as provided in some embodiments described herein, then a suitable host cell would be any cell that can support the wild-type M13 phage life cycle. Suitable host cells for viral vectors useful in continuous evolution processes are well known to those of skill in the art, and the invention is not limited in this respect.

In some embodiments, modified viral vectors are used in continuous evolution processes as provided herein. In some embodiments, such modified viral vectors lack a gene required for the generation of infectious viral particles. In some such embodiments, a suitable host cell is a cell comprising the gene required for the generation of infectious viral particles, for example, under the control of a constitutive or a conditional promoter (e.g., in the form of an accessory plasmid, as described herein). In some embodiments, the viral vector used lacks a plurality of viral genes. In some such embodiments, a suitable host cell is a cell that comprises a helper construct providing the viral genes required for the generation of viral particles. A cell is not required to actually support the life cycle of a viral vector used in the methods provided herein. For example, a cell comprising a gene required for the generation of infectious viral particles under the control of a conditional promoter may not support the life cycle of a viral vector that does not comprise a gene of interest able to activate the promoter, but it is still a suitable host cell for such a viral vector. In some embodiments, the viral vector is a phage, and the host cell is a bacterial cell. In some embodiments, the host cell is an *E. coli* cell. Suitable *E. coli* host strains will be apparent to those of skill in the art, and include, but are not limited to, New England Biolabs (NEB) Turbo, Top10F', DH12S, ER2738, ER2267, XL1-Blue MRF', and DH10B. In some embodiments, the strain of *E. coli* used is known as S1030 (available from Addgene). In some embodiments, the strain of *E. coli* use to express proteins is BL21(DE3). These strain names are art recognized, and the genotype of these strains has been well characterized. It should be understood that the above strains are exemplary only, and that the invention is not limited in this respect.

The term "promoter" refers to a nucleic acid molecule with a sequence recognized by the cellular transcription machinery and able to initiate transcription of a downstream gene. A promoter can be constitutively active, meaning that the promoter is always active in a given cellular context, or conditionally active, meaning that the promoter is only active under specific conditions. For example, a conditional promoter may only be active in the presence of a specific protein that connects a protein associated with a regulatory element in the promoter to the basic transcriptional machinery, or only in the absence of an inhibitory molecule. A subclass of conditionally active promoters are inducible promoters that require the presence of a small molecule "inducer" for activity. Examples of inducible promoters include, but are not limited to, arabinose-inducible promoters, Tet-on promoters, and tamoxifen-inducible promoters. A variety of constitutive, conditional, and inducible promoters are well known to the skilled artisan, and the skilled artisan will be able to ascertain a variety of such promoters useful in carrying out the instant invention, which is not limited in this respect.

The term "cell," as used herein, refers to a cell derived from an individual organism, for example, from a mammal. A cell may be a prokaryotic cell or a eukaryotic cell. In some embodiments, the cell is a eukaryotic cell, for example, a human cell, a mouse cell, a pig cell, a hamster cell, a monkey cell, etc. In some embodiments, the cell is obtained from a subject having or suspected of having a disease characterized by increased PTEN levels/activity, for example, ischemic neuronal injury (stroke). In some embodiments, the cell is in a subject (e.g., the cell is in vivo). In some embodiments, the cell is intact (e.g., the outer membrane of the cell, such as the plasma membrane, is intact or not permeabilized).

The term "intracellular environment," as used herein, refers to the aqueous biological fluid (e.g., cytosol) forming the microenvironment contained by the outer membrane of a cell. For example, in a subject, an intracellular environment may include the cytoplasm of a cell or cells of a target organ or tissue (e.g., the cytosol of neuronal cells in CNS tissue). In another example, a cellular environment is the cytoplasm of a cell or cells surrounded by cell culture growth media housed in an in vitro culture vessel, such as a cell culture plate or flask.

The term "subject," as used herein, refers to an individual organism, for example, a mammal. In some embodiments, the subject is a human. In some embodiments, the subject is a non-human mammal. In some embodiments, the subject is a non-human primate. In some embodiments, the subject is a rodent. In some embodiments, the subject is a sheep, a goat, a cow, a cat, or a dog. In some embodiments, the subject is a vertebrate, an amphibian, a reptile, a fish, an insect, a fly, or a nematode. In some embodiments, the subject is a research animal. In some embodiments, the subject is genetically engineered, e.g., a genetically engineered non-human subject. The subject may be of either sex and at any stage of development. In some embodiments, the subject has a disease characterized by increased activity of an intracellular protein (e.g., a SNARE protein, PTEN, etc.).

The "percent identity" of two amino acid sequences may be determined using algorithms or computer programs, for example, the algorithm of Karlin and Altschul, *Proc. Natl. Acad. Sci. USA* 87:2264-68, 1990, modified as in Karlin and Altschul, *Proc. Natl. Acad. Sci. USA* 90:5873-77, 1993. Such an algorithm is incorporated into various computer programs, for example NBLAST and XBLAST programs (version 2.0) of Altschul et al. *J. Mol. Biol.* 215:403-10, 1990. BLAST protein searches can be performed with the XBLAST program, score=50, word length=3 to obtain amino acid sequences homologous to the protein molecules of interest. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used. BLAST nucleotide searches can be performed with the NBLAST nucleotide program parameters set, e.g., for score=100, wordlength=12 to obtain nucleotide sequences homologous to a nucleic acid molecule described herein. BLAST protein searches can be performed with the XBLAST program parameters set, e.g., to score 50, wordlength=3 to obtain amino acid sequences homologous to a protein molecule described herein. To obtain gapped alignments for comparison purposes, Gapped BLAST can be utilized as described in Altschul, S F et al., (1997) *Nuc. Acids Res.* 25: 3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the world-wide web, ncbi.nlm.nih.gov). Another specific, non-limiting example of a mathematical algorithm utilized for the comparison of sequences is the algorithm of Myers and Miller, 1988, *CABIOS* 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

DETAILED DESCRIPTION

Aspects of the disclosure relate to compositions and methods for cleaving intracellular protein targets. The disclosure is based, in part, on the surprising discovery that appending a pleckstrin homology (PH) domain to a BoNT/E protease light chain variant results in a fusion protein that 1) localizes the protease variant to the correct subcellular location, and 2) cleaves the protein target of the variant at that subcellular location. In some embodiments, the BoNT/E protease light chain variant has been evolved (e.g., using PACE) to cleave a non-canonical BoNT/E substrate, for example, a PTEN protein. In some embodiments, the evolved BoNT/E protease light chain variant has activity toward a non-canonical substrate (e.g., a PTEN protein) while simultaneously losing its activity to its native substrate (a SNAP25 protein). In some embodiments, fusion proteins described by the disclosure are useful for cleaving certain protein targets (e.g., PTEN) localized to a particular intracellular compartment, for example, a cell's plasma membrane.

Pleckstrin Homology (PH) Domains

In some aspects, the disclosure relates to fusion proteins comprising a pleckstrin homology (PH) domain. In some embodiments, a PH domain mediates binding to a biological membrane, for example, a plasma membrane of a cell. In some embodiments, a PH domain binds to phosphatidylinositol lipids within the biological membrane and/or certain proteins, such as the fr-subunits of heterotrimeric G proteins or protein kinase C. Without wishing to be bound by any particular theory, inclusion of one or more PH domains in a fusion protein enables the fusion protein to be localized to certain subcellular locations, for example, the plasma membrane of a cell.

In some embodiments, a PH domain is derived from a eukaryotic protein. In some embodiments, a PH domain comprises an amino acid sequence that is at least 80% identical to the sequence set forth in SEQ ID NO.: 2. Additional examples of PH domains include, but are not limited to, the human cytohesin-1 PH domain, human cytohesin-2 PH domain, human cytohesin-3 PH domain, and tyrosine-protein kinase BTK PH domain. Examples of PH domain amino acid sequences are set forth in SEQ ID NOs.: 18-21. In some embodiments, a PH domain comprises an amino acid sequence that is at least 80% identical to the sequence set forth in SEQ ID NOs: 18-21.

The amount or level of variation between two PH domains provided herein can be expressed as the percent identity of the nucleic acid sequences or amino acid sequences between the two nucleic acids or proteins. In some embodiments, the amount of variation is expressed as the percent identity at the amino acid sequence level. In some embodiments, the percent identity is calculated based upon a comparison of the PH domain sequence with a reference PH domain sequence (e.g., SEQ ID NO.: 2).

In some embodiments, a PH domain used in the fusion proteins described herein and the reference PH domain are from about 70% to about 99.9% identical, about 75% to about 95% identical, about 80% to about 90% identical, about 85% to about 95% identical, or about 95% to about 99% identical at the amino acid sequence level. In some embodiments, a PH domain used in the fusion proteins described herein comprises an amino acid sequence that is at least 85%, at least 90%, at least 95%, at least 99%, or at least 99.9% identical to the amino acid sequence of the PH domain represented by the amino acid sequence set forth in SEQ ID NO: 2.

In some embodiments, a PH domain used in the fusion proteins described herein comprises an amino acid sequence that is at least 85%, at least 90%, at least 95%, at least 99%, or at least 99.9% identical to the amino acid sequence of the PH domain represented by the amino acid sequence set forth in SEQ ID NO: 18.

In some embodiments, a PH domain used in the fusion proteins described herein comprises an amino acid sequence that is at least 85%, at least 90%, at least 95%, at least 99%, or at least 99.9% identical to the amino acid sequence of the PH domain represented by the amino acid sequence set forth in SEQ ID NO: 19.

In some embodiments, a PH domain used in the fusion proteins described herein comprises an amino acid sequence that is at least 85%, at least 90%, at least 95%, at least 99%, or at least 99.9% identical to the amino acid sequence of the PH domain represented by the amino acid sequence set forth in SEQ ID NO: 20.

In some embodiments, a PH domain used in the fusion proteins described herein comprises an amino acid sequence that is at least 85%, at least 90%, at least 95%, at least 99%, or at least 99.9% identical to the amino acid sequence of the PH domain represented by the amino acid sequence set forth in SEQ ID NO: 21.

Some aspects of the disclosure provide PH domains having between 1 and 20 amino acid differences (e.g., mutations, substitutions, deletions, insertions, etc.) relative to a reference PH domain (e.g., SEQ ID NO.: 2, 18, 19, 20, or 21). In some embodiments, a PH domain has 1, 2, 3, 4, 5, 6, 7, 8, 9, 10, 11, 12, 13, 14, or 15 amino acid differences relative to a reference PH domain (e.g., SEQ ID NO.: 2, 18, 19, 20, or 21).

Botulinum Neurotoxin (BoNT) Protease Variants

This disclosure provides fusion proteins comprising variants of BoNT proteases that are derived from a wild-type BoNT E protease (e.g., SEQ ID NO.: 1). In some embodiments, the BoNT protease has at least one of the amino acid variations present in Table 1 (or comprises one or more mutations at a position corresponding to the amino acid variations present in Table 1). Additional examples of BoNT proteases that can be included in fusion proteins are described in PCT Publication WO 2019/040935, published Feb. 28, 2019 and PCT Publication WO 2021/011579, published Jan. 21, 2021, the entire contents of each of which are incorporated herein by reference. In some embodiments, a BoNT protease variant is a BoNT light chain protease variant (e.g., the variant does not comprise a BoNT heavy chain peptide or polypeptide). The variation in amino acid sequence generally results from a mutation, insertion, or deletion in a DNA coding sequence. Mutation of a DNA sequence can result in a nonsense mutation (e.g., a transcription termination codon (TAA, TAG, or TAA) that produces a truncated protein), a missense mutation (e.g., an insertion or deletion mutation that shifts the reading frame of the coding sequence), or a silent mutation (e.g., a change in the coding sequence that results in a codon that codes for the same amino acid normally present in the cognate protein, also referred to sometimes as a synonymous mutation). In some embodiments, mutation of a DNA sequence results in a non-synonymous (i.e., conservative, semi-conservative, or radical) amino acid substitution.

TABLE 1

| Substitution relative to SEQ ID NO.: 1 | | | | | |
|---|---|---|---|---|---|
| C26Y | S99A/T | S163R | R244V | Q354R/W | G403E |
| Q27H | G101S | S166R | N248K | Y355P | L404* (Stop) |
| E28K | N118D | L167A | I262T | Y357F | |
| I35V | D156N | M172K | I263V | K359R | |
| G49S | E159L | I203V | A313V | N365S | |
| H56L/Y | N161Y | I232T | I316T | S367F | |
| D65G | S162Q | T242A | G353E | N390D | |

Generally, wild-type BoNT protease is encoded by a gene of the microorganism *Clostridium botulinum*. The amount or level of variation between a wild-type BoNT protease and a BoNT protease variant provided herein can be expressed as the percent identity of the nucleic acid sequences or amino acid sequences between the two genes or proteins. In some embodiments, the amount of variation is expressed as the percent identity at the amino acid sequence level. In some embodiments, the percent identity is calculated based upon the sequences of the wild-type and variant protease light chains (e.g., the heavy chain sequences are not aligned or included in the calculation of percent identity).

In some embodiments, a BoNT protease light chain variant and a wild-type BoNT protease light chain are from about 70% to about 99.9% identical, about 75% to about 95% identical, about 80% to about 90% identical, about 85% to about 95% identical, or about 95% to about 99% identical at the amino acid sequence level. In some embodiments, a BoNT protease light chain variant comprises an amino acid sequence that is at least 85%, at least 90%, at least 95%, at least 99%, or at least 99.9% identical to the amino acid sequence of a wild-type BoNT protease light chain.

In some embodiments, a variant BoNT protease is about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 99.9% identical to a wild-type BoNT protease. In some embodiments, a variant BoNT protease is not 100% identical to SEQ ID NO: 1.

Some aspects of the disclosure provide variant BoNT proteases having between about 90% and about 99.9% (e.g., about 90%, about 90.5%, about 91%, about 91.5%, about 92%, about 92.5%, about 93%, about 93.5%, about 94%, about 94.5%, about 95%, about 95.5%, about 96%, about 96.5%, about 97%, about 97.5%, about 98%, about 98.5%, about 99%, about 99.2%, about 99.4%, about 99.6%, about 99.8%, or about 99.9%) identical to a wild-type BoNT protease as set forth in SEQ ID NO.: 1. In some embodiments, the variant BoNT protease is no more than 99.9% identical to a wild-type BoNT protease.

Some aspects of the disclosure provide variant BoNT protease light chains having between 1 and 20 amino acid substitutions (e.g., mutations) relative to a wild-type BoNT protease light chain (e.g., SEQ ID NO.: 1). In some embodiments, a variant BoNT protease has 1, 2, 3, 4, 5, 6, 7, 8, 9, 10, 11, 12, 13, 14, or 15 amino acid substitutions relative to a wild-type BoNT protease (e.g., SEQ ID NO.: 1). In some embodiments, a variant BoNT protease has at least one mutation relative to a wild-type BoNT protease (e.g., SEQ ID NO.: 1).

The amount or level of variation between a wild-type BoNT protease and a variant BoNT protease can also be expressed as the number of mutations present in the amino acid sequence encoding the variant BoNT protease relative to the amino acid sequence encoding the wild-type BoNT protease. In some embodiments, an amino acid sequence encoding a variant BoNT protease comprises between about 1 mutation and about 40 mutations, about 10 mutations and about 20 mutations, about 5 mutations and about 15 mutations, about 2 mutations and about 25 mutations, or about 15 and about 30 mutations relative to an amino acid sequence encoding a wild-type BoNT protease. In some embodiments, an amino acid sequence encoding a variant BoNT protease comprises more than 40 mutations relative to an amino acid sequence encoding a wild-type BoNT protease. In some embodiments, the variant BoNT protease comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37 amino acid variations at one or more amino acid positions selected from the positions provided in Table 1. In some embodiments, the variant BoNT protease comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37 amino acid variations selected from the variations (e.g., amino acid substitutions) provided in Table 1.

Particular combinations of mutations present in an amino acid sequence encoding a variant BoNT protease light chain can be referred to as the "genotype" of the variant BoNT protease. For example, a variant BoNT E protease light chain genotype may comprise the mutations C26Y, Q27H, S99A, G101S, N118D, D156N, E159L, N161Y, S162Q, S163R, L167A, M172K, I232T, N248K, Q354R, Y355P, and Y357F, relative to a wild-type BoNT E protease (e.g., SEQ ID NO.: 1; wild-type BoNT E). In some embodiments, a fusion protein has at least 80% sequence identity (e.g., at least 70%, at least 71%, at least 72%, at least 73%, at least 74%, at least 75%, at least 76%, at least 77%, at least 78%, at least 79%, at least 80%, at least 85%, at least 90%, at least 95%, at least 96%, at least 97%, at least 98%, at least 99%, at least 99.5%, at least 99.9%, or more) to SEQ ID NO.: 5 or 6. In some embodiments, a fusion protein comprises or consists of the amino acid sequence set forth in SEQ ID NO.: 5 or 6.

This disclosure relates, in part, to the discovery that continuous evolution methods (e.g., PACE) are useful for producing BoNT protease variants that have altered peptide cleaving activities (altered peptide cleaving functions). For example, in some embodiments, a BoNT protease variant as described by the disclosure cleaves a PTEN protein or peptide. In some embodiments, a PTEN protein or peptide comprises the amino acid sequence set forth in SEQ ID NO.: 12 or 13. In some embodiments, a PTEN protein or peptide comprises an amino acid sequence that is at least 70%, 80%, 85%, 90%, 95%, 99%, or more identical to the amino acid sequence set forth in SEQ ID NO.: 12 or 13.

In some embodiments, a BoNT protease variant cleaves a target peptide (e.g., PTEN, etc.) with higher activity than a wild-type BoNT protease. A BoNT protease variant that cleaves a target peptide (e.g., PTEN, etc.) with higher activity can have an increase in catalytic efficiency ranging from about 1.1-fold, about 1.5-fold, 2-fold to about 100-fold, about 5-fold to about 50-fold, or about 10-fold to about 40-fold, relative to the catalytic efficiency of the wild-type BoNT protease from which the BoNT protease variant was derived. In some embodiments, a BoNT protease variant described herein cleaves a target peptide (e.g., PTEN, etc.) with about 1% to about 100% (e.g., about 1%, 2%, 5%, 10%, 20%, 50%, 80%, 90%, 100%) of the catalytic efficiency with which wild-type BoNT cleaves its native substrate (e.g., SNAP25, VAMP1, etc.). Catalytic efficiency can be measured or determined using any suitable method known in the art, for example, using the methods described in Harris et al. (2009) *Methods Enzymol.* 463; 57-71.

In some aspects, the disclosure relates to BoNT/E protease light chain variants comprising one or more mutations that affect substate specificity of the protease. It has been observed that position L167 (also referred to as "L166" when the wild-type BoNT/E protease sequence does not comprise an N-terminal methionine) plays an important role in SNAP25 binding and cleavage by the protease. Substituting an alanine at this position has been demonstrated to impair substrate binding and catalysis of SNAP25 by BoNT/E, as described by Chen and Barbieri, *J Biol Chem.* 2007 Aug. 31; 282(35):25540-7. Without wishing to be bound by any particular theory, inclusion of a L167A mutation in a BoNT/E protease variant light chain described herein reduces "off-target" (e.g., SNAP25) cleavage by proteases variants evolved to cleave another target (e.g., PTEN). In some embodiments, a BoNT/E protease light chain variant comprises a L167A (with respect to SEQ ID NO.: 1) substitution.

Generally, the evolution of proteases with altered specificity has focused exclusively on the destruction of therapeutically relevant extracellular proteins. However, fusion proteins comprising BoNTs described herein provide a built-in cytosolic delivery mechanism, and thus are able, in some embodiments, to degrade intracellular targets. For example, in some embodiments, a fusion protein comprising a BoNT protease variant as described herein comprises one or more protein domains that facilitate transport of the protease across a cellular membrane. In some embodiments, the one or more protein domains that facilitate transport across the membrane comprise a pleckstrin homology (PH) domain. In some embodiments, BoNT protease variants described by the disclosure are capable of crossing the cellular membrane and entering the intracellular environment of neuronal cell types.

Fusion Proteins

Aspects of the disclosure relate to fusion proteins. In some embodiments, the disclosure provides a fusion protein for use in cleaving an intracellular protein (e.g., PTEN), comprising delivering to a cell the fusion protein described herein, whereby the fusion protein contacts and cleaves the intracellular protein in the cell. A fusion protein generally refers to a protein comprising a first peptide derived from a first protein that is linked in a contiguous chain to a second peptide derived from a second protein that is different than the first protein. The first and second peptides may be linked directly (e.g., the C-terminus of the first peptide may be directly linked, such as by a peptide bond, to the N-terminus of the second peptide, or vice versa) or indirectly (e.g., the first peptide and second peptide are joined by a linking molecule, such as an amino acid or polymeric linker).

In some embodiments, a fusion protein comprises a PH domain linked to a BoNT/E protease light chain variant. In some embodiments, the PH domain and the BoNT/E protease light chain variant are directly linked together (e.g., the two peptides are bonded together without an intervening linker sequence). In some embodiments, the C-terminus of the PH domain is linked to the N-terminus of the BoNT/E protease light chain variant. In some embodiments, the BoNT/E protease light chain variant is modified to lack an N-terminal methionine residue.

In some embodiments, a PH domain is indirectly linked to a BoNT/E protease light chain variant via a linker. A linker is generally a peptide linker, for example, a glycine-rich linker (e.g., a poly-glycine-serine linker) or a proline-rich linker (e.g., a poly-Pro linker). The length of the linker may vary. In some embodiments, a linker ranges from about two amino acids in length to about 50 amino acids in length. In some embodiments, a linker comprises 2, 3, 4, 5, 6, 7, 8, 9, 10, 11, 12, 13, 14, 15, 16, 17, 18, 19, 20, 21, 22, 23, 24, or 25 amino acids. In some embodiments, a linker comprises more than 25 amino acids, for example 30, 35, 40, 45, or 50 amino acids. In some embodiments, a linker is a non-peptide linker, for example a polypropylene linker, polyethylene glycol (PEG) linker, etc.).

A fusion protein may be encoded by an isolated nucleic acid or a vector. In some embodiments, the disclosure provides an isolated nucleic acid for use in cleaving an intracellular protein, comprising delivering to a cell the isolated nucleic acid described herein, whereby the fusion protein contacts and cleaves the intracellular protein in the cell. In some embodiments, an isolated nucleic acid encoding a fusion protein further comprises one or more promoters that control expression of the fusion protein. The one or more promoters may be constitutive promoter(s), inducible promoter(s), tissue-specific promoters, or any combination of the foregoing. In some embodiments, an isolated nucleic acid encoding a fusion protein described herein further comprises a human cytomegalovirus (CMV) promoter that controls expression of the fusion protein. In some embodiments, an isolated nucleic acid encoding a fusion protein described herein further comprises a human synapsin 1 promoter that controls expression of the fusion protein.

In some embodiments, an isolated nucleic acid encoding a fusion protein is comprised in a vector, such as a plasmid or viral vector. In some embodiments, the disclosure provides a vector for use in cleaving an intracellular protein, comprising delivering to a cell the vector described herein, whereby the fusion protein contacts and cleaves the intracellular protein in the cell. In some embodiments the viral vector is a lentiviral vector. "Lentivirus" generally refers a family of retroviruses that cause chronic and severe infections in mammalian species. Lentiviruses infect and integrate their genomes into dividing and non-dividing cells (e.g., neurons). Non-limiting examples of lentiviruses used for vectors include human immunodeficiency virus (HIV), simian immunodeficiency virus (SIV), feline immunodeficiency virus (FIV), equine infectious anemia virus (EIAV), bovine immunodeficiency virus (BIV) and caprine arthritis encephalitis virus (CAEV). In some embodiments, lentiviral TRs are derived from HIV (e.g., share at least 50%, 60%, 70%, 80%, 90%, 95%, 99%, or 100% nucleic acid sequence identity with an HIV TR), for example, as described by Chung et al., *Mol Ther.* 2014 May; 22(5): 952-963.

In some aspects, provided herein is a kit comprising a container housing the fusion protein provided herein, the isolated nucleic acid provided herein, the vector provided herein, or the host cell provided herein.

Methods and Uses

Some aspects of this disclosure provide methods for using a fusion protein provided herein. In some embodiments, the methods include contacting a protein comprising a protease target cleavage sequence (e.g., PTEN cleavage sequence, SEQ ID NO: 13), for example, ex vivo, in vitro, or in vivo (e.g., in a subject), with the fusion protein, whereby the protease portion of the fusion protein cleaves the protein target. In some embodiments, the therapeutic target is PTEN. Generally, PTEN is an intracellular protein comprising a tensin domain and a phosphatase domain that functions as a tumor suppressor. PTEN has also been observed to mediate ischemic neuronal damage after a stroke. Accordingly, in some aspects, the disclosure provides methods of decreasing PTEN activity in a cell (e.g., reducing the amount of intact or functional PTEN in a cell), the method comprising contacting the cell with, or introducing into the intracellular environment, a fusion protein as described herein (e.g., a fusion protein comprising a PH domain linked to a BoNT/E variant that cleaves PTEN).

In some embodiments, the cell (or intracellular environment) is characterized by increased, aberrant, or undesired activity of a target protein (e.g., PTEN, etc.) relative to a normal cell. In some embodiments, increased activity of a target protein (e.g., PTEN, etc.) occurs when, in a cell, the activity of the target protein is about 2-fold, 3-fold, 4-fold, 5-fold, 10-fold, 25-fold, 50-fold, 100-fold, 500-fold, or 1000-fold over activity of the target protein in a normal healthy cell. In some embodiments, a cell characterized by increased expression of a target protein (e.g., PTEN, etc.) is derived from a subject (e.g., a mammalian subject, such as a human or mouse) that has or is suspected of having a disease associated with increased activity of the target gene, for example, cancer or neuronal damage in the context of PTEN overexpression or increased activity.

In some embodiments, the methods provided herein comprise contacting (e.g., cleaving) the target protein (e.g., PTEN, etc., or a protein comprising a peptide comprising an amino acid sequence that is at least 70%, 80%, 90%, 95%, 99% or more identical with the amino acid sequence set forth in SEQ ID NO.: 12 or 13) with a fusion protein described herein in vitro. In some embodiments, the methods provided herein comprise contacting the target protein with the protease variant described herein in vivo. In some embodiments, the methods provided herein comprise contacting the target protein (e.g., PTEN, etc., or a protein comprising a peptide comprising an amino acid sequence set forth in SEQ ID NO.: 12 or 13 with a fusion protein described herein in a cell or an intracellular environment. In some embodiments, the methods provided herein comprise contacting the target protein (e.g., PTEN, etc., or a protein comprising a peptide comprising an amino acid sequence set forth in SEQ ID NO.: 12 or 13 with a fusion protein in a subject, e.g., by administering the fusion protein to the subject, either locally or systemically. In some such embodiments, the fusion protein is administered to the subject in an amount effective to result in a measurable decrease in the level of full-length (or functional) target protein (e.g., etc.) in the subject, or in a measurable increase in the level of a cleavage product generated by the protease variant upon cleavage of the target protein. In some embodiments, the decrease in the level of full-length (or functional) target protein (e.g., VAMP7, etc.) is at least 10% or more (e.g., at least 10%, at least 30%, at least 40%, at least 50%, at least 60%, at least 70%, at least 80%, at least 85%, at least 90%, at least 95%, at least 96%, at least 97%, at least 98%, at least 99%, or more). In some embodiments, administration of a fusion protein described herein does not result in cleavage of proteins or peptides other than PTEN.

Host Cells

Some aspects of this invention relate to host cells for continuous evolution processes as described herein. In some embodiments, a host cell is provided that comprises at least one viral gene encoding a protein required for the generation of infectious viral particles under the control of a conditional promoter, and a fusion protein comprising a transcriptional activator targeting the conditional promoter and fused to an inhibitor via a linker comprising a protease cleavage site. For example, some embodiments provide host cells for phage-assisted continuous evolution processes, wherein the host cell comprises an accessory plasmid comprising a gene required for the generation of infectious phage particles, for example, M13 gIII, under the control of a conditional promoter, as described herein. In some embodiments, the host cells comprises an expression construct encoding a fusion protein as described herein, e.g., on the same accessory plasmid or on a separate vector. In some embodiments, the host cell further provides any phage functions that are not contained in the selection phage, e.g., in the form of a helper phage. In some embodiments, the host cell provided further comprises an expression construct comprising a gene encoding a mutagenesis-inducing protein, for example, a mutagenesis plasmid as provided herein.

In some embodiments, modified viral vectors are used in continuous evolution processes as provided herein. In some embodiments, such modified viral vectors lack a gene required for the generation of infectious viral particles. In some such embodiments, a suitable host cell is a cell comprising the gene required for the generation of infectious viral particles, for example, under the control of a constitutive or a conditional promoter (e.g., in the form of an accessory plasmid, as described herein). In some embodiments, the viral vector used lacks a plurality of viral genes. In some such embodiments, a suitable host cell is a cell that comprises a helper construct providing the viral genes required for the generation of infectious viral particles. A cell is not required to actually support the life cycle of a viral vector used in the methods provided herein. For example, a cell comprising a gene required for the generation of infectious viral particles under the control of a conditional promoter may not support the life cycle of a viral vector that does not comprise a gene of interest able to activate the promoter, but it is still a suitable host cell for such a viral vector.

In some embodiments, the host cell is a prokaryotic cell, for example, a bacterial cell. In some embodiments, the host cell is an *E. coli* cell. In some embodiments, the host cell is a eukaryotic cell, for example, a yeast cell, an insect cell, or a mammalian cell. The type of host cell, will, of course, depend on the viral vector employed, and suitable host cell/viral vector combinations will be readily apparent to those of skill in the art.

In some embodiments, the viral vector is a phage and the host cell is a bacterial cell. In some embodiments, the host cell is an *E. coli* cell. Suitable *E. coli* host strains will be apparent to those of skill in the art, and include, but are not limited to, New England Biolabs (NEB) Turbo, Top10F', DH12S, ER2738, ER2267, and XL1-Blue MRF'. These strain names are art recognized and the genotype of these strains has been well characterized. It should be understood that the above strains are exemplary only and that the invention is not limited in this respect.

In some PACE embodiments, for example, in embodiments employing an M13 selection phage, the host cells are *E. coli* cells expressing the Fertility factor, also commonly referred to as the F factor, sex factor, or F-plasmid. The F-factor is a bacterial DNA sequence that allows a bacterium to produce a sex pilus necessary for conjugation and is essential for the infection of *E. coli* cells with certain phage, for example, with M13 phage. For example, in some embodiments, the host cells for M13-PACE are of the genotype F'proA$^+$B$^+$A(lacIZY) zzf::Tn10(TetR)/endA1 recA1 galE15 galK16 nupG rpsL ΔlacIZYA araD139 Δ(ara, leu)7697 mcrA Δ(mrr-hsdRMS-mcrBC) proBA::pir116λ.

Some of the embodiments, advantages, features, and uses of the technology disclosed herein will be more fully understood from the Examples below. The Examples are intended to illustrate some of the benefits of the present disclosure and to describe particular embodiments, but are not intended to exemplify the full scope of the disclosure and, accordingly, do not limit the scope of the disclosure.

EXAMPLE

Figure 1B:
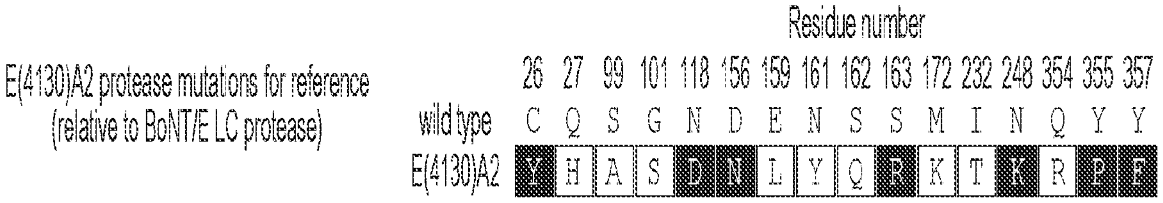
Figure 2:
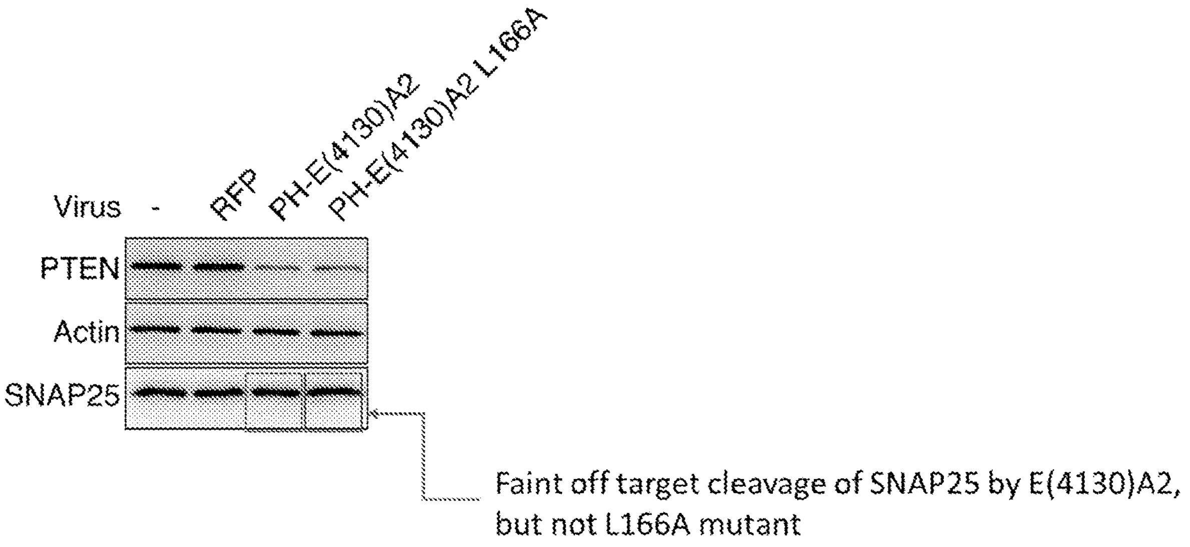
FIG. 2 shows representative data for assessment of PTEN and SNAP25 cleavage in HEK293T cells transduced with lentivirus encoding RFP (negative control), PH-E(4130)A2 protease, or the PH-E(4130)A2(L166A) mutant protease; note "L166A" referred to in this Figure corresponds to a mutation at position L167 (e.g., L167A) of SEQ ID NO: 1. After integration, cell lines were transfected with plasmids encoding HA-tagged substrates, and cleavage was visualized by Western blot.

A PACE-evolved, PTEN-cleaving protease, "E(4130) A2", was assessed by co-transfecting plasmids expressing both the protease and target PTEN into HEK293T cells. Since PTEN is trafficked to the plasma membrane in cells, a pleckstrin homology (PH) domain was fused to the N-terminus of the evolved protease to promote co-localization of the protease with its intended substrate. This modification generated "PH-E(4130)A2", which performed highly efficient cleavage of PTEN when transfected into HEK293T cells (FIGS. 1A-1B). In addition, cells were transduced with lentivirus encoding PH-E(4130)A2, and cleavage of both PTEN and SNAP25 was examined by Western blot. The transduced cells show substantial PTEN cleavage with minimal off-target cleavage of the native BoNT/E substrate SNAP25 (FIG. 2). This selectivity was further enhanced by introducing the L166A mutation (L167A, relative to SEQ ID NO.: 1), which has been observed to reduce SNAP protein cleavage by BoNTs, into PH-E(4130)A2. These results indicate that the activity of proteases emerging from PACE selections can support efficient and selective targeted proteolysis in mammalian cells.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

REPRESENTATIVE SEQUENCES

>Wild type Botulinum Neurotoxin E (BoNT/E) amino acid sequence (SEQ ID NO.: 1)
MPKINSFNYNDPVNDRTILYIKPGGCQEFYKSFNIMKNIWIIPERNVIGTTPQDFHPPTSL
KNGDSSYYDPNYLQSDEEKDRFLKIVTKIFNRINNNLSGGILLEELSKANPYLGNDNTPD
NQFHIGDASAVEIKFSNGSQHILLPNVIIMGAEPDLFETNSSNISLRNNYMPSNHGFGSIAI
VTFSPEYSFRFNDNSINEFIQDPALTLMHELIHSLHGLYGAKGITTTCIITQQQNPLITNRK
GINIEEFLTFGGNDLNIITVAQYNDIYTNLLNDYRKIASKLSKVQVSNPQLNPYKDIFQEK
YGLDKDASGIYSVNINKFDDILKKLYSFTEFDLATKFQVKCRETYIGQYKYFKLSNLLN
DSIYNISEGYNINNLKVNFRGQNANLNPRIIKPITGRGLVKKIIRF >Human phospholipase C delta 1 (PLC81) pleckstrin homology (PH) domain amino acid sequence (SEQ ID NO.: 2)
MDSGRDFLTLHGLQDDEDLQALLKGSQLLKVKSSSWRRERFYKLQEDCKTIWQESRKV
MRTPESQLFSIEDIQEVRMGHRTEGLEKFARDVPEDRCFSIVFKDQRNTLDLIAPSPADA
QHWVLGLHKIIHHSGSMDQRQKLQHWIHSCLRKADKNKDNKMSFKELQNFLK >BoNT/E (4130)A2 variant amino acid sequence (SEQ ID NO: 3)
MPKINSFNYNDPVNDRTILYIKPGGYHEFYKSFNIMKNIWIIPERNVIGTTPQDFHPPTSL
KNGDSSYYDPNYLQSDEEKDRFLKIVTKIFNRINNNLAGSILLEELSKANPYLGNDDTPD
NQFHIGDASAVEIKFSNGSQHILLPNVIIMGAEPNLFLTYQRNISLRNNYKPSNHGFGSIAI
VTFSPEYSFRFNDNSINEFIQDPALTLMHELIHSLHGLYGAKGITTTCTITQQQNPLITNRK
GIKIEEFLTFGGNDLNIITVAQYNDIYTNLLNDYRKIASKLSKVQVSNPQLNPYKDIFQEK
YGLDKDASGIYSVNINKFDDILKKLYSFTEFDLATKFQVKCRETYIGRPKFFKLSNLLND
SIYNISEGYNINNLKVNFRGQNANLNPRIIKPITGRGLVKKIIRF >BoNT/E (4130)A2-L166A variant amino acid sequence (SEQ ID NO: 4)
MPKINSFNYNDPVNDRTILYIKPGGYHEFYKSFNIMKNIWIIPERNVIGTTPQDFHPPTSL
KNGDSSYYDPNYLQSDEEKDRFLKIVTKIFNRINNNLAGSILLEELSKANPYLGNDDTPD
NQFHIGDASAVEIKFSNGSQHILLPNVIIMGAEPNLFLTYQRNISLRNNYKPSNHGFGSIAI
VTFSPEYSFRFNDNSINEFIQDPALTLMHELIHSLHGLYGAKGITTTCTITQQQNPLITNRK
GIKIEEFLTFGGNDLNIITVAQYNDIYTNLLNDYRKIASKLSKVQVSNPQLNPYKDIFQEK
YGLDKDASGIYSVNINKFDDILKKLYSFTEFDLATKFQVKCRETYIGRPKFFKLSNLLND
SIYNISEGYNINNLKVNFRGQNANLNPRIIKPITGRGLVKKIIRF >PH-BoNT/E (4130)A2 fusion protein amino acid sequence (SEQ ID NO.: 5)
MDSGRDFLTLHGLQDDEDLQALLKGSQLLKVKSSSWRRERFYKLQEDCKTIWQESRKV
MRTPESQLFSIEDIQEVRMGHRTEGLEKFARDVPEDRCFSIVFKDQRNTLDLIAPSPADA
QHWVLGLHKIIHHSGSMDQRQKLQHWIHSCLRKADKNKDNKMSFKELQNFLKGGGGS
MPKINSFNYNDPVNDRTILYIKPGGYHEFYKSFNIMKNIWIIPERNVIGTTPQDFHPPTSL
KNGDSSYYDPNYLQSDEEKDRFLKIVTKIFNRINNNLAGSILLEELSKANPYLGNDDTPD
NQFHIGDASAVEIKFSNGSQHILLPNVIIMGAEPNLFLTYQRNISLRNNYKPSNHGFGSIAI
VTFSPEYSFRFNDNSINEFIQDPALTLMHELIHSLHGLYGAKGITTTCTITQQQNPLITNRK
GIKIEEFLTFGGNDLNIITVAQYNDIYTNLLNDYRKIASKLSKVQVSNPQLNPYKDIFQEK
YGLDKDASGIYSVNINKFDDILKKLYSFTEFDLATKFQVKCRETYIGRPKFFKLSNLLND
SIYNISEGYNINNLKVNFRGQNANLNPRIIKPITGRGLVKKIIRF >PH-BoNT/E (4130)A2-L166A fusion protein amino acid sequence (SEQ ID NO.: 6)
MDSGRDFLTLHGLQDDEDLQALLKGSQLLKVKSSSWRRERFYKLQEDCKTIWQESRKV
MRTPESQLFSIEDIQEVRMGHRTEGLEKFARDVPEDRCESIVFKDQRNTLDLIAPSPADA
QHWVLGLHKIIHHSGSMDQRQKLQHWIHSCLRKADKNKDNKMSFKELQNFLKGGGGS
MPKINSFNYNDPVNDRTILYIKPGGYHEFYKSFNIMKNIWIIPERNVIGTTPQDFHPPTSL
KNGDSSYYDPNYLQSDEEKDRFLKIVTKIFNRINNNLAGSILLEELSKANPYLGNDDTPD
NQFHIGDASAVEIKFSNGSQHILLPNVIIMGAEPNLFLTYQRNISARNNYKPSNHGFGSIAI
VTFSPEYSFRFNDNSINEFIQDPALTLMHELIHSLHGLYGAKGITTTCTITQQQNPLITNRK
GIKIEEFLTFGGNDLNIITVAQYNDIYTNLLNDYRKIASKLSKVQVSNPQLNPYKDIFQEK
YGLDKDASGIYSVNINKFDDILKKLYSFTEFDLATKFQVKCRETYIGRPKFFKLSNLLND
SIYNISEGYNINNLKVNFRGQNANLNPRIIKPITGRGLVKKIIRF >Human pleckstrin homology (PH) domain nucleic acid sequence (SEQ ID NO.: 7)
ATGGACTCGGGCCGGGACTTCCTGACCCTGCACGGCCTACAGGATGATGAGGATCT
ACAGGCGCTGCTGAAGGGCAGCCAGCTCCTGAAGGTGAAGTCCAGCTCATGGAGGA
GAGAGCGCTTCTACAAGTTGCAGGAGGACTGCAAGACCATCTGGCAGGAGTCCCGC
AAGGTCATGCGGACCCCGGAGTCCCAGCTGTTCTCCATCGAGGACATTCAGGAGGT
GCGAATGGGGCACCGCACGGAGGGTCTGGAGAAGTTCGCCCGTGATGTGCCCGAGG
ACCGCTGCTTCTCCATTGTCTTCAAGGACCAGCGCAATACACTAGACCTCATCGCCC
CATCGCCAGCTGATGCCCAGCACTGGGTGCTGGGGCTGCACAAGATCATCCACCAC
TCAGGCTCCATGGACCAGCGTCAGAAGCTACAGCACTGGATTCACTCCTGCTTGCG
AAAAGCTGACAAAAACAAGGACAACAAGATGAGCTTCAAGGAGCTGCAGAACTTC
CTGAAG >BoNT/E (4130)A2 variant nucleic acid sequence (SEQ ID NO: 8)
ATGCCAAAAATCAACAGCTTTAATTACAATGACCCTGTAAACGATCGTACCATCCTA
TACATAAAGCCGGGTGGGTATCACGAGTTCTACAAATCTTTCAATATTATGAAGAAT
ATATGGATTATACCTGAGCGTAACGTTATTGGTACGACACCGCAAGATTTTCATCCA
CCTACTTCGTTGAAGAACGGTGACTCTTCCTATTACGACCCCAATTATCTCCAGTCG
GATGAAGAGAAGGACAGATTCCTTAAAATAGTAACCAAAATCTTTAACAGGATTAA
TAACAATCTAGCCGGAAGTATTTTGCTTGAAGAGCTTAGTAAAGCTAATCCTTACCT
AGGTAACGATGATACACCAGACAACCAGTTTCATATAGGCGATGCATCCGCCGTGG
AAATCAAATTTAGCAATGGATCACAGCATATTCTCTTGCCCAACGTTATTATAATGG GGGCGGAACCAAATTTATTTTTGACATATCAGAGAAATATTAGCCTGAGAAATAAC
TATAAGCCGTCAAACCATGGGTTCGGTAGCATAGCAATCGTTACTTTTTCTCCCGAA
TACAGTTTTCGCTTCAATGATAATAGTATAAATGAGTTTATCCAAGACCCCGCACTC
ACGCTTATGCACGAACTCATACACTCTTTACACGGCCTGTATGGCGCTAAGGGGATA
ACCACTACGTGTACCATTACTCAGCAACAGAACCCATTGATAACGAACAGGAAGGG
CATTAAAATCGAGGAATTTCTTACATTTGGAGGCAACGATCTGAACATTATAACTGT
CGCACAGTACAATGACATCTATACCAACTTACTAAATGATTATAGAAAAATCGCTTC
TAAGTTATCCAAGGTTCAAGTCTCAAACCCTCAACTGAATCCGTATAAGGACATATT
CCAAGAAAAATATGGATTAGACAAAGACGCGTCAGGAATCTATTCGGTAAACATTA
ACAAATTCGACGATATTTTGAAGAAACTTTACAGCTTCACGGAGTTCGACTTGGCCA
CCAAATTCCAGGTCAAATGCCGAGAGACATACATCGGACGGCCTAAGTTTTTTAAG
CTGTCGAATCTCCTGAATGATTCCATATACAACATTAGTGAGGGTTACAATATAAAT
AACCTAAAGGTGAATTTCCGAGGCCAAAACGCCAACCTAAATCCGCGTATCATTAA
ACCCATCACAGGACGGGGGTTAGTGAAGAAAATAATCCGGTTT >BoNT/E (4130)A2-L166A variant nucleic acid sequence (SEQ ID NO: 9)
ATGCCAAAAATCAACAGCTTTAATTACAATGACCCTGTAAACGATCGTACCATCCTA
TACATAAAGCCGGGTGGGTATCACGAGTTCTACAAATCTTTCAATATTATGAAGAAT
ATATGGATTATACCTGAGCGTAACGTTATTGGTACGACACCGCAAGATTTTCATCCA
CCTACTTCGTTGAAGAACGGTGACTCTTCCTATTACGACCCCAATTATCTCCAGTCG
GATGAAGAGAAGGACAGATTCCTTAAAATAGTAACCAAAATCTTTAACAGGATTAA
TAACAATCTAGCCGGAAGTATTTTGCTTGAAGAGCTTAGTAAAGCTAATCCTTACCT
AGGTAACGATGATACACCAGACAACCAGTTTCATATAGGCGATGCATCCGCCGTGG
AAATCAAATTTAGCAATGGATCACAGCATATTCTCTTGCCCAACGTTATTATAATGG
GGGCGGAACCAAATTTATTTTTGACATATCAGAGAAATATTAGCGCCAGAAATAAC
TATAAGCCGTCAAACCATGGGTTCGGTAGCATAGCAATCGTTACTTTTTCTCCCGAA
TACAGTTTTCGCTTCAATGATAATAGTATAAATGAGTTTATCCAAGACCCCGCACTC
ACGCTTATGCACGAACTCATACACTCTTTACACGGCCTGTATGGCGCTAAGGGGATA
ACCACTACGTGTACCATTACTCAGCAACAGAACCCATTGATAACGAACAGGAAGGG
CATTAAAATCGAGGAATTTCTTACATTTGGAGGCAACGATCTGAACATTATAACTGT
CGCACAGTACAATGACATCTATACCAACTTACTAAATGATTATAGAAAAATCGCTTC
TAAGTTATCCAAGGTTCAAGTCTCAAACCCTCAACTGAATCCGTATAAGGACATATT
CCAAGAAAAATATGGATTAGACAAAGACGCGTCAGGAATCTATTCGGTAAACATTA
ACAAATTCGACGATATTTTGAAGAAACTTTACAGCTTCACGGAGTTCGACTTGGCCA
CCAAATTCCAGGTCAAATGCCGAGAGACATACATCGGACGGCCTAAGTTTTTTAAG
CTGTCGAATCTCCTGAATGATTCCATATACAACATTAGTGAGGGTTACAATATAAAT
AACCTAAAGGTGAATTTCCGAGGCCAAAACGCCAACCTAAATCCGCGTATCATTAA
ACCCATCACAGGACGGGGGTTAGTGAAGAAAATAATCCGGTTT >PH-BoNT/E (4130)A2 fusion protein nucleic acid sequence (SEQ ID NO.: 10)
ATGGACTCGGGCCGGGACTTCCTGACCCTGCACGGCCTACAGGATGATGAGGATCT
ACAGGCGCTGCTGAAGGGCAGCCAGCTCCTGAAGGTGAAGTCCAGCTCATGGAGGA
GAGAGCGCTTCTACAAGTTGCAGGAGGACTGCAAGACCATCTGGCAGGAGTCCCGC
AAGGTCATGCGGACCCCGGAGTCCCAGCTGTTCTCCATCGAGGACATTCAGGAGGT
GCGAATGGGGCACCGCACGGAGGGTCTGGAGAAGTTCGCCCGTGATGTGCCCGAGG
ACCGCTGCTTCTCCATTGTCTTCAAGGACCAGCGCAATACACTAGACCTCATCGCCC
CATCGCCAGCTGATGCCCAGCACTGGGTGCTGGGGCTGCACAAGATCATCCACCAC
TCAGGCTCCATGGACCAGCGTCAGAAGCTACAGCACTGGATTCACTCCTGCTTGCG
AAAAGCTGACAAAAACAAGGACAACAAGATGAGCTTCAAGGAGCTGCAGAACTTC
CTGAAGGGTGGTGGTGGTAGCATGCCAAAAATCAACAGCTTTAATTACAATGACCC
TGTAAACGATCGTACCATCCTATACATAAAGCCGGGTGGGTATCACGAGTTCTACA
AATCTTTCAATATTATGAAGAATATATGGATTATACCTGAGCGTAACGTTATTGGTA
CGACACCGCAAGATTTTCATCCACCTACTTCGTTGAAGAACGGTGACTCTTCCTATT
ACGACCCCAATTATCTCCAGTCGGATGAAGAGAAGGACAGATTCCTTAAAATAGTA
ACCAAAATCTTTAACAGGATTAATAACAATCTAGCCGGAAGTATTTTGCTTGAAGA
GCTTAGTAAAGCTAATCCTTACCTAGGTAACGATGATACACCAGACAACCAGTTTC
ATATAGGCGATGCATCCGCCGTGGAAATCAAATTTAGCAATGGATCACAGCATATT
CTCTTGCCCAACGTTATTATAATGGGGGCGGAACCAAATTTATTTTTGACATATCAG
AGAAATATTAGCCTGAGAAATAACTATAAGCCGTCAAACCATGGGTTCGGTAGCAT
AGCAATCGTTACTTTTTCTCCCGAATACAGTTTTCGCTTCAATGATAATAGTATAAA
TGAGTTTATCCAAGACCCCGCACTCACGCTTATGCACGAACTCATACACTCTTTACA
CGGCCTGTATGGCGCTAAGGGGATAACCACTACGTGTACCATTACTCAGCAACAGA
ACCCATTGATAACGAACAGGAAGGGCATTAAAATCGAGGAATTTCTTACATTTGGA
GGCAACGATCTGAACATTATAACTGTCGCACAGTACAATGACATCTATACCAACTT
ACTAAATGATTATAGAAAAATCGCTTCTAAGTTATCCAAGGTTCAAGTCTCAAACCC
TCAACTGAATCCGTATAAGGACATATTCCAAGAAAAATATGGATTAGACAAAGACG
CGTCAGGAATCTATTCGGTAAACATTAACAAATTCGACGATATTTTGAAGAAACTTT
ACAGCTTCACGGAGTTCGACTTGGCCACCAAATTCCAGGTCAAATGCCGAGAGACA
TACATCGGACGGCCTAAGTTTTTTAAGCTGTCGAATCTCCTGAATGATTCCATATAC
AACATTAGTGAGGGTTACAATATAAATAACCTAAAGGTGAATTTCCGAGGCCAAAA
CGCCAACCTAAATCCGCGTATCATTAAACCCATCACAGGACGGGGGTTAGTGAAGA
AAATAATCCGGTTT >PH-BoNT/E (4130)A2-L166A fusion protein nucleic acid sequence (SEQ ID NO.: 11)
ATGGACTCGGGCCGGGACTTCCTGACCCTGCACGGCCTACAGGATGATGAGGATCT
ACAGGCGCTGCTGAAGGGCAGCCAGCTCCTGAAGGTGAAGTCCAGCTCATGGAGGA
GAGAGCGCTTCTACAAGTTGCAGGAGGACTGCAAGACCATCTGGCAGGAGTCCCGC
AAGGTCATGCGGACCCCGGAGTCCCAGCTGTTCTCCATCGAGGACATTCAGGAGGT
GCGAATGGGGCACCGCACGGAGGGTCTGGAGAAGTTCGCCCGTGATGTGCCCGAGG -continued ACCGCTGCTTCTCCATTGTCTTCAAGGACCAGCGCAATACACTAGACCTCATCGCCC
CATCGCCAGCTGATGCCCAGCACTGGGTGCTGGGGCTGCACAAGATCATCCACCAC
TCAGGCTCCATGGACCAGCGTCAGAAGCTACAGCACTGGATTCACTCCTGCTTGCG
AAAAGCTGACAAAAACAAGGACAACAAGATGAGCTTCAAGGAGCTGCAGAACTTC
CTGAAGGGTGGTGGTGGTAGCATGCCAAAAATCAACAGCTTTAATTACAATGACCC
TGTAAACGATCGTACCATCCTATACATAAAGCCGGGTGGGTATCACGAGTTCTACA
AATCTTTCAATATTATGAAGAATATATGGATTATACCTGAGCGTAACGTTATTGGTA
CGACACCGCAAGATTTTCATCCACCTACTTCGTTGAAGAACGGTGACTCTTCCTATT
ACGACCCCAATTATCTCCAGTCGGATGAAGAGAAGGACAGATTCCTTAAAATAGTA
ACCAAAATCTTTAACAGGATTAATAACAATCTAGCCGGAAGTATTTTGCTTGAAGA
GCTTAGTAAAGCTAATCCTTACCTAGGTAACGATGATACACCAGACAACCAGTTTC
ATATAGGCGATGCATCCGCCGTGGAAATCAAATTTAGCAATGGATCACAGCATATT
CTCTTGCCCAACGTTATTATAATGGGGGCGGAACCAAATTTATTTTTGACATATCAG
AGAAATATTAGCGCCAGAAATAACTATAAGCCGTCAAACCATGGGTTCGGTAGCAT
AGCAATCGTTACTTTTTCTCCCGAATACAGTTTTCGCTTCAATGATAATAGTATAAA
TGAGTTTATCCAAGACCCCGCACTCACGCTTATGCACGAACTCATACACTCTTTACA
CGGCCTGTATGGCGCTAAGGGGATAACCACTACGTGTACCATTACTCAGCAACAGA
ACCCATTGATAACGAACAGGAAGGGCATTAAAATCGAGGAATTTCTTACATTTGGA
GGCAACGATCTGAACATTATAACTGTCGCACAGTACAATGACATCTATACCAACTT
ACTAAATGATTATAGAAAAATCGCTTCTAAGTTATCCAAGGTTCAAGTCTCAAACCC
TCAACTGAATCCGTATAAGGACATATTCCAAGAAAAATATGGATTAGACAAAGACG
CGTCAGGAATCTATTCGGTAAACATTAACAAATTCGACGATATTTGAAGAAACTTT
ACAGCTTCACGGAGTTCGACTTGGCCACCAAATTCCAGGTCAAATGCCGAGAGACA
TACATCGGACGGCCTAAGTTTTTAAGCTGTCGAATCTCCTGAATGATTCCATATAC
AACATTAGTGAGGGTTACAATATAAATAACCTAAAGGTGAATTTCCGAGGCCAAAA
CGCCAACCTAAATCCGCGTATCATTAAACCCATCACAGGACGGGGGTTAGTGAAGA
AAATAATCCGGTTT >Human PTEN amino acid sequence (SEQ ID NO.: 12)
MTAIIKEIVSRNKRRYQEDGFDLDLTYIYPNIIAMGFPAERLEGVYRNNIDDVVRFLDSK
HKNHYKIYNLCAERHYDTAKFNCRVAQYPFEDHNPPQLELIKPFCEDLDQWLSEDDNH
VAAIHCKAGKGRTGVMICAYLLHRGKFLKAQEALDFYGEVRTRDKKGVTIPSORRYVY
YYSYLLKNHLDYRPVALLFHKMMFETIPMFSGGTCNPQFVVCQLKVKIYSSNSGPTRRE
DKFMYFEFPQPLPVCGDIKVEFFHKQNKMLKKDKMFHFWVNTFFIPGPEETSEKVENGS
LCDQEIDSICSIERADNDKEYLVLTLTKNDLDKANKDKANRYFSPNFKVKLYFTKTVE
EPSNPEASSSTSVTPDVSDNEPDHYRYSDTTDSDPENEPFDEDQHTQITKV >Minimized PTEN cleavage sequence (SEQ ID NO.: 13)
NGSLCDQEIDSICSIMEKAD >BoNT E HCN Domain (SEQ ID NO.: 14)
CKNIVSVKGIRKSICIEINNGELFFVASENSYNDDNINTPKEIDDTVTSNNNYENDLDQVI
LNFNSESAPGLSDEKLNLTIQNDAYIPKYDSNGTSDIEQHDVNELNVFFYLDAQKVPEGE
NNVNLTSSIDTALLEQPKIYTFFSSEFINNVNKPVQAALFVSWIQQVLVDFTTEANQKST
VDKIADISIVVPYIGLALNIGNEAQKGNFKDALELLGAGILLEFEPELLIPTILVFTIKSFLG
SSDNKNKVIKAINNALKERDEKWKEVYSFIVSNWMTKINTQFNKRKEQMYQALQNQV
NAIKTIIESKYNSYTLEEKNELTNKYDIKQIENELNQKVSIAMNNIDRFLTESSISYLMKLI
NEVKINKLREYDENVKTYLLNYIIQHGSILGESQQELNSMVTDTLNNSIPFKLSSYTDDKI
LISYFNKFFKRIKS (BoNT E $HC_N$, translocation domain)

>BoNT E HCC Domain (SEQ ID NO.: 15)
SSVLNMRYKNDKYVDTSGYDSNININGDVYKYPTNKNQFEIYNDKLSEVNISQNDYIIY
DNKYKNFSISFWVRIPNYDNKIVNVNNEYTIINCMRDNNSGWKVSLNHNEIIWTLQDNA
GINQKLAFNYGNANGISDYINKWIFVTITNDRLGDSKLYINGNLIDQKSILNLGNIHVSD
NILFKIVNCSYTRYIGIRYFNIFDKELDETEIQTLYSNEPNTNILKDFWGNYLLYDKEYYL
LNVLKPNNFIDRRKDSTLSINNIRSTILLANRLYSGIKVKIQRVNNSSTNDNLVRKNDQV
YINFVASKTHLFPLYADTATTNKEKTIKISSSGNRFNQVVVMNSVGNNCTMNFKNNNG
NNIGLLGFKADTVVASTWYYTHMRDHTNSNGCFWNFISEEHGWQEK (BoNT E $HC_C$,
Binding domain)

>SNAP25 substrate sequence (SEQ ID NO.: 16)
MAEDADMRNELEEMQRRADQLADESLESTRRMLQLVEESKDAGIRTLVMLDEQGEQL
ERIEEGMDQINKDMKEAEKNLTDLGKFCGLCVCPCNKLKSSDAYKKAWGNNQDGVV
ASQPARVVDEREQMAISGGFIRRVTNDARENEMDENLEQVSGIIGNLRHMALDMGNEI
DTQNRQIDRIMEKADSNKTRIDEANQRATKMLGSG >SNAP25 substate amino acid sequence (SEQ ID NO.: 17)
RQIDRIMEKA >Human cytohesin-1 PH domain amino acid sequence (SEQ ID NO.: 18)
NPDREGWLLKLGGGRVKTWKRRWFILTDNCLYYFEYTTDKEPRGIIPLENLSIREVEDS
KKPNCFELYIPDNKDQVIKACKTEADGRVVEGNHTVYRISAPTPEEKEEWIKCIKAAIS >Human cytohesin-2 PH domain amino acid sequence (SEQ ID NO.: 19)
NPDREGWLLKLGGGRVKTWKRRWFILTDNCLYYFEYTTDKEPRGIIPLENLSIREVDDP
RKPNCFELYIPNNKGQLIKACKTEADGRVVEGNHMVYRISAPTQEEKDEWIKSIQAAVS -continued >Human cytohesin-3 PH domain amino acid sequence (SEQ ID NO.: 20)
NPDREGWLLKLGGGRVKTWKRRWFILTDNCLYYFEYTTDKEPRGIIPLENLSIREVEDP
RKPNCFELYNPSHKGQVIKACKTEADGRVVEGNHVVYRISAPSPEEKEEWMKSIKASIS >Human tyrosine-protein kinase BTK PH domain amino acid sequence (SEQ ID NO.: 21)
AVILESIFLKRSQQKKKTSPLNFKKRLFLLTVHKLSYYEYDFERGRRGSKKGSIDVEKITC
VETVVPEKNPPPERQIPRRGEESSEMEQISIIERFPYPFQVVYDEGPLYVFSPTEELRKRWI
HQLKNVIR >Human PTEN nucleic acid sequence (SEQ ID NO.: 22)
ATGACAGCCATCATCAAAGAGATCGTTAGCAGAAACAAAAGGAGATATCAAGAGG
ATGGATTCGACTTAGACTTGACCTATATTTATCCAAACATTATTGCTATGGGATTTC
CTGCAGAAAGACTTGAAGGCGTATACAGGAACAATATTGATGATGTAGTAAGGTTT
TTGGATTCAAAGCATAAAAACCATTACAAGATATACAATCTTTGTGCTGAAAGACA
TTATGACACCGCCAAATTTAATTGCAGAGTTGCACAATATCCTTTTGAAGACCATAA
CCCACCACAGCTAGAACTTATCAAACCCTTTTGTGAAGATCTTGACCAATGGCTAAG
TGAAGATGACAATCATGTTGCAGCAATTCACTGTAAAGCTGGAAAGGGACGAACTG
GTGTAATGATATGTGCATATTTATTACATCGGGGCAAATTTTTAAAGGCACAAGAG
GCCCTAGATTTCTATGGGGAAGTAAGGACCAGAGACAAAAAGGGAGTAACTATTCC
CAGTCAGAGGCGCTATGTGTATTATTATAGCTACCTGTTAAAGAATCATCTGGATTA
TAGACCAGTGGCACTGTTGTTTCACAAGATGATGTTTGAAACTATTCCAATGTTCAG
TGGCGGAACTTGCAATCCTCAGTTTGTGGTCTGCCAGCTAAAGGTGAAGATATATTC
CTCCAATTCAGGACCCACACGACGGGAAGACAAGTTCATGTACTTTGAGTTCCCTCA
GCCGTTACCTGTGTGTGGTGATATCAAAGTAGAGTTCTTCCACAAACAGAACAAGA
TGCTAAAAAAGGACAAAATGTTTCACTTTTGGGTAAATACATTCTTCATACCAGGAC
CAGAGGAAACCTCAGAAAAAGTAGAAAATGGAAGTCTATGTGATCAAGAAATCGA
TAGCATTTGCAGTATAGAGCGTGCAGATAATGACAAGGAATATCTAGTACTTACTTT
AACAAAAAATGATCTTGACAAAGCAAATAAAGACAAAGCCAACCGATACTTTTCTC
CAAATTTTAAGGTGAAGCTGTACTTCACAAAAACAGTAGAGGAGCCGTCAAATCCA
GAGGCTAGCAGTTCAACTTCTGTAACACCAGATGTTAGTGACAATGAACCTGATCA
TTATAGATATTCTGACACCACTGACTCTGATCCAGAGAATGAACCTTTTGATGAAGA
TCAGCATACACAAATTACAAAAGTC >Human cytohesin-1 PH domain nucleic acid sequence (SEQ ID NO.: 23)
AATCCAGACCGAGAAGGCTGGCTATTGAAACTCGGAGGTGGCAGGGTAAAGACTTG
GAAGAGACGCTGGTTCATTCTGACTGACAACTGCCTTTACTACTTTGAGTATACCAC
GGATAAGGAGCCCCGTGGAATCATCCCTTTAGAGAATCTGAGTATCCGGGAAGTGG
AGGACTCCAAAAAACCAAACTGCTTTGAGCTTTATATCCCCGACAATAAAGACCAA
GTTATCAAGGCCTGCAAGACCGAGGCTGACGGGCGGGTGGTGGAGGGGAACCACA
CTGTTTACCGGATCTCAGCTCCGACGCCCGAGGAGAAGGAGGAGTGGATTAAGTGC
ATTAAAGCAGCCATCAGC >Human cytohesin-2 PH domain nucleic acid sequence (SEQ ID NO.: 24)
AACCCGGACCGGGAGGGCTGGCTCCTGAAGCTGGGGGGGGGGGGGTGAAGACGT
GGAAGCGGCGCTGGTTTATCCTCACAGACAACTGCCTCTACTACTTTGAGTACACCA
CGGACAAGGAGCCCCGAGGAATCATCCCCCTGGAGAATCTGAGCATCCGAGAGGTG
GACGACCCCCGGAAACCGAACTGCTTTGAACTTTACATCCCCAACAACAAGGGGCA
GCTCATCAAAGCCTGCAAAACTGAGGCGGACGGCCGAGTGGTGGAGGGAAACCAC
ATGGTGTACCGGATCTCGGCCCCCACGCAGGAGGAGAAGGACGAGTGGATCAAGTC
CATCCAGGCGGCTGTGAGT >Human cytohesin-3 PH domain nucleic acid sequence (SEQ ID NO.: 25)
AACCCCGACCGCGAGGGCTGGCTCCTGAAGCTGGGAGGGGGCCGTGTGAAGACCTG
GAAGCGCCGGTGGTTCATCCTGACCGATAACTGCCTCTATTACTTTGAATACACAAC
AGATAAGGAGCCCAGGGGAATCATCCCGTTGGAAAACCTCAGCATCAGGGAGGTG
GAGGACCCCCGGAAACCCAACTGTTTTGAGCTCTACAATCCCAGCCACAAAGGGCA
GGTCATCAAGGCCTGTAAGACTGAGGCCGACGGCCGCGTGGTAGAGGGGAACCAT
GTGGTGTACCGGATCTCAGCCCCGAGCCCGGAGGAGAAGGAGGAGTGGATGAAAT
CCATCAAAGCCAGTATCAGC >Human tyrosine-protein kinase BTK PH domain nucleic acid sequence (SEQ ID NO.: 26)
GCAGTGATTCTGGAGAGCATCTTTCTGAAGCGATCCCAACAGAAAAAGAAAACATC
ACCTCTAAACTTCAAGAAGCGCCTGTTTCTCTTGACCGTGCACAAACTCTCCTACTA
TGAGTATGACTTTGAACGTGGGAGAAGAGGCAGTAAGAAGGGTTCAATAGATGTTG
AGAAGATCACTTGTGTTGAAACAGTGGTTCCTGAAAAAAATCCTCCTCCAGAAAGA
CAGATTCCGAGAAGAGGTGAAGAGTCCAGTGAAATGGAGCAAATTTCAATCATTGA
AAGGTTCCCTTATCCCTTCCAGGTTGTATATGATGAAGGGCCTCTCTACGTCTTCTCC
CCAACTGAAGAACTAAGGAAGCGGTGGATTCACCAGCTCAAAAACGTAATCCGG

What is claimed is:

1. A fusion protein comprising:

(i) a pleckstrin homology (PH) domain; and (ii) a BoNT/E protease light chain comprising the following amino acid substitutions corresponding to SEQ ID NO: 1: C26Y, Q27H, S99A, G101S, N118D, D156N, E159L, N161Y, S162Q, S163R, M172K, I232T, N248K, Q354R, Y355P, and Y357F.

2. The fusion protein of claim 1, wherein the PH domain is a human phospholipase C delta (PLCδ) PH domain.

3. The fusion protein of claim 1, wherein the PH domain has an amino acid sequence that is at least 80% identical to the sequence set forth in any one of SEQ ID NO.: 2, or 18-21.

4. The fusion protein of claim 1, wherein the BoNT/E protease further comprises the following amino acid substitution corresponding to SEQ ID NO.: 1: L167A.

5. The fusion protein of claim 1, wherein the fusion protein has at least 80% sequence identity relative to SEQ ID NO.: 5 or 6.

6. The fusion protein of claim 1, wherein the fusion protein comprises the amino acid sequence set forth in SEQ ID NO.: 5 or 6.

7. An isolated nucleic acid encoding the fusion protein of claim 1.

8. The fusion protein of claim 1, wherein the PH domain has an amino acid sequence that is at least 90% identical to the sequence set forth in any one of SEQ ID NO.: 2, or 18-21.

9. The fusion protein of claim 1, wherein the PH domain has an amino acid sequence that is at least 95% identical to the sequence set forth in any one of SEQ ID NO.: 2, or 18-21.

10. The fusion protein of claim 1, wherein the fusion protein has at least 90% sequence identity relative to SEQ ID NO.: 5 or 6.

11. The fusion protein of claim 1, wherein the fusion protein has at least 95% sequence identity relative to SEQ ID NO.: 5 or 6.

12. The fusion protein of claim 1, wherein the PH domain is positioned N-terminal relative to the BoNT/E protease light chain.

13. The fusion protein of claim 12 further comprising a linker.

14. The fusion protein of claim 13, wherein the linker comprises a peptide linker.

15. The fusion protein of claim 14, wherein the peptide linker comprises a glycine-rich linker, a proline-rich linker, glycine/serine-rich linker, and/or alanine/glutamic acid-rich linker.

16. The fusion protein of claim 1, wherein the PH domain and the BoNT/E protease light chain are directly connected.

* * * * *

SEQUENCE LISTING

<160> NUMBER OF SEQ ID NOS: 28

<210> SEQ ID NO 1
<211> LENGTH: 411

```
<212> TYPE: PRT
<213> ORGANISM: Unknown
<220> FEATURE:
<223> OTHER INFORMATION: Botulinum Neurotoxin E

<400> SEQUENCE: 1

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln His Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Ile Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Thr Cys Ile Ile Thr Gln Gln Gln Asn Pro Leu
225                 230                 235                 240

Ile Thr Asn Arg Lys Gly Ile Asn Ile Glu Glu Phe Leu Thr Phe Gly
                245                 250                 255

Gly Asn Asp Leu Asn Ile Ile Thr Val Ala Gln Tyr Asn Asp Ile Tyr
            260                 265                 270

Thr Asn Leu Leu Asn Asp Tyr Arg Lys Ile Ala Ser Lys Leu Ser Lys
        275                 280                 285

Val Gln Val Ser Asn Pro Gln Leu Asn Pro Tyr Lys Asp Ile Phe Gln
    290                 295                 300

Glu Lys Tyr Gly Leu Asp Lys Asp Ala Ser Gly Ile Tyr Ser Val Asn
305                 310                 315                 320

Ile Asn Lys Phe Asp Asp Ile Leu Lys Lys Leu Tyr Ser Phe Thr Glu
                325                 330                 335

Phe Asp Leu Ala Thr Lys Phe Gln Val Lys Cys Arg Glu Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380
```

```
Arg Gly Gln Asn Ala Asn Leu Asn Pro Arg Ile Ile Lys Pro Ile Thr
385                 390                 395                 400

Gly Arg Gly Leu Val Lys Lys Ile Ile Arg Phe
                405                 410


<210> SEQ ID NO 2
<211> LENGTH: 170
<212> TYPE: PRT
<213> ORGANISM: Homo sapiens

<400> SEQUENCE: 2

Met Asp Ser Gly Arg Asp Phe Leu Thr Leu His Gly Leu Gln Asp Asp
1               5                   10                  15

Glu Asp Leu Gln Ala Leu Leu Lys Gly Ser Gln Leu Leu Lys Val Lys
            20                  25                  30

Ser Ser Ser Trp Arg Arg Glu Arg Phe Tyr Lys Leu Gln Glu Asp Cys
        35                  40                  45

Lys Thr Ile Trp Gln Glu Ser Arg Lys Val Met Arg Thr Pro Glu Ser
    50                  55                  60

Gln Leu Phe Ser Ile Glu Asp Ile Gln Glu Val Arg Met Gly His Arg
65                  70                  75                  80

Thr Glu Gly Leu Glu Lys Phe Ala Arg Asp Val Pro Glu Asp Arg Cys
                85                  90                  95

Phe Ser Ile Val Phe Lys Asp Gln Arg Asn Thr Leu Asp Leu Ile Ala
            100                 105                 110

Pro Ser Pro Ala Asp Ala Gln His Trp Val Leu Gly Leu His Lys Ile
        115                 120                 125

Ile His His Ser Gly Ser Met Asp Gln Arg Gln Lys Leu Gln His Trp
    130                 135                 140

Ile His Ser Cys Leu Arg Lys Ala Asp Lys Asn Lys Asp Asn Lys Met
145                 150                 155                 160

Ser Phe Lys Glu Leu Gln Asn Phe Leu Lys
                165                 170


<210> SEQ ID NO 3
<211> LENGTH: 411
<212> TYPE: PRT
<213> ORGANISM: Artificial Sequence
<220> FEATURE:
<223> OTHER INFORMATION: Synthetic

<400> SEQUENCE: 3

Met Pro Lys Ile Asn Ser Phe Asn Tyr Asn Asp Pro Val Asn Asp Arg
1               5                   10                  15

Thr Ile Leu Tyr Ile Lys Pro Gly Gly Tyr His Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ala Gly Ser Ile Leu Leu Glu Glu Leu Ser Lys Ala Asn Pro
            100                 105                 110

Tyr Leu Gly Asn Asp Asp Thr Pro Asp Asn Gln Phe His Ile Gly Asp
```

```
        115                 120                 125

Ala Ser Ala Val Glu Ile Lys Phe Ser Asn Gly Ser Gln His Ile Leu
    130                 135                 140

Leu Pro Asn Val Ile Ile Met Gly Ala Glu Pro Asn Leu Phe Leu Thr
145                 150                 155                 160

Tyr Gln Arg Asn Ile Ser Leu Arg Asn Asn Tyr Lys Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Ile Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Thr Cys Thr Ile Thr Gln Gln Gln Asn Pro Leu
225                 230                 235                 240

Ile Thr Asn Arg Lys Gly Ile Lys Ile Glu Glu Phe Leu Thr Phe Gly
                245                 250                 255

Gly Asn Asp Leu Asn Ile Ile Thr Val Ala Gln Tyr Asn Asp Ile Tyr
            260                 265                 270

Thr Asn Leu Leu Asn Asp Tyr Arg Lys Ile Ala Ser Lys Leu Ser Lys
        275                 280                 285

Val Gln Val Ser Asn Pro Gln Leu Asn Pro Tyr Lys Asp Ile Phe Gln
    290                 295                 300

Glu Lys Tyr Gly Leu Asp Lys Asp Ala Ser Gly Ile Tyr Ser Val Asn
305                 310                 315                 320

Ile Asn Lys Phe Asp Asp Ile Leu Lys Lys Leu Tyr Ser Phe Thr Glu
                325                 330                 335

Phe Asp Leu Ala Thr Lys Phe Gln Val Lys Cys Arg Glu Thr Tyr Ile
            340                 345                 350

Gly Arg Pro Lys Phe Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Lys Pro Ile Thr
385                 390                 395                 400

Gly Arg Gly Leu Val Lys Lys Ile Ile Arg Phe
                405                 410


<210> SEQ ID NO 4
<211> LENGTH: 411
<212> TYPE: PRT
<213> ORGANISM: Artificial Sequence
<220> FEATURE:
<223> OTHER INFORMATION: Synthetic

<400> SEQUENCE: 4

Met Pro Lys Ile Asn Ser Phe Asn Tyr Asn Asp Pro Val Asn Asp Arg
1               5                   10                  15

Thr Ile Leu Tyr Ile Lys Pro Gly Gly Tyr His Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
```

```
65                  70                  75                  80

Asp Arg Phe Leu Lys Ile Val Thr Lys Ile Phe Asn Arg Ile Asn Asn
                85                  90                  95

Asn Leu Ala Gly Ser Ile Leu Leu Glu Glu Leu Ser Lys Ala Asn Pro
            100                 105                 110

Tyr Leu Gly Asn Asp Asp Thr Pro Asp Asn Gln Phe His Ile Gly Asp
        115                 120                 125

Ala Ser Ala Val Glu Ile Lys Phe Ser Asn Gly Ser Gln His Ile Leu
    130                 135                 140

Leu Pro Asn Val Ile Ile Met Gly Ala Glu Pro Asn Leu Phe Leu Thr
145                 150                 155                 160

Tyr Gln Arg Asn Ile Ser Leu Arg Asn Asn Tyr Lys Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Ile Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Thr Cys Thr Ile Thr Gln Gln Gln Asn Pro Leu
225                 230                 235                 240

Ile Thr Asn Arg Lys Gly Ile Lys Ile Glu Glu Phe Leu Thr Phe Gly
                245                 250                 255

Gly Asn Asp Leu Asn Ile Ile Thr Val Ala Gln Tyr Asn Asp Ile Tyr
            260                 265                 270

Thr Asn Leu Leu Asn Asp Tyr Arg Lys Ile Ala Ser Lys Leu Ser Lys
        275                 280                 285

Val Gln Val Ser Asn Pro Gln Leu Asn Pro Tyr Lys Asp Ile Phe Gln
    290                 295                 300

Glu Lys Tyr Gly Leu Asp Lys Asp Ala Ser Gly Ile Tyr Ser Val Asn
305                 310                 315                 320

Ile Asn Lys Phe Asp Asp Ile Leu Lys Lys Leu Tyr Ser Phe Thr Glu
                325                 330                 335

Phe Asp Leu Ala Thr Lys Phe Gln Val Lys Cys Arg Glu Thr Tyr Ile
            340                 345                 350

Gly Arg Pro Lys Phe Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Lys Pro Ile Thr
385                 390                 395                 400

Gly Arg Gly Leu Val Lys Lys Ile Ile Arg Phe
                405                 410
```

<210> SEQ ID NO 5
<211> LENGTH: 586
<212> TYPE: PRT
<213> ORGANISM: Artificial Sequence
<220> FEATURE:
<223> OTHER INFORMATION: Synthetic

<400> SEQUENCE: 5

```
Met Asp Ser Gly Arg Asp Phe Leu Thr Leu His Gly Leu Gln Asp Asp
1               5                   10                  15

Glu Asp Leu Gln Ala Leu Leu Lys Gly Ser Gln Leu Leu Lys Val Lys
```

-continued

```
            20                  25                  30

Ser Ser Ser Trp Arg Arg Glu Arg Phe Tyr Lys Leu Gln Glu Asp Cys
        35                  40                  45

Lys Thr Ile Trp Gln Glu Ser Arg Lys Val Met Arg Thr Pro Glu Ser
    50                  55                  60

Gln Leu Phe Ser Ile Glu Asp Ile Gln Glu Val Arg Met Gly His Arg
65                  70                  75                  80

Thr Glu Gly Leu Glu Lys Phe Ala Arg Asp Val Pro Glu Asp Arg Cys
                85                  90                  95

Phe Ser Ile Val Phe Lys Asp Gln Arg Asn Thr Leu Asp Leu Ile Ala
            100                 105                 110

Pro Ser Pro Ala Asp Ala Gln His Trp Val Leu Gly Leu His Lys Ile
        115                 120                 125

Ile His His Ser Gly Ser Met Asp Gln Arg Gln Lys Leu Gln His Trp
    130                 135                 140

Ile His Ser Cys Leu Arg Lys Ala Asp Lys Asn Lys Asp Asn Lys Met
145                 150                 155                 160

Ser Phe Lys Glu Leu Gln Asn Phe Leu Lys Gly Gly Gly Gly Ser Met
                165                 170                 175

Pro Lys Ile Asn Ser Phe Asn Tyr Asn Asp Pro Val Asn Asp Arg Thr
            180                 185                 190

Ile Leu Tyr Ile Lys Pro Gly Gly Tyr His Glu Phe Tyr Lys Ser Phe
        195                 200                 205

Asn Ile Met Lys Asn Ile Trp Ile Ile Pro Glu Arg Asn Val Ile Gly
    210                 215                 220

Thr Thr Pro Gln Asp Phe His Pro Pro Thr Ser Leu Lys Asn Gly Asp
225                 230                 235                 240

Ser Ser Tyr Tyr Asp Pro Asn Tyr Leu Gln Ser Asp Glu Glu Lys Asp
                245                 250                 255

Arg Phe Leu Lys Ile Val Thr Lys Ile Phe Asn Arg Ile Asn Asn Asn
            260                 265                 270

Leu Ala Gly Ser Ile Leu Leu Glu Glu Leu Ser Lys Ala Asn Pro Tyr
        275                 280                 285

Leu Gly Asn Asp Asp Thr Pro Asp Asn Gln Phe His Ile Gly Asp Ala
    290                 295                 300

Ser Ala Val Glu Ile Lys Phe Ser Asn Gly Ser Gln His Ile Leu Leu
305                 310                 315                 320

Pro Asn Val Ile Ile Met Gly Ala Glu Pro Asn Leu Phe Leu Thr Tyr
                325                 330                 335

Gln Arg Asn Ile Ser Leu Arg Asn Asn Tyr Lys Pro Ser Asn His Gly
            340                 345                 350

Phe Gly Ser Ile Ala Ile Val Thr Phe Ser Pro Glu Tyr Ser Phe Arg
        355                 360                 365

Phe Asn Asp Asn Ser Ile Asn Glu Phe Ile Gln Asp Pro Ala Leu Thr
    370                 375                 380

Leu Met His Glu Leu Ile His Ser Leu His Gly Leu Tyr Gly Ala Lys
385                 390                 395                 400

Gly Ile Thr Thr Thr Cys Thr Ile Thr Gln Gln Gln Asn Pro Leu Ile
                405                 410                 415

Thr Asn Arg Lys Gly Ile Lys Ile Glu Glu Phe Leu Thr Phe Gly Gly
            420                 425                 430

Asn Asp Leu Asn Ile Ile Thr Val Ala Gln Tyr Asn Asp Ile Tyr Thr
        435                 440                 445
```

```
Asn Leu Leu Asn Asp Tyr Arg Lys Ile Ala Ser Lys Leu Ser Lys Val
    450                 455                 460

Gln Val Ser Asn Pro Gln Leu Asn Pro Tyr Lys Asp Ile Phe Gln Glu
465                 470                 475                 480

Lys Tyr Gly Leu Asp Lys Asp Ala Ser Gly Ile Tyr Ser Val Asn Ile
                485                 490                 495

Asn Lys Phe Asp Asp Ile Leu Lys Lys Leu Tyr Ser Phe Thr Glu Phe
            500                 505                 510

Asp Leu Ala Thr Lys Phe Gln Val Lys Cys Arg Glu Thr Tyr Ile Gly
        515                 520                 525

Arg Pro Lys Phe Phe Lys Leu Ser Asn Leu Leu Asn Asp Ser Ile Tyr
    530                 535                 540

Asn Ile Ser Glu Gly Tyr Asn Ile Asn Asn Leu Lys Val Asn Phe Arg
545                 550                 555                 560

Gly Gln Asn Ala Asn Leu Asn Pro Arg Ile Ile Lys Pro Ile Thr Gly
                565                 570                 575

Arg Gly Leu Val Lys Lys Ile Ile Arg Phe
            580                 585


<210> SEQ ID NO 6
<211> LENGTH: 586
<212> TYPE: PRT
<213> ORGANISM: Artificial Sequence
<220> FEATURE:
<223> OTHER INFORMATION: Synthetic

<400> SEQUENCE: 6

Met Asp Ser Gly Arg Asp Phe Leu Thr Leu His Gly Leu Gln Asp Asp
1               5                   10                  15

Glu Asp Leu Gln Ala Leu Leu Lys Gly Ser Gln Leu Leu Lys Val Lys
            20                  25                  30

Ser Ser Ser Trp Arg Arg Glu Arg Phe Tyr Lys Leu Gln Glu Asp Cys
        35                  40                  45

Lys Thr Ile Trp Gln Glu Ser Arg Lys Val Met Arg Thr Pro Glu Ser
    50                  55                  60

Gln Leu Phe Ser Ile Glu Asp Ile Gln Glu Val Arg Met Gly His Arg
65                  70                  75                  80

Thr Glu Gly Leu Glu Lys Phe Ala Arg Asp Val Pro Glu Asp Arg Cys
                85                  90                  95

Phe Ser Ile Val Phe Lys Asp Gln Arg Asn Thr Leu Asp Leu Ile Ala
            100                 105                 110

Pro Ser Pro Ala Asp Ala Gln His Trp Val Leu Gly Leu His Lys Ile
        115                 120                 125

Ile His His Ser Gly Ser Met Asp Gln Arg Gln Lys Leu Gln His Trp
    130                 135                 140

Ile His Ser Cys Leu Arg Lys Ala Asp Lys Asn Lys Asp Asn Lys Met
145                 150                 155                 160

Ser Phe Lys Glu Leu Gln Asn Phe Leu Lys Gly Gly Gly Gly Ser Met
                165                 170                 175

Pro Lys Ile Asn Ser Phe Asn Tyr Asn Asp Pro Val Asn Asp Arg Thr
            180                 185                 190

Ile Leu Tyr Ile Lys Pro Gly Gly Tyr His Glu Phe Tyr Lys Ser Phe
        195                 200                 205

Asn Ile Met Lys Asn Ile Trp Ile Ile Pro Glu Arg Asn Val Ile Gly
    210                 215                 220
```

Thr Thr Pro Gln Asp Phe His Pro Pro Thr Ser Leu Lys Asn Gly Asp
225 230 235 240

Ser Ser Tyr Tyr Asp Pro Asn Tyr Leu Gln Ser Asp Glu Glu Lys Asp
245 250 255

Arg Phe Leu Lys Ile Val Thr Lys Ile Phe Asn Arg Ile Asn Asn Asn
260 265 270

Leu Ala Gly Ser Ile Leu Leu Glu Glu Leu Ser Lys Ala Asn Pro Tyr
275 280 285

Leu Gly Asn Asp Asp Thr Pro Asp Asn Gln Phe His Ile Gly Asp Ala
290 295 300

Ser Ala Val Glu Ile Lys Phe Ser Asn Gly Ser Gln His Ile Leu Leu
305 310 315 320

Pro Asn Val Ile Ile Met Gly Ala Glu Pro Asn Leu Phe Leu Thr Tyr
325 330 335

Gln Arg Asn Ile Ser Ala Arg Asn Asn Tyr Lys Pro Ser Asn His Gly
340 345 350

Phe Gly Ser Ile Ala Ile Val Thr Phe Ser Pro Glu Tyr Ser Phe Arg
355 360 365

Phe Asn Asp Asn Ser Ile Asn Glu Phe Ile Gln Asp Pro Ala Leu Thr
370 375 380

Leu Met His Glu Leu Ile His Ser Leu His Gly Leu Tyr Gly Ala Lys
385 390 395 400

Gly Ile Thr Thr Thr Cys Thr Ile Thr Gln Gln Gln Asn Pro Leu Ile
405 410 415

Thr Asn Arg Lys Gly Ile Lys Ile Glu Glu Phe Leu Thr Phe Gly Gly
420 425 430

Asn Asp Leu Asn Ile Ile Thr Val Ala Gln Tyr Asn Asp Ile Tyr Thr
435 440 445

Asn Leu Leu Asn Asp Tyr Arg Lys Ile Ala Ser Lys Leu Ser Lys Val
450 455 460

Gln Val Ser Asn Pro Gln Leu Asn Pro Tyr Lys Asp Ile Phe Gln Glu
465 470 475 480

Lys Tyr Gly Leu Asp Lys Asp Ala Ser Gly Ile Tyr Ser Val Asn Ile
485 490 495

Asn Lys Phe Asp Asp Ile Leu Lys Lys Leu Tyr Ser Phe Thr Glu Phe
500 505 510

Asp Leu Ala Thr Lys Phe Gln Val Lys Cys Arg Glu Thr Tyr Ile Gly
515 520 525

Arg Pro Lys Phe Phe Lys Leu Ser Asn Leu Leu Asn Asp Ser Ile Tyr
530 535 540

Asn Ile Ser Glu Gly Tyr Asn Ile Asn Asn Leu Lys Val Asn Phe Arg
545 550 555 560

Gly Gln Asn Ala Asn Leu Asn Pro Arg Ile Ile Lys Pro Ile Thr Gly
565 570 575

Arg Gly Leu Val Lys Lys Ile Ile Arg Phe
580 585

<210> SEQ ID NO 7
<211> LENGTH: 510
<212> TYPE: PRT
<213> ORGANISM: Artificial Sequence
<220> FEATURE:
<223> OTHER INFORMATION: Synthetic

<400> SEQUENCE: 7

-continued

```
Ala Thr Gly Gly Ala Cys Thr Cys Gly Gly Gly Cys Cys Gly Gly Gly
1               5                   10                  15

Ala Cys Thr Thr Cys Cys Thr Gly Ala Cys Cys Cys Thr Gly Cys Ala
            20                  25                  30

Cys Gly Gly Cys Cys Thr Ala Cys Ala Gly Gly Ala Thr Gly Ala Thr
        35                  40                  45

Gly Ala Gly Gly Ala Thr Cys Thr Ala Cys Ala Gly Gly Cys Gly Cys
    50                  55                  60

Thr Gly Cys Thr Gly Ala Ala Gly Gly Gly Cys Ala Gly Cys Cys Ala
65                  70                  75                  80

Gly Cys Thr Cys Cys Thr Gly Ala Ala Gly Gly Thr Gly Ala Ala Gly
                85                  90                  95

Thr Cys Cys Ala Gly Cys Thr Cys Ala Thr Gly Gly Ala Gly Gly Ala
            100                 105                 110

Gly Ala Gly Ala Gly Cys Gly Cys Thr Thr Cys Thr Ala Cys Ala Ala
        115                 120                 125

Gly Thr Thr Gly Cys Ala Gly Gly Ala Gly Gly Ala Cys Thr Gly Cys
    130                 135                 140

Ala Ala Gly Ala Cys Cys Ala Thr Cys Thr Gly Gly Cys Ala Gly Gly
145                 150                 155                 160

Ala Gly Thr Cys Cys Cys Gly Cys Ala Ala Gly Gly Thr Cys Ala Thr
                165                 170                 175

Gly Cys Gly Gly Ala Cys Cys Cys Cys Gly Gly Ala Gly Thr Cys Cys
            180                 185                 190

Cys Ala Gly Cys Thr Gly Thr Thr Cys Thr Cys Cys Ala Thr Cys Gly
        195                 200                 205

Ala Gly Gly Ala Cys Ala Thr Thr Cys Ala Gly Gly Ala Gly Gly Thr
    210                 215                 220

Gly Cys Gly Ala Ala Thr Gly Gly Gly Gly Cys Ala Cys Cys Gly Cys
225                 230                 235                 240

Ala Cys Gly Gly Ala Gly Gly Gly Thr Cys Thr Gly Gly Ala Gly Ala
                245                 250                 255

Ala Gly Thr Thr Cys Gly Cys Cys Cys Gly Thr Gly Ala Thr Gly Thr
            260                 265                 270

Gly Cys Cys Cys Gly Ala Gly Gly Ala Cys Cys Gly Cys Thr Gly Cys
        275                 280                 285

Thr Thr Cys Thr Cys Cys Ala Thr Thr Gly Thr Cys Thr Thr Cys Ala
    290                 295                 300

Ala Gly Gly Ala Cys Cys Ala Gly Cys Gly Cys Ala Ala Thr Ala Cys
305                 310                 315                 320

Ala Cys Thr Ala Gly Ala Cys Cys Thr Cys Ala Thr Cys Gly Cys Cys
                325                 330                 335

Cys Cys Ala Thr Cys Gly Cys Cys Ala Gly Cys Thr Gly Ala Thr Gly
            340                 345                 350

Cys Cys Cys Ala Gly Cys Ala Cys Thr Gly Gly Gly Thr Gly Cys Thr
        355                 360                 365

Gly Gly Gly Gly Cys Thr Gly Cys Ala Cys Ala Ala Gly Ala Thr Cys
    370                 375                 380

Ala Thr Cys Cys Ala Cys Cys Ala Cys Thr Cys Ala Gly Gly Cys Thr
385                 390                 395                 400

Cys Cys Ala Thr Gly Gly Ala Cys Cys Ala Gly Cys Gly Thr Cys Ala
                405                 410                 415
```

```
Gly Ala Ala Gly Cys Thr Ala Cys Ala Gly Cys Ala Cys Thr Gly Gly
            420                 425                 430

Ala Thr Thr Cys Ala Cys Thr Cys Cys Thr Gly Cys Thr Thr Gly Cys
        435                 440                 445

Gly Ala Ala Ala Ala Gly Cys Thr Gly Ala Cys Ala Ala Ala Ala Ala
    450                 455                 460

Cys Ala Ala Gly Gly Ala Cys Ala Ala Cys Ala Ala Gly Ala Thr Gly
465                 470                 475                 480

Ala Gly Cys Thr Thr Cys Ala Ala Gly Gly Ala Gly Cys Thr Gly Cys
                485                 490                 495

Ala Gly Ala Ala Cys Thr Thr Cys Cys Thr Gly Ala Ala Gly
            500                 505                 510


<210> SEQ ID NO 8
<211> LENGTH: 1233
<212> TYPE: PRT
<213> ORGANISM: Artificial Sequence
<220> FEATURE:
<223> OTHER INFORMATION: Synthetic

<400> SEQUENCE: 8

Ala Thr Gly Cys Cys Ala Ala Ala Ala Ala Thr Cys Ala Ala Cys Ala
1               5                   10                  15

Gly Cys Thr Thr Thr Ala Ala Thr Thr Ala Cys Ala Ala Thr Gly Ala
            20                  25                  30

Cys Cys Cys Thr Gly Thr Ala Ala Ala Cys Gly Ala Thr Cys Gly Thr
        35                  40                  45

Ala Cys Cys Ala Thr Cys Cys Thr Ala Thr Ala Cys Ala Thr Ala Ala
    50                  55                  60

Ala Gly Cys Cys Gly Gly Gly Thr Gly Gly Gly Thr Ala Thr Cys Ala
65                  70                  75                  80

Cys Gly Ala Gly Thr Thr Cys Thr Ala Cys Ala Ala Ala Thr Cys Thr
                85                  90                  95

Thr Thr Cys Ala Ala Thr Ala Thr Thr Ala Thr Gly Ala Ala Gly Ala
            100                 105                 110

Ala Thr Ala Thr Ala Thr Gly Gly Ala Thr Thr Ala Thr Ala Cys Cys
        115                 120                 125

Thr Gly Ala Gly Cys Gly Thr Ala Ala Cys Gly Thr Thr Ala Thr Thr
    130                 135                 140

Gly Gly Thr Ala Cys Gly Ala Cys Ala Cys Cys Gly Cys Ala Ala Gly
145                 150                 155                 160

Ala Thr Thr Thr Thr Cys Ala Thr Cys Cys Ala Cys Cys Thr Ala Cys
                165                 170                 175

Thr Thr Cys Gly Thr Thr Gly Ala Ala Gly Ala Ala Cys Gly Gly Thr
            180                 185                 190

Gly Ala Cys Thr Cys Thr Thr Cys Cys Thr Ala Thr Thr Ala Cys Gly
        195                 200                 205

Ala Cys Cys Cys Cys Ala Ala Thr Thr Ala Thr Cys Thr Cys Cys Ala
    210                 215                 220

Gly Thr Cys Gly Gly Ala Thr Gly Ala Ala Gly Ala Gly Ala Ala Gly
225                 230                 235                 240

Gly Ala Cys Ala Gly Ala Thr Thr Cys Cys Thr Thr Ala Ala Ala Ala
                245                 250                 255

Thr Ala Gly Thr Ala Ala Cys Cys Ala Ala Ala Ala Thr Cys Thr Thr
            260                 265                 270
```

```
Thr Ala Ala Cys Ala Gly Gly Ala Thr Thr Ala Ala Thr Ala Ala Cys
        275                 280                 285

Ala Ala Thr Cys Thr Ala Gly Cys Cys Gly Gly Ala Ala Gly Thr Ala
    290                 295                 300

Thr Thr Thr Thr Gly Cys Thr Thr Gly Ala Ala Gly Ala Gly Cys Thr
305                 310                 315                 320

Thr Ala Gly Thr Ala Ala Ala Gly Cys Thr Ala Ala Thr Cys Cys Thr
                325                 330                 335

Thr Ala Cys Cys Thr Ala Gly Gly Thr Ala Ala Cys Gly Ala Thr Gly
            340                 345                 350

Ala Thr Ala Cys Ala Cys Cys Ala Gly Ala Cys Ala Ala Cys Cys Ala
        355                 360                 365

Gly Thr Thr Thr Cys Ala Thr Ala Thr Ala Gly Gly Cys Gly Ala Thr
    370                 375                 380

Gly Cys Ala Thr Cys Cys Gly Cys Cys Gly Thr Gly Gly Ala Ala Ala
385                 390                 395                 400

Thr Cys Ala Ala Ala Thr Thr Thr Ala Gly Cys Ala Ala Thr Gly Gly
                405                 410                 415

Ala Thr Cys Ala Cys Ala Gly Cys Ala Thr Ala Thr Thr Cys Thr Cys
            420                 425                 430

Thr Thr Gly Cys Cys Cys Ala Ala Cys Gly Thr Thr Ala Thr Thr Ala
        435                 440                 445

Thr Ala Ala Thr Gly Gly Gly Gly Gly Cys Gly Gly Ala Ala Cys Cys
    450                 455                 460

Ala Ala Ala Thr Thr Thr Ala Thr Thr Thr Thr Thr Gly Ala Cys Ala
465                 470                 475                 480

Thr Ala Thr Cys Ala Gly Ala Gly Ala Ala Ala Thr Ala Thr Thr Ala
                485                 490                 495

Gly Cys Cys Thr Gly Ala Gly Ala Ala Ala Thr Ala Ala Cys Thr Ala
            500                 505                 510

Thr Ala Ala Gly Cys Cys Gly Thr Cys Ala Ala Ala Cys Cys Ala Thr
        515                 520                 525

Gly Gly Gly Thr Thr Cys Gly Gly Thr Ala Gly Cys Ala Thr Ala Gly
    530                 535                 540

Cys Ala Ala Thr Cys Gly Thr Thr Ala Cys Thr Thr Thr Thr Thr Cys
545                 550                 555                 560

Thr Cys Cys Cys Gly Ala Ala Thr Ala Cys Ala Gly Thr Thr Thr Thr
                565                 570                 575

Cys Gly Cys Thr Thr Cys Ala Ala Thr Gly Ala Thr Ala Ala Thr Ala
            580                 585                 590

Gly Thr Ala Thr Ala Ala Ala Thr Gly Ala Gly Thr Thr Thr Ala Thr
        595                 600                 605

Cys Cys Ala Ala Gly Ala Cys Cys Cys Cys Gly Cys Ala Cys Thr Cys
    610                 615                 620

Ala Cys Gly Cys Thr Thr Ala Thr Gly Cys Ala Cys Gly Ala Ala Cys
625                 630                 635                 640

Thr Cys Ala Thr Ala Cys Ala Cys Thr Cys Thr Thr Thr Ala Cys Ala
                645                 650                 655

Cys Gly Gly Cys Cys Thr Gly Thr Ala Thr Gly Gly Cys Gly Cys Thr
            660                 665                 670

Ala Ala Gly Gly Gly Gly Ala Thr Ala Ala Cys Cys Ala Cys Thr Ala
        675                 680                 685

Cys Gly Thr Gly Thr Ala Cys Cys Ala Thr Thr Ala Cys Thr Cys Ala
```

```
    690                 695                 700

Gly Cys Ala Ala Cys Ala Gly Ala Ala Cys Cys Cys Ala Thr Thr Gly
705                 710                 715                 720

Ala Thr Ala Ala Cys Gly Ala Ala Cys Ala Gly Gly Ala Ala Gly Gly
                725                 730                 735

Gly Cys Ala Thr Thr Ala Ala Ala Ala Thr Cys Gly Ala Gly Gly Ala
            740                 745                 750

Ala Thr Thr Thr Cys Thr Thr Ala Cys Ala Thr Thr Thr Gly Gly Ala
        755                 760                 765

Gly Gly Cys Ala Ala Cys Gly Ala Thr Cys Thr Gly Ala Ala Cys Ala
    770                 775                 780

Thr Thr Ala Thr Ala Ala Cys Thr Gly Thr Cys Gly Cys Ala Cys Ala
785                 790                 795                 800

Gly Thr Ala Cys Ala Ala Thr Gly Ala Cys Ala Thr Cys Thr Ala Thr
                805                 810                 815

Ala Cys Cys Ala Ala Cys Thr Thr Ala Cys Thr Ala Ala Ala Thr Gly
            820                 825                 830

Ala Thr Thr Ala Thr Ala Gly Ala Ala Ala Ala Ala Thr Cys Gly Cys
        835                 840                 845

Thr Thr Cys Thr Ala Ala Gly Thr Thr Ala Thr Cys Cys Ala Ala Gly
    850                 855                 860

Gly Thr Thr Cys Ala Ala Gly Thr Cys Thr Cys Ala Ala Ala Cys Cys
865                 870                 875                 880

Cys Thr Cys Ala Ala Cys Thr Gly Ala Ala Thr Cys Cys Gly Thr Ala
                885                 890                 895

Thr Ala Ala Gly Gly Ala Cys Ala Thr Ala Thr Thr Cys Cys Ala Ala
            900                 905                 910

Gly Ala Ala Ala Ala Ala Thr Ala Thr Gly Gly Ala Thr Thr Ala Gly
        915                 920                 925

Ala Cys Ala Ala Ala Gly Ala Cys Gly Cys Gly Thr Cys Ala Gly Gly
    930                 935                 940

Ala Ala Thr Cys Thr Ala Thr Thr Cys Gly Gly Thr Ala Ala Ala Cys
945                 950                 955                 960

Ala Thr Thr Ala Ala Cys Ala Ala Ala Thr Thr Cys Gly Ala Cys Gly
                965                 970                 975

Ala Thr Ala Thr Thr Thr Thr Gly Ala Ala Gly Ala Ala Ala Cys Thr
            980                 985                 990

Thr Thr Ala Cys Ala Gly Cys Thr  Thr Cys Ala Cys Gly  Gly Ala Gly
        995                 1000                1005

Thr Thr  Cys Gly Ala Cys Thr  Thr Gly Gly Cys Cys  Ala Cys Cys
    1010                1015                1020

Ala Ala  Ala Thr Thr Cys Cys  Ala Gly Gly Thr Cys  Ala Ala Ala
    1025                1030                1035

Thr Gly  Cys Cys Gly Ala Gly  Ala Gly Ala Cys Ala  Thr Ala Cys
    1040                1045                1050

Ala Thr  Cys Gly Gly Ala Cys  Gly Gly Cys Cys Thr  Ala Ala Gly
    1055                1060                1065

Thr Thr  Thr Thr Thr Thr Ala  Ala Gly Cys Thr Gly  Thr Cys Gly
    1070                1075                1080

Ala Ala  Thr Cys Thr Cys Cys  Thr Gly Ala Ala Thr  Gly Ala Thr
    1085                1090                1095

Thr Cys  Cys Ala Thr Ala Thr  Ala Cys Ala Ala Cys  Ala Thr Thr
    1100                1105                1110
```

```
Ala Gly  Thr Gly Ala Gly Gly  Gly Thr Thr Ala Cys  Ala Ala Thr
    1115                 1120                 1125

Ala Thr  Ala Ala Ala Thr Ala  Ala Cys Cys Thr Ala  Ala Ala Gly
    1130                 1135                 1140

Gly Thr  Gly Ala Ala Thr Thr  Thr Cys Cys Gly Ala  Gly Gly Cys
    1145                 1150                 1155

Cys Ala  Ala Ala Ala Cys Gly  Cys Cys Ala Ala Cys  Cys Thr Ala
    1160                 1165                 1170

Ala Ala  Thr Cys Cys Gly Cys  Gly Thr Ala Thr Cys  Ala Thr Thr
    1175                 1180                 1185

Ala Ala  Ala Cys Cys Cys Ala  Thr Cys Ala Cys Ala  Gly Gly Ala
    1190                 1195                 1200

Cys Gly  Gly Gly Gly Gly Thr  Thr Ala Gly Thr Gly  Ala Ala Gly
    1205                 1210                 1215

Ala Ala  Ala Ala Thr Ala Ala  Thr Cys Cys Gly Gly  Thr Thr Thr
    1220                 1225                 1230


<210> SEQ ID NO 9
<211> LENGTH: 1233
<212> TYPE: PRT
<213> ORGANISM: Artificial Sequence
<220> FEATURE:
<223> OTHER INFORMATION: Synthetic

<400> SEQUENCE: 9

Ala Thr Gly Cys Cys Ala Ala Ala Ala Ala Thr Cys Ala Ala Cys Ala
1               5                   10                  15

Gly Cys Thr Thr Thr Ala Ala Thr Thr Ala Cys Ala Ala Thr Gly Ala
            20                  25                  30

Cys Cys Cys Thr Gly Thr Ala Ala Ala Cys Gly Ala Thr Cys Gly Thr
        35                  40                  45

Ala Cys Cys Ala Thr Cys Cys Thr Ala Thr Ala Cys Ala Thr Ala Ala
    50                  55                  60

Ala Gly Cys Cys Gly Gly Gly Thr Gly Gly Gly Thr Ala Thr Cys Ala
65                  70                  75                  80

Cys Gly Ala Gly Thr Thr Cys Thr Ala Cys Ala Ala Ala Thr Cys Thr
                85                  90                  95

Thr Thr Cys Ala Ala Thr Ala Thr Thr Ala Thr Gly Ala Ala Gly Ala
            100                 105                 110

Ala Thr Ala Thr Ala Thr Gly Gly Ala Thr Thr Ala Thr Ala Cys Cys
        115                 120                 125

Thr Gly Ala Gly Cys Gly Thr Ala Ala Cys Gly Thr Thr Ala Thr Thr
    130                 135                 140

Gly Gly Thr Ala Cys Gly Ala Cys Ala Cys Cys Gly Cys Ala Ala Gly
145                 150                 155                 160

Ala Thr Thr Thr Thr Cys Ala Thr Cys Cys Ala Cys Cys Thr Ala Cys
                165                 170                 175

Thr Thr Cys Gly Thr Thr Gly Ala Ala Gly Ala Ala Cys Gly Gly Thr
            180                 185                 190

Gly Ala Cys Thr Cys Thr Thr Cys Cys Thr Ala Thr Thr Ala Cys Gly
        195                 200                 205

Ala Cys Cys Cys Cys Ala Ala Thr Thr Ala Thr Cys Thr Cys Cys Ala
    210                 215                 220

Gly Thr Cys Gly Gly Ala Thr Gly Ala Ala Gly Ala Gly Ala Ala Gly
225                 230                 235                 240
```

```
Gly Ala Cys Ala Gly Ala Thr Thr Cys Cys Thr Thr Ala Ala Ala Ala
                245                 250                 255

Thr Ala Gly Thr Ala Ala Cys Cys Ala Ala Ala Ala Thr Cys Thr Thr
            260                 265                 270

Thr Ala Ala Cys Ala Gly Gly Ala Thr Thr Ala Ala Thr Ala Ala Cys
        275                 280                 285

Ala Ala Thr Cys Thr Ala Gly Cys Cys Gly Gly Ala Ala Gly Thr Ala
    290                 295                 300

Thr Thr Thr Thr Gly Cys Thr Thr Gly Ala Ala Gly Ala Gly Cys Thr
305                 310                 315                 320

Thr Ala Gly Thr Ala Ala Ala Gly Cys Thr Ala Ala Thr Cys Cys Thr
                325                 330                 335

Thr Ala Cys Cys Thr Ala Gly Gly Thr Ala Ala Cys Gly Ala Thr Gly
            340                 345                 350

Ala Thr Ala Cys Ala Cys Cys Ala Gly Ala Cys Ala Ala Cys Cys Ala
        355                 360                 365

Gly Thr Thr Thr Cys Ala Thr Ala Thr Ala Gly Gly Cys Gly Ala Thr
    370                 375                 380

Gly Cys Ala Thr Cys Cys Gly Cys Cys Gly Thr Gly Gly Ala Ala Ala
385                 390                 395                 400

Thr Cys Ala Ala Ala Thr Thr Thr Ala Gly Cys Ala Ala Thr Gly Gly
                405                 410                 415

Ala Thr Cys Ala Cys Ala Gly Cys Ala Thr Ala Thr Thr Cys Thr Cys
            420                 425                 430

Thr Thr Gly Cys Cys Cys Ala Ala Cys Gly Thr Thr Ala Thr Thr Ala
        435                 440                 445

Thr Ala Ala Thr Gly Gly Gly Gly Gly Cys Gly Gly Ala Ala Cys Cys
    450                 455                 460

Ala Ala Ala Thr Thr Thr Ala Thr Thr Thr Thr Thr Gly Ala Cys Ala
465                 470                 475                 480

Thr Ala Thr Cys Ala Gly Ala Gly Ala Ala Ala Thr Ala Thr Thr Ala
                485                 490                 495

Gly Cys Gly Cys Cys Ala Gly Ala Ala Ala Thr Ala Ala Cys Thr Ala
            500                 505                 510

Thr Ala Ala Gly Cys Cys Gly Thr Cys Ala Ala Ala Cys Cys Ala Thr
        515                 520                 525

Gly Gly Gly Thr Thr Cys Gly Gly Thr Ala Gly Cys Ala Thr Ala Gly
    530                 535                 540

Cys Ala Ala Thr Cys Gly Thr Thr Ala Cys Thr Thr Thr Thr Thr Cys
545                 550                 555                 560

Thr Cys Cys Cys Gly Ala Ala Thr Ala Cys Ala Gly Thr Thr Thr Thr
                565                 570                 575

Cys Gly Cys Thr Thr Cys Ala Ala Thr Gly Ala Thr Ala Ala Thr Ala
            580                 585                 590

Gly Thr Ala Thr Ala Ala Ala Thr Gly Ala Gly Thr Thr Thr Ala Thr
        595                 600                 605

Cys Cys Ala Ala Gly Ala Cys Cys Cys Cys Gly Cys Ala Cys Thr Cys
    610                 615                 620

Ala Cys Gly Cys Thr Thr Ala Thr Gly Cys Ala Cys Gly Ala Ala Cys
625                 630                 635                 640

Thr Cys Ala Thr Ala Cys Ala Cys Thr Cys Thr Thr Thr Ala Cys Ala
                645                 650                 655
```

```
Cys Gly Gly Cys Cys Thr Gly Thr Ala Thr Gly Gly Cys Gly Cys Thr
            660                 665                 670

Ala Ala Gly Gly Gly Gly Ala Thr Ala Ala Cys Cys Ala Cys Thr Ala
        675                 680                 685

Cys Gly Thr Gly Thr Ala Cys Cys Ala Thr Thr Ala Cys Thr Cys Ala
    690                 695                 700

Gly Cys Ala Ala Cys Ala Gly Ala Ala Cys Cys Cys Ala Thr Thr Gly
705                 710                 715                 720

Ala Thr Ala Ala Cys Gly Ala Ala Cys Ala Gly Gly Ala Ala Gly Gly
                725                 730                 735

Gly Cys Ala Thr Thr Ala Ala Ala Ala Thr Cys Gly Ala Gly Gly Ala
            740                 745                 750

Ala Thr Thr Thr Cys Thr Thr Ala Cys Ala Thr Thr Thr Gly Gly Ala
        755                 760                 765

Gly Gly Cys Ala Ala Cys Gly Ala Thr Cys Thr Gly Ala Ala Cys Ala
    770                 775                 780

Thr Thr Ala Thr Ala Ala Cys Thr Gly Thr Cys Gly Cys Ala Cys Ala
785                 790                 795                 800

Gly Thr Ala Cys Ala Ala Thr Gly Ala Cys Ala Thr Cys Thr Ala Thr
                805                 810                 815

Ala Cys Cys Ala Ala Cys Thr Thr Ala Cys Thr Ala Ala Ala Thr Gly
            820                 825                 830

Ala Thr Thr Ala Thr Ala Gly Ala Ala Ala Ala Ala Thr Cys Gly Cys
        835                 840                 845

Thr Thr Cys Thr Ala Ala Gly Thr Thr Ala Thr Cys Cys Ala Ala Gly
    850                 855                 860

Gly Thr Thr Cys Ala Ala Gly Thr Cys Thr Cys Ala Ala Ala Cys Cys
865                 870                 875                 880

Cys Thr Cys Ala Ala Cys Thr Gly Ala Ala Thr Cys Cys Gly Thr Ala
                885                 890                 895

Thr Ala Ala Gly Gly Ala Cys Ala Thr Ala Thr Thr Cys Cys Ala Ala
            900                 905                 910

Gly Ala Ala Ala Ala Ala Thr Ala Thr Gly Gly Ala Thr Thr Ala Gly
        915                 920                 925

Ala Cys Ala Ala Ala Gly Ala Cys Gly Cys Gly Thr Cys Ala Gly Gly
    930                 935                 940

Ala Ala Thr Cys Thr Ala Thr Thr Cys Gly Gly Thr Ala Ala Ala Cys
945                 950                 955                 960

Ala Thr Thr Ala Ala Cys Ala Ala Ala Thr Thr Cys Gly Ala Cys Gly
                965                 970                 975

Ala Thr Ala Thr Thr Thr Thr Gly Ala Ala Gly Ala Ala Ala Cys Thr
            980                 985                 990

Thr Thr Ala Cys Ala Gly Cys Thr  Thr Cys Ala Cys Gly  Gly Ala Gly
        995                 1000                1005

Thr Thr  Cys Gly Ala Cys Thr  Thr Gly Gly Cys Cys  Ala Cys Cys
    1010                1015                1020

Ala Ala  Ala Thr Thr Cys Cys  Ala Gly Gly Thr Cys  Ala Ala Ala
    1025                1030                1035

Thr Gly  Cys Cys Gly Ala Gly  Ala Gly Ala Cys Ala  Thr Ala Cys
    1040                1045                1050

Ala Thr  Cys Gly Gly Ala Cys  Gly Gly Cys Cys Thr  Ala Ala Gly
    1055                1060                1065

Thr Thr  Thr Thr Thr Thr Ala  Ala Gly Cys Thr Gly  Thr Cys Gly
```

1070 1075 1080

Ala Ala Thr Cys Thr Cys Cys Thr Gly Ala Ala Thr Gly Ala Thr
1085 1090 1095

Thr Cys Cys Ala Thr Ala Thr Ala Cys Ala Ala Cys Ala Thr Thr
1100 1105 1110

Ala Gly Thr Gly Ala Gly Gly Gly Thr Thr Ala Cys Ala Ala Thr
1115 1120 1125

Ala Thr Ala Ala Ala Thr Ala Ala Cys Cys Thr Ala Ala Ala Gly
1130 1135 1140

Gly Thr Gly Ala Ala Thr Thr Thr Cys Cys Gly Ala Gly Gly Cys
1145 1150 1155

Cys Ala Ala Ala Ala Cys Gly Cys Cys Ala Ala Cys Cys Thr Ala
1160 1165 1170

Ala Ala Thr Cys Cys Gly Cys Gly Thr Ala Thr Cys Ala Thr Thr
1175 1180 1185

Ala Ala Ala Cys Cys Cys Ala Thr Cys Ala Cys Ala Gly Gly Ala
1190 1195 1200

Cys Gly Gly Gly Gly Gly Thr Thr Ala Gly Thr Gly Ala Ala Gly
1205 1210 1215

Ala Ala Ala Ala Thr Ala Ala Thr Cys Cys Gly Gly Thr Thr Thr
1220 1225 1230

<210> SEQ ID NO 10
<211> LENGTH: 1758
<212> TYPE: PRT
<213> ORGANISM: Artificial Sequence
<220> FEATURE:
<223> OTHER INFORMATION: Synthetic

<400> SEQUENCE: 10

Ala Thr Gly Gly Ala Cys Thr Cys Gly Gly Gly Cys Cys Gly Gly Gly
1 5 10 15

Ala Cys Thr Thr Cys Cys Thr Gly Ala Cys Cys Cys Thr Gly Cys Ala
20 25 30

Cys Gly Gly Cys Cys Thr Ala Cys Ala Gly Gly Ala Thr Gly Ala Thr
35 40 45

Gly Ala Gly Gly Ala Thr Cys Thr Ala Cys Ala Gly Gly Cys Gly Cys
50 55 60

Thr Gly Cys Thr Gly Ala Ala Gly Gly Gly Cys Ala Gly Cys Cys Ala
65 70 75 80

Gly Cys Thr Cys Cys Thr Gly Ala Ala Gly Gly Thr Gly Ala Ala Gly
85 90 95

Thr Cys Cys Ala Gly Cys Thr Cys Ala Thr Gly Gly Ala Gly Gly Ala
100 105 110

Gly Ala Gly Ala Gly Cys Gly Cys Thr Thr Cys Thr Ala Cys Ala Ala
115 120 125

Gly Thr Thr Gly Cys Ala Gly Gly Ala Gly Gly Ala Cys Thr Gly Cys
130 135 140

Ala Ala Gly Ala Cys Cys Ala Thr Cys Thr Gly Gly Cys Ala Gly Gly
145 150 155 160

Ala Gly Thr Cys Cys Cys Gly Cys Ala Ala Gly Gly Thr Cys Ala Thr
165 170 175

Gly Cys Gly Gly Ala Cys Cys Cys Cys Gly Gly Ala Gly Thr Cys Cys
180 185 190

Cys Ala Gly Cys Thr Gly Thr Thr Cys Thr Cys Cys Ala Thr Cys Gly

-continued

```
        195                 200                 205

Ala Gly Gly Ala Cys Ala Thr Thr Cys Ala Gly Gly Ala Gly Gly Thr
    210                 215                 220

Gly Cys Gly Ala Ala Thr Gly Gly Gly Gly Cys Ala Cys Cys Gly Cys
225                 230                 235                 240

Ala Cys Gly Gly Ala Gly Gly Gly Thr Cys Thr Gly Gly Ala Gly Ala
                245                 250                 255

Ala Gly Thr Thr Cys Gly Cys Cys Cys Gly Thr Gly Ala Thr Gly Thr
            260                 265                 270

Gly Cys Cys Cys Gly Ala Gly Gly Ala Cys Cys Gly Cys Thr Gly Cys
        275                 280                 285

Thr Thr Cys Thr Cys Cys Ala Thr Thr Gly Thr Cys Thr Thr Cys Ala
    290                 295                 300

Ala Gly Gly Ala Cys Cys Ala Gly Cys Gly Cys Ala Ala Thr Ala Cys
305                 310                 315                 320

Ala Cys Thr Ala Gly Ala Cys Cys Thr Cys Ala Thr Cys Gly Cys Cys
                325                 330                 335

Cys Cys Ala Thr Cys Gly Cys Cys Ala Gly Cys Thr Gly Ala Thr Gly
            340                 345                 350

Cys Cys Cys Ala Gly Cys Ala Cys Thr Gly Gly Gly Thr Gly Cys Thr
        355                 360                 365

Gly Gly Gly Gly Cys Thr Gly Cys Ala Cys Ala Ala Gly Ala Thr Cys
    370                 375                 380

Ala Thr Cys Cys Ala Cys Cys Ala Cys Thr Cys Ala Gly Gly Cys Thr
385                 390                 395                 400

Cys Cys Ala Thr Gly Gly Ala Cys Cys Ala Gly Cys Gly Thr Cys Ala
                405                 410                 415

Gly Ala Ala Gly Cys Thr Ala Cys Ala Gly Cys Ala Cys Thr Gly Gly
            420                 425                 430

Ala Thr Thr Cys Ala Cys Thr Cys Cys Thr Gly Cys Thr Thr Gly Cys
        435                 440                 445

Gly Ala Ala Ala Ala Gly Cys Thr Gly Ala Cys Ala Ala Ala Ala Ala
    450                 455                 460

Cys Ala Ala Gly Gly Ala Cys Ala Ala Cys Ala Ala Gly Ala Thr Gly
465                 470                 475                 480

Ala Gly Cys Thr Thr Cys Ala Ala Gly Gly Ala Gly Cys Thr Gly Cys
                485                 490                 495

Ala Gly Ala Ala Cys Thr Thr Cys Cys Thr Gly Ala Ala Gly Gly Gly
            500                 505                 510

Thr Gly Gly Thr Gly Gly Thr Gly Gly Thr Ala Gly Cys Ala Thr Gly
        515                 520                 525

Cys Cys Ala Ala Ala Ala Ala Thr Cys Ala Ala Cys Ala Gly Cys Thr
    530                 535                 540

Thr Thr Ala Ala Thr Thr Ala Cys Ala Ala Thr Gly Ala Cys Cys Cys
545                 550                 555                 560

Thr Gly Thr Ala Ala Ala Cys Gly Ala Thr Cys Gly Thr Ala Cys Cys
                565                 570                 575

Ala Thr Cys Cys Thr Ala Thr Ala Cys Ala Thr Ala Ala Ala Gly Cys
            580                 585                 590

Cys Gly Gly Gly Thr Gly Gly Gly Thr Ala Thr Cys Ala Cys Gly Ala
        595                 600                 605

Gly Thr Thr Cys Thr Ala Cys Ala Ala Ala Thr Cys Thr Thr Thr Cys
    610                 615                 620
```

```
Ala Ala Thr Ala Thr Thr Ala Thr Gly Ala Ala Gly Ala Ala Thr Ala
625                 630                 635                 640

Thr Ala Thr Gly Gly Ala Thr Thr Ala Thr Ala Cys Cys Thr Gly Ala
                645                 650                 655

Gly Cys Gly Thr Ala Ala Cys Gly Thr Thr Ala Thr Thr Gly Gly Thr
            660                 665                 670

Ala Cys Gly Ala Cys Ala Cys Cys Gly Cys Ala Ala Gly Ala Thr Thr
        675                 680                 685

Thr Thr Cys Ala Thr Cys Cys Ala Cys Cys Thr Ala Cys Thr Thr Cys
    690                 695                 700

Gly Thr Thr Gly Ala Ala Gly Ala Ala Cys Gly Gly Thr Gly Ala Cys
705                 710                 715                 720

Thr Cys Thr Thr Cys Cys Thr Ala Thr Thr Ala Cys Gly Ala Cys Cys
                725                 730                 735

Cys Cys Ala Ala Thr Thr Ala Thr Cys Thr Cys Cys Ala Gly Thr Cys
            740                 745                 750

Gly Gly Ala Thr Gly Ala Ala Gly Ala Gly Ala Ala Gly Gly Ala Cys
        755                 760                 765

Ala Gly Ala Thr Thr Cys Cys Thr Thr Ala Ala Ala Ala Thr Ala Gly
    770                 775                 780

Thr Ala Ala Cys Cys Ala Ala Ala Ala Thr Cys Thr Thr Thr Ala Ala
785                 790                 795                 800

Cys Ala Gly Gly Ala Thr Thr Ala Ala Thr Ala Ala Cys Ala Ala Thr
                805                 810                 815

Cys Thr Ala Gly Cys Cys Gly Gly Ala Ala Gly Thr Ala Thr Thr Thr
            820                 825                 830

Thr Gly Cys Thr Thr Gly Ala Ala Gly Ala Gly Cys Thr Thr Ala Gly
        835                 840                 845

Thr Ala Ala Ala Gly Cys Thr Ala Ala Thr Cys Cys Thr Thr Ala Cys
    850                 855                 860

Cys Thr Ala Gly Gly Thr Ala Ala Cys Gly Ala Thr Gly Ala Thr Ala
865                 870                 875                 880

Cys Ala Cys Cys Ala Gly Ala Cys Ala Ala Cys Cys Ala Gly Thr Thr
                885                 890                 895

Thr Cys Ala Thr Ala Thr Ala Gly Gly Cys Gly Ala Thr Gly Cys Ala
            900                 905                 910

Thr Cys Cys Gly Cys Cys Gly Thr Gly Gly Ala Ala Ala Thr Cys Ala
        915                 920                 925

Ala Ala Thr Thr Thr Ala Gly Cys Ala Ala Thr Gly Gly Ala Thr Cys
    930                 935                 940

Ala Cys Ala Gly Cys Ala Thr Ala Thr Thr Cys Thr Cys Thr Thr Gly
945                 950                 955                 960

Cys Cys Cys Ala Ala Cys Gly Thr Thr Ala Thr Thr Ala Thr Ala Ala
                965                 970                 975

Thr Gly Gly Gly Gly Gly Cys Gly Gly Ala Ala Cys Cys Ala Ala Ala
            980                 985                 990

Thr Thr Thr Ala Thr Thr Thr Thr  Thr Gly Ala Cys Ala  Thr Ala Thr
        995                 1000                1005

Cys Ala  Gly Ala Gly Ala Ala  Ala Thr Ala Thr Thr  Ala Gly Cys
    1010                1015                1020

Cys Thr  Gly Ala Gly Ala Ala  Ala Thr Ala Ala Cys  Thr Ala Thr
    1025                1030                1035
```

```
Ala Ala  Gly Cys Cys Gly Thr  Cys Ala Ala Ala Cys  Cys Ala Thr
    1040                 1045                 1050

Gly Gly  Gly Thr Thr Cys Gly  Gly Thr Ala Gly Cys  Ala Thr Ala
    1055                 1060                 1065

Gly Cys  Ala Ala Thr Cys Gly  Thr Thr Ala Cys Thr  Thr Thr Thr
    1070                 1075                 1080

Thr Cys  Thr Cys Cys Cys Gly  Ala Ala Thr Ala Cys  Ala Gly Thr
    1085                 1090                 1095

Thr Thr  Thr Cys Gly Cys Thr  Thr Cys Ala Ala Thr  Gly Ala Thr
    1100                 1105                 1110

Ala Ala  Thr Ala Gly Thr Ala  Thr Ala Ala Ala Thr  Gly Ala Gly
    1115                 1120                 1125

Thr Thr  Thr Ala Thr Cys Cys  Ala Ala Gly Ala Cys  Cys Cys Cys
    1130                 1135                 1140

Gly Cys  Ala Cys Thr Cys Ala  Cys Gly Cys Thr Thr  Ala Thr Gly
    1145                 1150                 1155

Cys Ala  Cys Gly Ala Ala Cys  Thr Cys Ala Thr Ala  Cys Ala Cys
    1160                 1165                 1170

Thr Cys  Thr Thr Thr Ala Cys  Ala Cys Gly Gly Cys  Cys Thr Gly
    1175                 1180                 1185

Thr Ala  Thr Gly Gly Cys Gly  Cys Thr Ala Ala Gly  Gly Gly Gly
    1190                 1195                 1200

Ala Thr  Ala Ala Cys Cys Ala  Cys Thr Ala Cys Gly  Thr Gly Thr
    1205                 1210                 1215

Ala Cys  Cys Ala Thr Thr Ala  Cys Thr Cys Ala Gly  Cys Ala Ala
    1220                 1225                 1230

Cys Ala  Gly Ala Ala Cys Cys  Cys Ala Thr Thr Gly  Ala Thr Ala
    1235                 1240                 1245

Ala Cys  Gly Ala Ala Cys Ala  Gly Gly Ala Ala Gly  Gly Gly Cys
    1250                 1255                 1260

Ala Thr  Thr Ala Ala Ala Ala  Thr Cys Gly Ala Gly  Gly Ala Ala
    1265                 1270                 1275

Thr Thr  Thr Cys Thr Thr Ala  Cys Ala Thr Thr Thr  Gly Gly Ala
    1280                 1285                 1290

Gly Gly  Cys Ala Ala Cys Gly  Ala Thr Cys Thr Gly  Ala Ala Cys
    1295                 1300                 1305

Ala Thr  Thr Ala Thr Ala Ala  Cys Thr Gly Thr Cys  Gly Cys Ala
    1310                 1315                 1320

Cys Ala  Gly Thr Ala Cys Ala  Ala Thr Gly Ala Cys  Ala Thr Cys
    1325                 1330                 1335

Thr Ala  Thr Ala Cys Cys Ala  Ala Cys Thr Thr Ala  Cys Thr Ala
    1340                 1345                 1350

Ala Ala  Thr Gly Ala Thr Thr  Ala Thr Ala Gly Ala  Ala Ala Ala
    1355                 1360                 1365

Ala Thr  Cys Gly Cys Thr Thr  Cys Thr Ala Ala Gly  Thr Thr Ala
    1370                 1375                 1380

Thr Cys  Cys Ala Ala Gly Gly  Thr Thr Cys Ala Ala  Gly Thr Cys
    1385                 1390                 1395

Thr Cys  Ala Ala Ala Cys Cys  Cys Thr Cys Ala Ala  Cys Thr Gly
    1400                 1405                 1410

Ala Ala  Thr Cys Cys Gly Thr  Ala Thr Ala Ala Gly  Gly Ala Cys
    1415                 1420                 1425

Ala Thr  Ala Thr Thr Cys Cys  Ala Ala Gly Ala Ala  Ala Ala Ala
```

```
    1430                1435                1440

Thr Ala  Thr Gly Gly Ala Thr  Thr Ala Gly Ala Cys  Ala Ala Ala
    1445                1450                1455

Gly Ala  Cys Gly Cys Gly Thr  Cys Ala Gly Gly Ala  Ala Thr Cys
    1460                1465                1470

Thr Ala  Thr Thr Cys Gly Gly  Thr Ala Ala Ala Cys  Ala Thr Thr
    1475                1480                1485

Ala Ala  Cys Ala Ala Ala Thr  Thr Cys Gly Ala Cys  Gly Ala Thr
    1490                1495                1500

Ala Thr  Thr Thr Thr Gly Ala  Ala Gly Ala Ala Ala  Cys Thr Thr
    1505                1510                1515

Thr Ala  Cys Ala Gly Cys Thr  Thr Cys Ala Cys Gly  Gly Ala Gly
    1520                1525                1530

Thr Thr  Cys Gly Ala Cys Thr  Thr Gly Gly Cys Cys  Ala Cys Cys
    1535                1540                1545

Ala Ala  Ala Thr Thr Cys Cys  Ala Gly Gly Thr Cys  Ala Ala Ala
    1550                1555                1560

Thr Gly  Cys Cys Gly Ala Gly  Ala Gly Ala Cys Ala  Thr Ala Cys
    1565                1570                1575

Ala Thr  Cys Gly Gly Ala Cys  Gly Gly Cys Cys Thr  Ala Ala Gly
    1580                1585                1590

Thr Thr  Thr Thr Thr Thr Ala  Ala Gly Cys Thr Gly  Thr Cys Gly
    1595                1600                1605

Ala Ala  Thr Cys Thr Cys Cys  Thr Gly Ala Ala Thr  Gly Ala Thr
    1610                1615                1620

Thr Cys  Cys Ala Thr Ala Thr  Ala Cys Ala Ala Cys  Ala Thr Thr
    1625                1630                1635

Ala Gly  Thr Gly Ala Gly Gly  Gly Thr Thr Ala Cys  Ala Ala Thr
    1640                1645                1650

Ala Thr  Ala Ala Ala Thr Ala  Ala Cys Cys Thr Ala  Ala Ala Gly
    1655                1660                1665

Gly Thr  Gly Ala Ala Thr Thr  Thr Cys Cys Gly Ala  Gly Gly Cys
    1670                1675                1680

Cys Ala  Ala Ala Ala Cys Gly  Cys Cys Ala Ala Cys  Cys Thr Ala
    1685                1690                1695

Ala Ala  Thr Cys Cys Gly Cys  Gly Thr Ala Thr Cys  Ala Thr Thr
    1700                1705                1710

Ala Ala  Ala Cys Cys Cys Ala  Thr Cys Ala Cys Ala  Gly Gly Ala
    1715                1720                1725

Cys Gly  Gly Gly Gly Gly Thr  Thr Ala Gly Thr Gly  Ala Ala Gly
    1730                1735                1740

Ala Ala  Ala Ala Thr Ala Ala  Thr Cys Cys Gly Gly  Thr Thr Thr
    1745                1750                1755
```

<210> SEQ ID NO 11
<211> LENGTH: 1758
<212> TYPE: PRT
<213> ORGANISM: Artificial Sequence
<220> FEATURE:
<223> OTHER INFORMATION: Synthetic

<400> SEQUENCE: 11

```
Ala Thr Gly Gly Ala Cys Thr Cys Gly Gly Gly Cys Cys Gly Gly Gly
1               5                   10                  15

Ala Cys Thr Thr Cys Cys Thr Gly Ala Cys Cys Cys Thr Gly Cys Ala
```

```
            20                  25                  30

Cys Gly Gly Cys Cys Thr Ala Cys Ala Gly Gly Ala Thr Gly Ala Thr
        35                  40                  45

Gly Ala Gly Gly Ala Thr Cys Thr Ala Cys Ala Gly Gly Cys Gly Cys
    50                  55                  60

Thr Gly Cys Thr Gly Ala Ala Gly Gly Gly Cys Ala Gly Cys Cys Ala
65                  70                  75                  80

Gly Cys Thr Cys Cys Thr Gly Ala Ala Gly Gly Thr Gly Ala Ala Gly
                85                  90                  95

Thr Cys Cys Ala Gly Cys Thr Cys Ala Thr Gly Gly Ala Gly Gly Ala
            100                 105                 110

Gly Ala Gly Ala Gly Cys Gly Cys Thr Thr Cys Thr Ala Cys Ala Ala
        115                 120                 125

Gly Thr Thr Gly Cys Ala Gly Gly Ala Gly Gly Ala Cys Thr Gly Cys
    130                 135                 140

Ala Ala Gly Ala Cys Cys Ala Thr Cys Thr Gly Gly Cys Ala Gly Gly
145                 150                 155                 160

Ala Gly Thr Cys Cys Cys Gly Cys Ala Ala Gly Gly Thr Cys Ala Thr
                165                 170                 175

Gly Cys Gly Gly Ala Cys Cys Cys Cys Gly Gly Ala Gly Thr Cys Cys
            180                 185                 190

Cys Ala Gly Cys Thr Gly Thr Thr Cys Thr Cys Cys Ala Thr Cys Gly
        195                 200                 205

Ala Gly Gly Ala Cys Ala Thr Thr Cys Ala Gly Gly Ala Gly Gly Thr
    210                 215                 220

Gly Cys Gly Ala Ala Thr Gly Gly Gly Gly Cys Ala Cys Cys Gly Cys
225                 230                 235                 240

Ala Cys Gly Gly Ala Gly Gly Gly Thr Cys Thr Gly Gly Ala Gly Ala
                245                 250                 255

Ala Gly Thr Thr Cys Gly Cys Cys Cys Gly Thr Gly Ala Thr Gly Thr
            260                 265                 270

Gly Cys Cys Cys Gly Ala Gly Gly Ala Cys Cys Gly Cys Thr Gly Cys
        275                 280                 285

Thr Thr Cys Thr Cys Cys Ala Thr Thr Gly Thr Cys Thr Thr Cys Ala
    290                 295                 300

Ala Gly Gly Ala Cys Cys Ala Gly Cys Gly Cys Ala Ala Thr Ala Cys
305                 310                 315                 320

Ala Cys Thr Ala Gly Ala Cys Cys Thr Cys Ala Thr Cys Gly Cys Cys
                325                 330                 335

Cys Cys Ala Thr Cys Gly Cys Cys Ala Gly Cys Thr Gly Ala Thr Gly
            340                 345                 350

Cys Cys Cys Ala Gly Cys Ala Cys Thr Gly Gly Gly Thr Gly Cys Thr
        355                 360                 365

Gly Gly Gly Gly Cys Thr Gly Cys Ala Cys Ala Ala Gly Ala Thr Cys
    370                 375                 380

Ala Thr Cys Cys Ala Cys Cys Ala Cys Thr Cys Ala Gly Gly Cys Thr
385                 390                 395                 400

Cys Cys Ala Thr Gly Gly Ala Cys Cys Ala Gly Cys Gly Thr Cys Ala
                405                 410                 415

Gly Ala Ala Gly Cys Thr Ala Cys Ala Gly Cys Ala Cys Thr Gly Gly
            420                 425                 430

Ala Thr Thr Cys Ala Cys Thr Cys Cys Thr Gly Cys Thr Thr Gly Cys
        435                 440                 445
```

```
Gly Ala Ala Ala Ala Gly Cys Thr Gly Ala Cys Ala Ala Ala Ala Ala
    450                 455                 460

Cys Ala Ala Gly Gly Ala Cys Ala Ala Cys Ala Ala Gly Ala Thr Gly
465                 470                 475                 480

Ala Gly Cys Thr Thr Cys Ala Ala Gly Gly Ala Gly Cys Thr Gly Cys
                485                 490                 495

Ala Gly Ala Ala Cys Thr Thr Cys Cys Thr Gly Ala Ala Gly Gly Gly
            500                 505                 510

Thr Gly Gly Thr Gly Gly Thr Gly Gly Thr Ala Gly Cys Ala Thr Gly
        515                 520                 525

Cys Cys Ala Ala Ala Ala Ala Thr Cys Ala Ala Cys Ala Gly Cys Thr
    530                 535                 540

Thr Thr Ala Ala Thr Thr Ala Cys Ala Ala Thr Gly Ala Cys Cys Cys
545                 550                 555                 560

Thr Gly Thr Ala Ala Ala Cys Gly Ala Thr Cys Gly Thr Ala Cys Cys
                565                 570                 575

Ala Thr Cys Cys Thr Ala Thr Ala Cys Ala Thr Ala Ala Ala Gly Cys
            580                 585                 590

Cys Gly Gly Gly Thr Gly Gly Gly Thr Ala Thr Cys Ala Cys Gly Ala
        595                 600                 605

Gly Thr Thr Cys Thr Ala Cys Ala Ala Ala Thr Cys Thr Thr Thr Cys
    610                 615                 620

Ala Ala Thr Ala Thr Thr Ala Thr Gly Ala Ala Gly Ala Ala Thr Ala
625                 630                 635                 640

Thr Ala Thr Gly Gly Ala Thr Thr Ala Thr Ala Cys Cys Thr Gly Ala
                645                 650                 655

Gly Cys Gly Thr Ala Ala Cys Gly Thr Thr Ala Thr Thr Gly Gly Thr
            660                 665                 670

Ala Cys Gly Ala Cys Ala Cys Cys Gly Cys Ala Ala Gly Ala Thr Thr
        675                 680                 685

Thr Thr Cys Ala Thr Cys Cys Ala Cys Cys Thr Ala Cys Thr Thr Cys
    690                 695                 700

Gly Thr Thr Gly Ala Ala Gly Ala Ala Cys Gly Gly Thr Gly Ala Cys
705                 710                 715                 720

Thr Cys Thr Thr Cys Cys Thr Ala Thr Thr Ala Cys Gly Ala Cys Cys
                725                 730                 735

Cys Cys Ala Ala Thr Thr Ala Thr Cys Thr Cys Cys Ala Gly Thr Cys
            740                 745                 750

Gly Gly Ala Thr Gly Ala Ala Gly Ala Gly Ala Ala Gly Gly Ala Cys
        755                 760                 765

Ala Gly Ala Thr Thr Cys Cys Thr Thr Ala Ala Ala Ala Thr Ala Gly
    770                 775                 780

Thr Ala Ala Cys Cys Ala Ala Ala Ala Thr Cys Thr Thr Thr Ala Ala
785                 790                 795                 800

Cys Ala Gly Gly Ala Thr Thr Ala Ala Thr Ala Ala Cys Ala Ala Thr
                805                 810                 815

Cys Thr Ala Gly Cys Cys Gly Gly Ala Ala Gly Thr Ala Thr Thr Thr
            820                 825                 830

Thr Gly Cys Thr Thr Gly Ala Ala Gly Ala Gly Cys Thr Thr Ala Gly
        835                 840                 845

Thr Ala Ala Ala Gly Cys Thr Ala Ala Thr Cys Cys Thr Thr Ala Cys
    850                 855                 860
```

```
Cys Thr Ala Gly Gly Thr Ala Ala Cys Gly Ala Thr Gly Ala Thr Ala
865                 870                 875                 880

Cys Ala Cys Cys Ala Gly Ala Cys Ala Ala Cys Cys Ala Gly Thr Thr
                885                 890                 895

Thr Cys Ala Thr Ala Thr Ala Gly Gly Cys Gly Ala Thr Gly Cys Ala
            900                 905                 910

Thr Cys Cys Gly Cys Cys Gly Thr Gly Gly Ala Ala Ala Thr Cys Ala
        915                 920                 925

Ala Ala Thr Thr Thr Ala Gly Cys Ala Ala Thr Gly Gly Ala Thr Cys
    930                 935                 940

Ala Cys Ala Gly Cys Ala Thr Ala Thr Thr Cys Thr Cys Thr Thr Gly
945                 950                 955                 960

Cys Cys Cys Ala Ala Cys Gly Thr Thr Ala Thr Thr Ala Thr Ala Ala
                965                 970                 975

Thr Gly Gly Gly Gly Gly Cys Gly Gly Ala Ala Cys Cys Ala Ala Ala
            980                 985                 990

Thr Thr Thr Ala Thr Thr Thr Thr  Thr Gly Ala Cys Ala  Thr Ala Thr
        995                 1000                1005

Cys Ala  Gly Ala Gly Ala Ala  Ala Thr Ala Thr Thr  Ala Gly Cys
    1010                1015                1020

Gly Cys  Cys Ala Gly Ala Ala  Ala Thr Ala Ala Cys  Thr Ala Thr
    1025                1030                1035

Ala Ala  Gly Cys Cys Gly Thr  Cys Ala Ala Ala Cys  Cys Ala Thr
    1040                1045                1050

Gly Gly  Gly Thr Thr Cys Gly  Gly Thr Ala Gly Cys  Ala Thr Ala
    1055                1060                1065

Gly Cys  Ala Ala Thr Cys Gly  Thr Thr Ala Cys Thr  Thr Thr Thr
    1070                1075                1080

Thr Cys  Thr Cys Cys Cys Gly  Ala Ala Thr Ala Cys  Ala Gly Thr
    1085                1090                1095

Thr Thr  Thr Cys Gly Cys Thr  Thr Cys Ala Ala Thr  Gly Ala Thr
    1100                1105                1110

Ala Ala  Thr Ala Gly Thr Ala  Thr Ala Ala Ala Thr  Gly Ala Gly
    1115                1120                1125

Thr Thr  Thr Ala Thr Cys Cys  Ala Ala Gly Ala Cys  Cys Cys Cys
    1130                1135                1140

Gly Cys  Ala Cys Thr Cys Ala  Cys Gly Cys Thr Thr  Ala Thr Gly
    1145                1150                1155

Cys Ala  Cys Gly Ala Ala Cys  Thr Cys Ala Thr Ala  Cys Ala Cys
    1160                1165                1170

Thr Cys  Thr Thr Thr Ala Cys  Ala Cys Gly Gly Cys  Cys Thr Gly
    1175                1180                1185

Thr Ala  Thr Gly Gly Cys Gly  Cys Thr Ala Ala Gly  Gly Gly Gly
    1190                1195                1200

Ala Thr  Ala Ala Cys Cys Ala  Cys Thr Ala Cys Gly  Thr Gly Thr
    1205                1210                1215

Ala Cys  Cys Ala Thr Thr Ala  Cys Thr Cys Ala Gly  Cys Ala Ala
    1220                1225                1230

Cys Ala  Gly Ala Ala Cys Cys  Cys Ala Thr Thr Gly  Ala Thr Ala
    1235                1240                1245

Ala Cys  Gly Ala Ala Cys Ala  Gly Gly Ala Ala Gly  Gly Gly Cys
    1250                1255                1260

Ala Thr  Thr Ala Ala Ala Ala  Thr Cys Gly Ala Gly  Gly Ala Ala
```

```
    1265                1270                1275

Thr Thr  Thr Cys Thr Thr Ala  Cys Ala Thr Thr Thr  Gly Gly Ala
    1280                1285                1290

Gly Gly  Cys Ala Ala Cys Gly  Ala Thr Cys Thr Gly  Ala Ala Cys
    1295                1300                1305

Ala Thr  Thr Ala Thr Ala Ala  Cys Thr Gly Thr Cys  Gly Cys Ala
    1310                1315                1320

Cys Ala  Gly Thr Ala Cys Ala  Ala Thr Gly Ala Cys  Ala Thr Cys
    1325                1330                1335

Thr Ala  Thr Ala Cys Cys Ala  Ala Cys Thr Thr Ala  Cys Thr Ala
    1340                1345                1350

Ala Ala  Thr Gly Ala Thr Thr  Ala Thr Ala Gly Ala  Ala Ala Ala
    1355                1360                1365

Ala Thr  Cys Gly Cys Thr Thr  Cys Thr Ala Ala Gly  Thr Thr Ala
    1370                1375                1380

Thr Cys  Cys Ala Ala Gly Gly  Thr Thr Cys Ala Ala  Gly Thr Cys
    1385                1390                1395

Thr Cys  Ala Ala Ala Cys Cys  Cys Thr Cys Ala Ala  Cys Thr Gly
    1400                1405                1410

Ala Ala  Thr Cys Cys Gly Thr  Ala Thr Ala Ala Gly  Gly Ala Cys
    1415                1420                1425

Ala Thr  Ala Thr Thr Cys Cys  Ala Ala Gly Ala Ala  Ala Ala Ala
    1430                1435                1440

Thr Ala  Thr Gly Gly Ala Thr  Thr Ala Gly Ala Cys  Ala Ala Ala
    1445                1450                1455

Gly Ala  Cys Gly Cys Gly Thr  Cys Ala Gly Gly Ala  Ala Thr Cys
    1460                1465                1470

Thr Ala  Thr Thr Cys Gly Gly  Thr Ala Ala Ala Cys  Ala Thr Thr
    1475                1480                1485

Ala Ala  Cys Ala Ala Ala Thr  Thr Cys Gly Ala Cys  Gly Ala Thr
    1490                1495                1500

Ala Thr  Thr Thr Thr Gly Ala  Ala Gly Ala Ala Ala  Cys Thr Thr
    1505                1510                1515

Thr Ala  Cys Ala Gly Cys Thr  Thr Cys Ala Cys Gly  Gly Ala Gly
    1520                1525                1530

Thr Thr  Cys Gly Ala Cys Thr  Thr Gly Gly Cys Cys  Ala Cys Cys
    1535                1540                1545

Ala Ala  Ala Thr Thr Cys Cys  Ala Gly Gly Thr Cys  Ala Ala Ala
    1550                1555                1560

Thr Gly  Cys Cys Gly Ala Gly  Ala Gly Ala Cys Ala  Thr Ala Cys
    1565                1570                1575

Ala Thr  Cys Gly Gly Ala Cys  Gly Gly Cys Cys Thr  Ala Ala Gly
    1580                1585                1590

Thr Thr  Thr Thr Thr Thr Ala  Ala Gly Cys Thr Gly  Thr Cys Gly
    1595                1600                1605

Ala Ala  Thr Cys Thr Cys Cys  Thr Gly Ala Ala Thr  Gly Ala Thr
    1610                1615                1620

Thr Cys  Cys Ala Thr Ala Thr  Ala Cys Ala Ala Cys  Ala Thr Thr
    1625                1630                1635

Ala Gly  Thr Gly Ala Gly Gly  Gly Thr Thr Ala Cys  Ala Ala Thr
    1640                1645                1650

Ala Thr  Ala Ala Ala Thr Ala  Ala Cys Cys Thr Ala  Ala Ala Gly
    1655                1660                1665
```

```
Gly Thr  Gly Ala Ala Thr Thr  Thr Cys Cys Gly Ala  Gly Gly Cys
    1670                1675                1680

Cys Ala  Ala Ala Ala Cys Gly  Cys Cys Ala Ala Cys  Cys Thr Ala
    1685                1690                1695

Ala Ala  Thr Cys Cys Gly Cys  Gly Thr Ala Thr Cys  Ala Thr Thr
    1700                1705                1710

Ala Ala  Ala Cys Cys Cys Ala  Thr Cys Ala Cys Ala  Gly Gly Ala
    1715                1720                1725

Cys Gly  Gly Gly Gly Gly Thr  Thr Ala Gly Thr Gly  Ala Ala Gly
    1730                1735                1740

Ala Ala  Ala Ala Thr Ala Ala  Thr Cys Cys Gly Gly  Thr Thr Thr
    1745                1750                1755
```

<210> SEQ ID NO 12
<211> LENGTH: 403
<212> TYPE: PRT
<213> ORGANISM: Homo sapiens

<400> SEQUENCE: 12

```
Met Thr Ala Ile Ile Lys Glu Ile Val Ser Arg Asn Lys Arg Arg Tyr
1               5                   10                  15

Gln Glu Asp Gly Phe Asp Leu Asp Leu Thr Tyr Ile Tyr Pro Asn Ile
            20                  25                  30

Ile Ala Met Gly Phe Pro Ala Glu Arg Leu Glu Gly Val Tyr Arg Asn
        35                  40                  45

Asn Ile Asp Asp Val Val Arg Phe Leu Asp Ser Lys His Lys Asn His
    50                  55                  60

Tyr Lys Ile Tyr Asn Leu Cys Ala Glu Arg His Tyr Asp Thr Ala Lys
65                  70                  75                  80

Phe Asn Cys Arg Val Ala Gln Tyr Pro Phe Glu Asp His Asn Pro Pro
                85                  90                  95

Gln Leu Glu Leu Ile Lys Pro Phe Cys Glu Asp Leu Asp Gln Trp Leu
            100                 105                 110

Ser Glu Asp Asp Asn His Val Ala Ala Ile His Cys Lys Ala Gly Lys
        115                 120                 125

Gly Arg Thr Gly Val Met Ile Cys Ala Tyr Leu Leu His Arg Gly Lys
    130                 135                 140

Phe Leu Lys Ala Gln Glu Ala Leu Asp Phe Tyr Gly Glu Val Arg Thr
145                 150                 155                 160

Arg Asp Lys Lys Gly Val Thr Ile Pro Ser Gln Arg Arg Tyr Val Tyr
                165                 170                 175

Tyr Tyr Ser Tyr Leu Leu Lys Asn His Leu Asp Tyr Arg Pro Val Ala
            180                 185                 190

Leu Leu Phe His Lys Met Met Phe Glu Thr Ile Pro Met Phe Ser Gly
        195                 200                 205

Gly Thr Cys Asn Pro Gln Phe Val Val Cys Gln Leu Lys Val Lys Ile
    210                 215                 220

Tyr Ser Ser Asn Ser Gly Pro Thr Arg Arg Glu Asp Lys Phe Met Tyr
225                 230                 235                 240

Phe Glu Phe Pro Gln Pro Leu Pro Val Cys Gly Asp Ile Lys Val Glu
                245                 250                 255

Phe Phe His Lys Gln Asn Lys Met Leu Lys Lys Asp Lys Met Phe His
            260                 265                 270

Phe Trp Val Asn Thr Phe Phe Ile Pro Gly Pro Glu Glu Thr Ser Glu
```

```
        275                 280                 285

Lys Val Glu Asn Gly Ser Leu Cys Asp Gln Glu Ile Asp Ser Ile Cys
    290                 295                 300

Ser Ile Glu Arg Ala Asp Asn Asp Lys Glu Tyr Leu Val Leu Thr Leu
305                 310                 315                 320

Thr Lys Asn Asp Leu Asp Lys Ala Asn Lys Asp Lys Ala Asn Arg Tyr
                325                 330                 335

Phe Ser Pro Asn Phe Lys Val Lys Leu Tyr Phe Thr Lys Thr Val Glu
            340                 345                 350

Glu Pro Ser Asn Pro Glu Ala Ser Ser Ser Thr Ser Val Thr Pro Asp
        355                 360                 365

Val Ser Asp Asn Glu Pro Asp His Tyr Arg Tyr Ser Asp Thr Thr Asp
    370                 375                 380

Ser Asp Pro Glu Asn Glu Pro Phe Asp Glu Asp Gln His Thr Gln Ile
385                 390                 395                 400

Thr Lys Val


<210> SEQ ID NO 13
<211> LENGTH: 20
<212> TYPE: PRT
<213> ORGANISM: Artificial Sequence
<220> FEATURE:
<223> OTHER INFORMATION: Synthetic

<400> SEQUENCE: 13

Asn Gly Ser Leu Cys Asp Gln Glu Ile Asp Ser Ile Cys Ser Ile Met
1               5                   10                  15

Glu Lys Ala Asp
            20


<210> SEQ ID NO 14
<211> LENGTH: 438
<212> TYPE: PRT
<213> ORGANISM: Artificial Sequence
<220> FEATURE:
<223> OTHER INFORMATION: Synthetic

<400> SEQUENCE: 14

Cys Lys Asn Ile Val Ser Val Lys Gly Ile Arg Lys Ser Ile Cys Ile
1               5                   10                  15

Glu Ile Asn Asn Gly Glu Leu Phe Phe Val Ala Ser Glu Asn Ser Tyr
            20                  25                  30

Asn Asp Asp Asn Ile Asn Thr Pro Lys Glu Ile Asp Asp Thr Val Thr
        35                  40                  45

Ser Asn Asn Asn Tyr Glu Asn Asp Leu Asp Gln Val Ile Leu Asn Phe
    50                  55                  60

Asn Ser Glu Ser Ala Pro Gly Leu Ser Asp Glu Lys Leu Asn Leu Thr
65                  70                  75                  80

Ile Gln Asn Asp Ala Tyr Ile Pro Lys Tyr Asp Ser Asn Gly Thr Ser
                85                  90                  95

Asp Ile Glu Gln His Asp Val Asn Glu Leu Asn Val Phe Phe Tyr Leu
            100                 105                 110

Asp Ala Gln Lys Val Pro Glu Gly Glu Asn Asn Val Asn Leu Thr Ser
        115                 120                 125

Ser Ile Asp Thr Ala Leu Leu Glu Gln Pro Lys Ile Tyr Thr Phe Phe
    130                 135                 140

Ser Ser Glu Phe Ile Asn Asn Val Asn Lys Pro Val Gln Ala Ala Leu
```

```
145                 150                 155                 160

Phe Val Ser Trp Ile Gln Gln Val Leu Val Asp Phe Thr Thr Glu Ala
                165                 170                 175

Asn Gln Lys Ser Thr Val Asp Lys Ile Ala Asp Ile Ser Ile Val Val
            180                 185                 190

Pro Tyr Ile Gly Leu Ala Leu Asn Ile Gly Asn Glu Ala Gln Lys Gly
        195                 200                 205

Asn Phe Lys Asp Ala Leu Glu Leu Leu Gly Ala Gly Ile Leu Leu Glu
    210                 215                 220

Phe Glu Pro Glu Leu Leu Ile Pro Thr Ile Leu Val Phe Thr Ile Lys
225                 230                 235                 240

Ser Phe Leu Gly Ser Ser Asp Asn Lys Asn Lys Val Ile Lys Ala Ile
                245                 250                 255

Asn Asn Ala Leu Lys Glu Arg Asp Glu Lys Trp Lys Glu Val Tyr Ser
            260                 265                 270

Phe Ile Val Ser Asn Trp Met Thr Lys Ile Asn Thr Gln Phe Asn Lys
        275                 280                 285

Arg Lys Glu Gln Met Tyr Gln Ala Leu Gln Asn Gln Val Asn Ala Ile
    290                 295                 300

Lys Thr Ile Ile Glu Ser Lys Tyr Asn Ser Tyr Thr Leu Glu Glu Lys
305                 310                 315                 320

Asn Glu Leu Thr Asn Lys Tyr Asp Ile Lys Gln Ile Glu Asn Glu Leu
                325                 330                 335

Asn Gln Lys Val Ser Ile Ala Met Asn Asn Ile Asp Arg Phe Leu Thr
            340                 345                 350

Glu Ser Ser Ile Ser Tyr Leu Met Lys Leu Ile Asn Glu Val Lys Ile
        355                 360                 365

Asn Lys Leu Arg Glu Tyr Asp Glu Asn Val Lys Thr Tyr Leu Leu Asn
    370                 375                 380

Tyr Ile Ile Gln His Gly Ser Ile Leu Gly Glu Ser Gln Gln Glu Leu
385                 390                 395                 400

Asn Ser Met Val Thr Asp Thr Leu Asn Asn Ser Ile Pro Phe Lys Leu
                405                 410                 415

Ser Ser Tyr Thr Asp Asp Lys Ile Leu Ile Ser Tyr Phe Asn Lys Phe
            420                 425                 430

Phe Lys Arg Ile Lys Ser
        435


<210> SEQ ID NO 15
<211> LENGTH: 403
<212> TYPE: PRT
<213> ORGANISM: Artificial Sequence
<220> FEATURE:
<223> OTHER INFORMATION: Synthetic

<400> SEQUENCE: 15

Ser Ser Val Leu Asn Met Arg Tyr Lys Asn Asp Lys Tyr Val Asp Thr
1               5                   10                  15

Ser Gly Tyr Asp Ser Asn Ile Asn Ile Asn Gly Asp Val Tyr Lys Tyr
            20                  25                  30

Pro Thr Asn Lys Asn Gln Phe Glu Ile Tyr Asn Asp Lys Leu Ser Glu
        35                  40                  45

Val Asn Ile Ser Gln Asn Asp Tyr Ile Ile Tyr Asp Asn Lys Tyr Lys
    50                  55                  60

Asn Phe Ser Ile Ser Phe Trp Val Arg Ile Pro Asn Tyr Asp Asn Lys
```

```
65                  70                  75                  80

Ile Val Asn Val Asn Asn Glu Tyr Thr Ile Ile Asn Cys Met Arg Asp
                85                  90                  95

Asn Asn Ser Gly Trp Lys Val Ser Leu Asn His Asn Glu Ile Ile Trp
            100                 105                 110

Thr Leu Gln Asp Asn Ala Gly Ile Asn Gln Lys Leu Ala Phe Asn Tyr
        115                 120                 125

Gly Asn Ala Asn Gly Ile Ser Asp Tyr Ile Asn Lys Trp Ile Phe Val
    130                 135                 140

Thr Ile Thr Asn Asp Arg Leu Gly Asp Ser Lys Leu Tyr Ile Asn Gly
145                 150                 155                 160

Asn Leu Ile Asp Gln Lys Ser Ile Leu Asn Leu Gly Asn Ile His Val
                165                 170                 175

Ser Asp Asn Ile Leu Phe Lys Ile Val Asn Cys Ser Tyr Thr Arg Tyr
            180                 185                 190

Ile Gly Ile Arg Tyr Phe Asn Ile Phe Asp Lys Glu Leu Asp Glu Thr
        195                 200                 205

Glu Ile Gln Thr Leu Tyr Ser Asn Glu Pro Asn Thr Asn Ile Leu Lys
    210                 215                 220

Asp Phe Trp Gly Asn Tyr Leu Leu Tyr Asp Lys Glu Tyr Tyr Leu Leu
225                 230                 235                 240

Asn Val Leu Lys Pro Asn Asn Phe Ile Asp Arg Arg Lys Asp Ser Thr
                245                 250                 255

Leu Ser Ile Asn Asn Ile Arg Ser Thr Ile Leu Leu Ala Asn Arg Leu
            260                 265                 270

Tyr Ser Gly Ile Lys Val Lys Ile Gln Arg Val Asn Asn Ser Ser Thr
        275                 280                 285

Asn Asp Asn Leu Val Arg Lys Asn Asp Gln Val Tyr Ile Asn Phe Val
    290                 295                 300

Ala Ser Lys Thr His Leu Phe Pro Leu Tyr Ala Asp Thr Ala Thr Thr
305                 310                 315                 320

Asn Lys Glu Lys Thr Ile Lys Ile Ser Ser Ser Gly Asn Arg Phe Asn
                325                 330                 335

Gln Val Val Val Met Asn Ser Val Gly Asn Asn Cys Thr Met Asn Phe
            340                 345                 350

Lys Asn Asn Asn Gly Asn Asn Ile Gly Leu Leu Gly Phe Lys Ala Asp
        355                 360                 365

Thr Val Val Ala Ser Thr Trp Tyr Tyr Thr His Met Arg Asp His Thr
    370                 375                 380

Asn Ser Asn Gly Cys Phe Trp Asn Phe Ile Ser Glu Glu His Gly Trp
385                 390                 395                 400

Gln Glu Lys


<210> SEQ ID NO 16
<211> LENGTH: 206
<212> TYPE: PRT
<213> ORGANISM: Artificial Sequence
<220> FEATURE:
<223> OTHER INFORMATION: Synthetic

<400> SEQUENCE: 16

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30
```

Leu Gln Leu Val Glu Glu Ser Lys Asp Ala Gly Ile Arg Thr Leu Val
35 40 45

Met Leu Asp Glu Gln Gly Glu Gln Leu Glu Arg Ile Glu Glu Gly Met
50 55 60

Asp Gln Ile Asn Lys Asp Met Lys Glu Ala Glu Lys Asn Leu Thr Asp
65 70 75 80

Leu Gly Lys Phe Cys Gly Leu Cys Val Cys Pro Cys Asn Lys Leu Lys
85 90 95

Ser Ser Asp Ala Tyr Lys Lys Ala Trp Gly Asn Asn Gln Asp Gly Val
100 105 110

Val Ala Ser Gln Pro Ala Arg Val Val Asp Glu Arg Glu Gln Met Ala
115 120 125

Ile Ser Gly Gly Phe Ile Arg Arg Val Thr Asn Asp Ala Arg Glu Asn
130 135 140

Glu Met Asp Glu Asn Leu Glu Gln Val Ser Gly Ile Ile Gly Asn Leu
145 150 155 160

Arg His Met Ala Leu Asp Met Gly Asn Glu Ile Asp Thr Gln Asn Arg
165 170 175

Gln Ile Asp Arg Ile Met Glu Lys Ala Asp Ser Asn Lys Thr Arg Ile
180 185 190

Asp Glu Ala Asn Gln Arg Ala Thr Lys Met Leu Gly Ser Gly
195 200 205

<210> SEQ ID NO 17
<211> LENGTH: 10
<212> TYPE: PRT
<213> ORGANISM: Artificial Sequence
<220> FEATURE:
<223> OTHER INFORMATION: Synthetic

<400> SEQUENCE: 17

Arg Gln Ile Asp Arg Ile Met Glu Lys Ala
1 5 10

<210> SEQ ID NO 18
<211> LENGTH: 118
<212> TYPE: PRT
<213> ORGANISM: Homo sapiens

<400> SEQUENCE: 18

Asn Pro Asp Arg Glu Gly Trp Leu Leu Lys Leu Gly Gly Gly Arg Val
1 5 10 15

Lys Thr Trp Lys Arg Arg Trp Phe Ile Leu Thr Asp Asn Cys Leu Tyr
20 25 30

Tyr Phe Glu Tyr Thr Thr Asp Lys Glu Pro Arg Gly Ile Ile Pro Leu
35 40 45

Glu Asn Leu Ser Ile Arg Glu Val Glu Asp Ser Lys Lys Pro Asn Cys
50 55 60

Phe Glu Leu Tyr Ile Pro Asp Asn Lys Asp Gln Val Ile Lys Ala Cys
65 70 75 80

Lys Thr Glu Ala Asp Gly Arg Val Val Glu Gly Asn His Thr Val Tyr
85 90 95

Arg Ile Ser Ala Pro Thr Pro Glu Glu Lys Glu Glu Trp Ile Lys Cys
100 105 110

Ile Lys Ala Ala Ile Ser
115

<210> SEQ ID NO 19
<211> LENGTH: 118
<212> TYPE: PRT
<213> ORGANISM: Homo sapiens

<400> SEQUENCE: 19

```
Asn Pro Asp Arg Glu Gly Trp Leu Leu Lys Leu Gly Gly Gly Arg Val
1               5                   10                  15

Lys Thr Trp Lys Arg Arg Trp Phe Ile Leu Thr Asp Asn Cys Leu Tyr
            20                  25                  30

Tyr Phe Glu Tyr Thr Thr Asp Lys Glu Pro Arg Gly Ile Ile Pro Leu
        35                  40                  45

Glu Asn Leu Ser Ile Arg Glu Val Asp Asp Pro Arg Lys Pro Asn Cys
    50                  55                  60

Phe Glu Leu Tyr Ile Pro Asn Asn Lys Gly Gln Leu Ile Lys Ala Cys
65                  70                  75                  80

Lys Thr Glu Ala Asp Gly Arg Val Val Glu Gly Asn His Met Val Tyr
                85                  90                  95

Arg Ile Ser Ala Pro Thr Gln Glu Glu Lys Asp Glu Trp Ile Lys Ser
            100                 105                 110

Ile Gln Ala Ala Val Ser
        115
```

<210> SEQ ID NO 20
<211> LENGTH: 118
<212> TYPE: PRT
<213> ORGANISM: Homo sapiens

<400> SEQUENCE: 20

```
Asn Pro Asp Arg Glu Gly Trp Leu Leu Lys Leu Gly Gly Gly Arg Val
1               5                   10                  15

Lys Thr Trp Lys Arg Arg Trp Phe Ile Leu Thr Asp Asn Cys Leu Tyr
            20                  25                  30

Tyr Phe Glu Tyr Thr Thr Asp Lys Glu Pro Arg Gly Ile Ile Pro Leu
        35                  40                  45

Glu Asn Leu Ser Ile Arg Glu Val Glu Asp Pro Arg Lys Pro Asn Cys
    50                  55                  60

Phe Glu Leu Tyr Asn Pro Ser His Lys Gly Gln Val Ile Lys Ala Cys
65                  70                  75                  80

Lys Thr Glu Ala Asp Gly Arg Val Val Glu Gly Asn His Val Val Tyr
                85                  90                  95

Arg Ile Ser Ala Pro Ser Pro Glu Glu Lys Glu Glu Trp Met Lys Ser
            100                 105                 110

Ile Lys Ala Ser Ile Ser
        115
```

<210> SEQ ID NO 21
<211> LENGTH: 131
<212> TYPE: PRT
<213> ORGANISM: Homo sapiens

<400> SEQUENCE: 21

```
Ala Val Ile Leu Glu Ser Ile Phe Leu Lys Arg Ser Gln Gln Lys Lys
1               5                   10                  15

Lys Thr Ser Pro Leu Asn Phe Lys Lys Arg Leu Phe Leu Leu Thr Val
            20                  25                  30

His Lys Leu Ser Tyr Tyr Glu Tyr Asp Phe Glu Arg Gly Arg Arg Gly
```

```
        35                  40                  45

Ser Lys Lys Gly Ser Ile Asp Val Glu Lys Ile Thr Cys Val Glu Thr
    50                  55                  60

Val Val Pro Glu Lys Asn Pro Pro Pro Glu Arg Gln Ile Pro Arg Arg
65                  70                  75                  80

Gly Glu Glu Ser Ser Glu Met Glu Gln Ile Ser Ile Ile Glu Arg Phe
                85                  90                  95

Pro Tyr Pro Phe Gln Val Val Tyr Asp Glu Gly Pro Leu Tyr Val Phe
            100                 105                 110

Ser Pro Thr Glu Glu Leu Arg Lys Arg Trp Ile His Gln Leu Lys Asn
        115                 120                 125

Val Ile Arg
    130
```

<210> SEQ ID NO 22
<211> LENGTH: 1209
<212> TYPE: DNA
<213> ORGANISM: Homo sapiens

<400> SEQUENCE: 22

```
atgacagcca tcatcaaaga gatcgttagc agaaacaaaa ggagatatca agaggatgga      60
ttcgacttag acttgaccta tatttatcca aacattattg ctatgggatt tcctgcagaa     120
agacttgaag gcgtatacag gaacaatatt gatgatgtag taaggttttt ggattcaaag     180
cataaaaacc attacaagat atacaatctt tgtgctgaaa gacattatga caccgccaaa     240
tttaattgca gagttgcaca atatcctttt gaagaccata acccaccaca gctagaactt     300
atcaaaccct tttgtgaaga tcttgaccaa tggctaagtg aagatgacaa tcatgttgca     360
gcaattcact gtaaagctgg aaagggacga actggtgtaa tgatatgtgc atatttatta     420
catcggggca aattttttaaa ggcacaagag gccctagatt tctatgggga agtaaggacc    480
agagacaaaa agggagtaac tattcccagt cagaggcgct atgtgtatta ttatagctac     540
ctgttaaaga atcatctgga ttatagacca gtggcactgt tgtttcacaa gatgatgttt     600
gaaactattc caatgttcag tggcggaact tgcaatcctc agtttgtggt ctgccagcta     660
aaggtgaaga tatattcctc caattcagga cccacacgac gggaagacaa gttcatgtac     720
tttgagttcc ctcagccgtt acctgtgtgt ggtgatatca aagtagagtt cttccacaaa     780
cagaacaaga tgctaaaaaa ggacaaaatg tttcactttt gggtaaatac attcttcata     840
ccaggaccag aggaaacctc agaaaaagta gaaaatggaa gtctatgtga tcaagaaatc     900
gatagcattt gcagtataga gcgtgcagat aatgacaagg aatatctagt acttacttta     960
acaaaaaatg atcttgacaa agcaaataaa gacaaagcca accgatactt ttctccaaat    1020
tttaaggtga agctgtactt cacaaaaaca gtagaggagc cgtcaaatcc agaggctagc    1080
agttcaactt ctgtaacacc agatgttagt gacaatgaac ctgatcatta tagatattct    1140
gacaccactg actctgatcc agagaatgaa ccttttgatg aagatcagca tacacaaatt    1200
acaaaagtc                                                             1209
```

<210> SEQ ID NO 23
<211> LENGTH: 354
<212> TYPE: DNA
<213> ORGANISM: Homo sapiens

<400> SEQUENCE: 23

```
aatccagacc gagaaggctg gctattgaaa ctcggaggtg gcagggtaaa gacttggaag      60
```

agacgctggt tcattctgac tgacaactgc ctttactact ttgagtatac cacggataag 120
gagccccgtg gaatcatccc tttagagaat ctgagtatcc gggaagtgga ggactccaaa 180
aaaccaaact gctttgagct ttatatcccc gacaataaag accaagttat caaggcctgc 240
aagaccgagg ctgacgggcg ggtggtggag gggaaccaca ctgtttaccg gatctcagct 300
ccgacgcccg aggagaagga ggagtggatt aagtgcatta aagcagccat cagc 354

<210> SEQ ID NO 24
<211> LENGTH: 354
<212> TYPE: DNA
<213> ORGANISM: Homo sapiens

<400> SEQUENCE: 24
aacccggacc gggagggctg gctcctgaag ctgggggcg ggcgggtgaa gacgtggaag 60
cggcgctggt ttatcctcac agacaactgc ctctactact ttgagtacac cacggacaag 120
gagccccgag gaatcatccc cctggagaat ctgagcatcc gagaggtgga cgaccccccgg 180 aaaccgaact gctttgaact ttacatcccc aacaacaagg ggcagctcat caaagcctgc 240
aaaactgagg cggacggccg agtggtggag ggaaaccaca tggtgtaccg gatctcggcc 300
cccacgcagg aggagaagga cgagtggatc aagtccatcc aggcggctgt gagt 354

<210> SEQ ID NO 25
<211> LENGTH: 354
<212> TYPE: DNA
<213> ORGANISM: Homo sapiens

<400> SEQUENCE: 25
aaccccgacc gcgagggctg gctcctgaag ctgggagggg gccgtgtgaa gacctggaag 60
cgccggtggt tcatcctgac cgataactgc ctctattact ttgaatacac aacagataag 120
gagcccaggg gaatcatccc gttggaaaac ctcagcatca gggaggtgga ggaccccccgg 180 aaacccaact gttttgagct ctacaatccc agccacaaag ggcaggtcat caaggcctgt 240
aagactgagg ccgacggccg cgtggtagag gggaaccatg tggtgtaccg gatctcagcc 300
ccgagcccgg aggagaagga ggagtggatg aaatccatca aagccagtat cagc 354

<210> SEQ ID NO 26
<211> LENGTH: 393
<212> TYPE: DNA
<213> ORGANISM: Homo sapiens

<400> SEQUENCE: 26
gcagtgattc tggagagcat ctttctgaag cgatcccaac agaaaaagaa aacatcacct 60
ctaaacttca agaagcgcct gtttctcttg accgtgcaca aactctccta ctatgagtat 120
gactttgaac gtgggagaag aggcagtaag aagggttcaa tagatgttga gaagatcact 180
tgtgttgaaa cagtggttcc tgaaaaaaat cctcctccag aaagacagat tccgagaaga 240
ggtgaagagt ccagtgaaat ggagcaaatt tcaatcattg aaaggttccc ttatcccttc 300
caggttgtat atgatgaagg gcctctctac gtcttctccc caactgaaga actaaggaag 360
cggtggattc accagctcaa aaacgtaatc cgg 393

<210> SEQ ID NO 27
<211> LENGTH: 389
<212> TYPE: PRT
<213> ORGANISM: Artificial Sequence
<220> FEATURE:

<223> OTHER INFORMATION: Synthetic

<400> SEQUENCE: 27

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Gly Gly Ser Gly Gly Ser Glu Asn Gly Ser Leu Cys Asp
    370                 375                 380

Gln Glu Ile Asp Ser
385
```

```
<210> SEQ ID NO 28
<211> LENGTH: 228
<212> TYPE: PRT
<213> ORGANISM: Artificial Sequence
<220> FEATURE:
<223> OTHER INFORMATION: Synthetic

<400> SEQUENCE: 28

Ile Cys Ser Ile Glu Arg Ala Asp Asn Gly Gly Ser Gly Gly Ser Pro
1               5                   10                  15

Pro Tyr Thr Ile Thr Tyr Phe Pro Val Arg Gly Arg Cys Glu Ala Met
            20                  25                  30

Arg Met Leu Leu Ala Asp Gln Asp Gln Ser Trp Lys Glu Glu Val Val
        35                  40                  45

Thr Met Glu Thr Trp Pro Pro Leu Lys Pro Ser Cys Leu Phe Arg Gln
    50                  55                  60

Leu Pro Lys Phe Gln Asp Gly Asp Leu Thr Leu Tyr Gln Ser Asn Ala
65                  70                  75                  80

Ile Leu Arg His Leu Gly Arg Ser Phe Gly Leu Tyr Gly Lys Asp Gln
                85                  90                  95

Lys Glu Ala Ala Leu Val Asp Met Val Asn Asp Gly Val Glu Asp Leu
            100                 105                 110

Arg Cys Lys Tyr Ala Thr Leu Ile Tyr Thr Asn Tyr Glu Ala Gly Lys
        115                 120                 125

Glu Lys Tyr Val Lys Glu Leu Pro Glu His Leu Lys Pro Phe Glu Thr
    130                 135                 140

Leu Leu Ser Gln Asn Gln Gly Gly Gln Ala Phe Val Val Gly Ser Gln
145                 150                 155                 160

Ile Ser Phe Ala Asp Tyr Asn Leu Leu Asp Leu Leu Arg Ile His Gln
                165                 170                 175

Val Leu Asn Pro Ser Cys Leu Asp Ala Phe Pro Leu Leu Ser Ala Tyr
            180                 185                 190

Val Ala Arg Leu Ser Ala Arg Pro Lys Ile Lys Ala Phe Leu Ala Ser
        195                 200                 205

Pro Glu His Val Asn Arg Pro Ile Asn Gly Asn Gly Lys Gly His His
    210                 215                 220

His His His His
225
```